(12) United States Patent
Copeland et al.

(10) Patent No.: US 11,890,315 B2
(45) Date of Patent: *Feb. 6, 2024

(54) STABLE ASCORBIC ACID COMPOSITIONS AND METHODS OF USING SAME

(71) Applicant: RENOVION, INC., Chapel Hill, NC (US)

(72) Inventors: Dan Copeland, Chapel Hill, NC (US); Carolyn Durham, Chapel Hill, NC (US)

(73) Assignee: RENOVION, INC., Chapel Hill, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 17/938,861

(22) Filed: Oct. 7, 2022

(65) Prior Publication Data

US 2023/0144527 A1 May 11, 2023

Related U.S. Application Data

(63) Continuation of application No. 16/764,781, filed as application No. PCT/US2018/061686 on Nov. 16, 2018, now Pat. No. 11,497,786.

(60) Provisional application No. 62/684,700, filed on Jun. 13, 2018, provisional application No. 62/588,300, filed on Nov. 17, 2017.

(51) Int. Cl.
| | |
|---|---|
| *A61K 38/06* | (2006.01) |
| *A61K 47/02* | (2006.01) |
| *A61K 47/12* | (2006.01) |
| *A61P 11/00* | (2006.01) |
| *A61K 9/00* | (2006.01) |
| *A61K 9/08* | (2006.01) |
| *A61K 9/14* | (2006.01) |
| *A61K 31/4418* | (2006.01) |
| *A61K 31/47* | (2006.01) |
| *A61K 45/06* | (2006.01) |

(52) U.S. Cl.
CPC ............ *A61K 38/063* (2013.01); *A61K 47/02* (2013.01); *A61K 47/12* (2013.01); *A61P 11/00* (2018.01); *A61K 9/0075* (2013.01); *A61K 9/0078* (2013.01); *A61K 9/08* (2013.01); *A61K 9/14* (2013.01); *A61K 31/4418* (2013.01); *A61K 31/47* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2,606,903 A | 8/1952 | Ruskin | |
| 4,861,783 A | 8/1989 | Ackerman et al. | |
| 4,968,716 A | 11/1990 | Markham | |
| 5,070,085 A | 12/1991 | Markham | |
| 5,238,683 A | 8/1993 | Crystal | |
| 5,304,724 A | 4/1994 | Newton et al. | |
| 5,626,883 A | 5/1997 | Paul | |
| 5,824,693 A | 10/1998 | Goldberg | |
| 5,829,449 A | 11/1998 | Hersh et al. | |
| 5,989,521 A | 11/1999 | Crystal | |
| 6,159,500 A | 12/2000 | Demopoulos et al. | |
| 6,228,347 B1 | 5/2001 | Hersh | |
| 6,312,734 B1 | 11/2001 | Kozhemyakin et al. | |
| 6,350,467 B1 | 2/2002 | Demopoulos et al. | |
| 6,423,687 B1 | 7/2002 | Demopoulos et al. | |
| 6,601,580 B1 | 8/2003 | Bloch | |
| 6,723,703 B2 | 4/2004 | Gaston et al. | |
| 6,764,693 B1 | 7/2004 | Smith | |
| 7,026,342 B2 | 4/2006 | Wagle et al. | |
| 7,384,976 B2 | 6/2008 | Garvey | |
| 9,308,234 B2 | 4/2016 | Arnold et al. | |
| 10,328,152 B2 | 6/2019 | Patel et al. | |
| 10,406,200 B2 | 9/2019 | Arnold et al. | |
| 11,058,743 B2 | 7/2021 | Arnold et al. | |
| 11,344,529 B2 | 5/2022 | Van Wyk et al. | |
| 11,497,786 B2 * | 11/2022 | Copeland | A61K 47/12 |
| 2002/0037855 A1 | 3/2002 | Stanislaus | |

(Continued)

FOREIGN PATENT DOCUMENTS

| | | |
|---|---|---|
| AU | 2004315267 A1 | 8/2005 |
| AU | 2004315267 B2 | 1/2009 |

(Continued)

OTHER PUBLICATIONS

Avgeri, S.G., et al., "Therapeutic Options for Burkholderia Cepacia Infections Beyond Co-trimoxazole: a Systematic Review of the Clinical Evidence," International Journal of Antimicrobial Agents 33(5):394-404, Elsevier Science Publishers, Netherlands (May 2009).
Bishop, C., et al., "A Pilot Study of the Effect of Inhaled Buffered Reduced Glutathione on the Clinical Status of Patients with Cystic Fibrosis," Chest Journal 127 (1):308-317, Elsevier, Netherlands (2005).
Bjarnsholt, T., et al., "The role of bacterial biofilms in chronic infections," 136:1-51, APMIS Suppl., Blackwell Publishing Ltd., United States (2013).
Boies, et al., "Fundamentals of Otolaryngology," W. B. Saunders Co., Philadelphia, 1989, pp. 184.

(Continued)

*Primary Examiner* — Christina Bradley
(74) *Attorney, Agent, or Firm* — STERNE, KESSLER, GOLDSTEIN & FOX P.L.L.C.

(57) ABSTRACT

The application is directed a composition comprising organic acid (e.g., ascorbic acid), glutathione, a glutathione derivative, a glutathione conjugate, a pharmaceutically-acceptable salt thereof, or any combination thereof, and methods of using the same. In certain aspects the application is directed to glutathione, a glutathione derivative, a glutathione conjugate, a pharmaceutically-acceptable salt thereof; and an organic acid; wherein the molar ratio is about 0.5-1:1. The composition can further comprises a bicarbonate salt, wherein the molar ratio is about 0.1-0.5:0.5-1:1.

23 Claims, 17 Drawing Sheets

(56) References Cited

U.S. PATENT DOCUMENTS

| | | |
|---|---|---|
| 2002/0136763 A1 | 9/2002 | Demopoulos et al. |
| 2002/0165207 A1 | 11/2002 | Rosenbloom |
| 2002/0179103 A1 | 12/2002 | Hersh et al. |
| 2003/0064494 A1 | 4/2003 | Kumar et al. |
| 2003/0119909 A1 | 6/2003 | Stanislaus |
| 2004/0071770 A1 | 4/2004 | Smith |
| 2004/0229815 A1 | 11/2004 | Nagasawa et al. |
| 2006/0018945 A1 | 1/2006 | Britigan et al. |
| 2006/0204557 A1 | 9/2006 | Gupta et al. |
| 2006/0228693 A1 | 10/2006 | Soll |
| 2006/0258599 A1 | 11/2006 | Childers |
| 2007/0049641 A1 | 3/2007 | Tirouvanziam et al. |
| 2008/0008694 A1 | 1/2008 | Elgebaly et al. |
| 2009/0214674 A1 | 8/2009 | Barraud et al. |
| 2009/0270310 A1 | 10/2009 | Whyte |
| 2010/0310541 A1 | 12/2010 | Kessler et al. |
| 2010/0311837 A1 | 12/2010 | Sakai et al. |
| 2012/0021071 A1 | 1/2012 | Bordeau et al. |
| 2012/0093947 A1 | 4/2012 | Britigan et al. |
| 2013/0084336 A1 | 4/2013 | Friedman et al. |
| 2013/0129815 A1 | 5/2013 | Guilford et al. |
| 2015/0010654 A1* | 1/2015 | Arnold .............. A61K 31/198 424/717 |
| 2015/0374626 A1 | 12/2015 | Guilford |
| 2016/0367620 A1 | 12/2016 | Demopoulos |
| 2016/0367621 A1 | 12/2016 | Demopoulos et al. |
| 2019/0231686 A1 | 8/2019 | Burch |
| 2019/0351005 A1* | 11/2019 | Copeland .............. A61K 47/22 |
| 2020/0179478 A1 | 6/2020 | Arnold et al. |
| 2020/0361973 A1 | 11/2020 | Liu et al. |
| 2022/0000966 A1 | 1/2022 | Hoag et al. |
| 2022/0143129 A1 | 5/2022 | Arnold et al. |

FOREIGN PATENT DOCUMENTS

| | | |
|---|---|---|
| AU | 2005305456 B2 | 5/2011 |
| CA | 2058793 A1 | 7/1992 |
| CA | 2339473 A1 | 2/2000 |
| CA | 2620123 A1 | 3/2007 |
| CA | 2620123 C | 11/2011 |
| CN | 1921876 A | 2/2007 |
| CN | 101175499 B | 12/2010 |
| CN | 101987195 A | 3/2011 |
| CN | 102100904 B | 4/2013 |
| CN | 102329370 B | 7/2015 |
| DE | 19935763 A1 | 2/2001 |
| DE | 102004035113 A1 | 2/2006 |
| EP | 0938331 B1 | 12/2002 |
| EP | 1282416 A2 | 2/2003 |
| EP | 1701732 A2 | 9/2006 |
| EP | 1474158 B1 | 10/2009 |
| EP | 1333823 B1 | 3/2010 |
| JP | 2004514650 A | 5/2004 |
| JP | 4652664 B2 | 3/2011 |
| WO | WO-9819694 A1 | 5/1998 |
| WO | WO-1999000106 A1 | 1/1999 |
| WO | WO-2001002004 A1 | 1/2001 |
| WO | WO-01089520 A2 | 11/2001 |
| WO | WO-01089520 A3 | 11/2001 |
| WO | WO-0232418 A1 | 4/2002 |
| WO | WO-2002091866 A1 | 11/2002 |
| WO | WO-2005074903 A2 | 8/2005 |
| WO | WO-2005074903 A3 | 8/2005 |
| WO | WO-2005120457 A1 | 12/2005 |
| WO | WO-2006054304 A2 | 5/2006 |
| WO | WO-2006060120 A2 | 6/2006 |
| WO | WO-2006060120 A3 | 6/2006 |
| WO | WO-2007024876 A2 | 3/2007 |
| WO | WO-2007024876 A3 | 3/2007 |
| WO | WO-2007134180 A2 | 11/2007 |
| WO | WO-2009001884 A1 | 12/2008 |
| WO | WO-2009069291 A1 | 6/2009 |
| WO | WO-2010033292 A2 | 3/2010 |
| WO | WO-2010086530 A1 | 8/2010 |
| WO | WO-2010131038 A2 | 11/2010 |
| WO | WO-2012017367 A1 | 2/2012 |
| WO | WO-2012027603 A2 | 3/2012 |
| WO | WO-2012085582 A1 | 6/2012 |
| WO | WO-2014070769 A1 | 5/2014 |
| WO | WO-2014127245 A1 | 8/2014 |
| WO | WO-2014132123 A2 | 9/2014 |
| WO | WO-2016037166 A1 | 3/2016 |
| WO | WO-2016067283 A1 | 5/2016 |
| WO | WO-2016088116 A1 | 6/2016 |
| WO | WO-2018094278 A1 | 5/2018 |
| WO | WO-2019099946 A1 | 5/2019 |

OTHER PUBLICATIONS

Boyanova, et al., "Coadministration of probiotics with antibiotics: why, when and for how long?," Expert Rev Anti Infect Ther 10(4):407-409, Taylor & Francis, United States (2014).

Bray, T.M., and Taylor, C.G., "Tissue Glutathione, Nutrition, and Oxidative Stress," Canadian Journal of Physiology and Pharmacology 71(9):746-751, Canadian Science Publishing, Canada (Sep. 1993).

Cursino, L., et al., "Synergic interaction between ascorbic acid and antibiotics against Pseudomonas aeruginosa," Brazilian Archives of Biology and Technology 48(3): 379-384, Brazilian Archives of Biology and Technology, Brazil (2005).

Donnelly, L.E., et al., "Defective Phagocytosis in Airways Disease," Chest 141(4):1055-1062, Elsevier, Netherlands (2012).

Fitzpatrick, A.M., et al., "Glutathione oxidation is associated with airway macrophage functional impairment in children with severe asthma," Pediatric Res 69(2):154-159, International Pediatric Research Foundation Inc., United States (2011).

International Search Report and Written Opinion for Application No. PCT/US2018/061686, dated Jan. 25, 2019, 8 pages.

Klockgether, J., et al., "Genome Diversity of Pseudomonas Aeruginosa PAO1 Laboratory Strains," Journal of Bacteriology, 192(4):1113-1121, American Society for Microbiology, United States (Feb. 2010).

Sánchez, C. et al., "Inter-Subject Variability in Human Atrial Action Potential in Sinus Rhythm versus Chronic Atrial Fibrillation," PLOS One 9(8):e105897, Public Library of Science, United States (2014).

Sass, A.M., et al., "The Unexpected Discovery of a Novel Low-oxygen-activated Locus for the Anoxic Persistence of Burkholderia Cenocepacia," The ISME Journal 7(8):1568-1581, Nature Publishing Group, England (Aug. 2013).

Schwab, U., et al., "Localization of Burkholderia Cepacia Complex Bacteria in Cystic Fibrosis Lungs and Interactions With Pseudomonas Aeruginosa in Hypoxic Mucus," Infection and immunity 82(11):4729-4745, American Society for Microbiology, United States (Nov. 2014).

Shields, R.K., et al., "*Staphylococcus aureus* Infections in the Early Period After Lung Transplantation: Epidemiology, Risk Factors, and Outcomes," The Journal of Heart and Lung Transplantation 31(11):1199-1206, Elsevier, United States (Nov. 2012).

Simpson, G.LW. and Ortwerth, B.J., "The Non-Oxidative Degradation of Ascorbic Acid at Physiological Conditions", Biochimica et Biophysica Acta, 1501(1):12-24, Elsevier Pub. Co, Netherlands (Apr. 2000).

Taglietti, A., et al., "Antibacterial Activity of Glutathione-Coated Silver Nanoparticles against Gram Positive and Gram Negative Bacteria," Langmuir, 28(21):8140-8148, American Chemical Society, United States (May 2012).

Tong, S.Y.C., et al., "*Staphylococcus aureus* Infections: Epidemiology, Pathophysiology, Clinical Manifestations, and Management," Clinical Microbiology Reviews 28(3):603-661, American Society for Microbiology, United States (Jul. 2015).

Varga, J.J., et al., "Genotypic and Phenotypic Analyses of a Pseudomonas Aeruginosa Chronic Bronchiectasis Isolate Reveal Differences From Cystic Fibrosis and Laboratory Strains," BMC Genomics 16:883, BioMed Central, England (Oct. 2015).

Visca, A., et al., "Improvement in clinical markers in CF patients using a reduced glutathione regimen: An uncontrolled, observational study," Journal of Cystic Fibrosis 7:433-436, Elsevier, Netherlands (2008).

(56) References Cited

OTHER PUBLICATIONS

Wagner, T., et al., "Effects of Azithromycin on Clinical Isolates of Pseudomonas Aeruginosa From Cystic Fibrosis Patients," Chest 128(2):912-919, Elsevier, United States (Aug. 2005).
Zhang, Y and Duan, K., "Glutathione Exhibits Antibacterial Activity and Increases Tetracycline Efficacy against Pseudomonas Aeruginosa," Science China Life Sciences, 52(6):501-505, Science in China Press, co published with Springer-Verlag, China (Jun. 2009).
Zhao, J., et al., "Decade-long Bacterial Community Dynamics in Cystic Fibrosis Airways," Proceedings of the National Academy of Sciences of the United States of America 109(15):5809-5814, National Academy of Sciences, United States (Apr. 2012).
Atkuri et al. "N-Acetylcysteine-a safe antidote for cysteine/ glutathione deficiency" Current Opinion in Pharmacology 7(4):355-359 (2007).
Bergamini et al. "Azithromycin Decreases Glutathione-S-Transferase T1 (GSTT1) and M1 (GSTM1) Expression and Activity in Cystic Fibrosis Airway Epithelial Cells" Pediatric Pulmonology 42(Suppl. 30):297 Abstract 269 (2007) (1 page).
Bergamini et al. "Effects of Azithromycin on Glutathione S-Transferases in Cystic Fibrosis Airway Cells" American Journal of Respiratory Cell and Molecular Biology 41(2):199-206 (2009).
Brechbuhl et al. "Glutathione transport is a unique function of the ATP-binding cassette protein ABCG2" Journal of Biological Chemistry 285(22):16582-16587 (2010).
Cantin, A.M., "Potential for antioxidant therapy of cystic fibrosis" Current Opinion in Pulmonary Medicine 10(6):531-536 (2004).
Caraher et al. "The effect of recombinant human lactoferrin on growth and the antibiotic susceptibility of the cystic fibrosis pathogen Burkholderia cepacia complex when cultured planktonically or as biofilms" Journal of Antimicrobial Chemotherapy 60:546-554 (2007).
Carter, Chris J. "Pathogen and autoantigen homologous regions within the cystic fibrosis transmembrane conductance regulator (CFTR) protein suggest an autoimmune treatable component of cystic fibrosis" FEMS Immunology and Medical Microbiology 62(2):197-214 (2011).
Cheluvappa et al. "Reactions of Pseudomonas aeruginosa pyocyanin with reduced glutathione" Acta Biochimica Polonica 55(3):571-580 (2008).
Cheng et al. "The PDZ domain protein CAL interacts with mGluR5a and modulates receptor expression" Journal of Neurochemistry 112(3):588-598 (2010).
Childers et al. "A new model of cystic fibrosis pathology: Lack of transport of glutathione and its thiocyanate conjugates" Medical Hypotheses 68(1):101-112 (2007).
Ciofu et al. "Respiratory bacterial infections in cystic fibrosis" Current Opinion in Pulmonary Medicine 19:251-258 (2013).
Clunes et al. "Cystic fibrosis: the mechanisms of pathogenesis of an inherited lung disorder" Drug Discovery Today 4(2):63-72 (2007).
Colombo (Curr Opin Pulm Med 9:504-508, 2003) (Year: 2003).
Conner et al. "The lactoperoxidase system links anion transport to host defense in cystic fibrosis" Federation of European Biochemical Societies Letters 581:271-278 (2007).
Dauletbaev et al. "A Phase II Study on Safety and Efficacy of High-Dose N-Acetylcysteine in Patients with Cystic Fibrosis" European Journal of Medical Research 14(8):352-358 (2009).
Day et al. "Role for Cystic Fibrosis Transmembrane Conductance Regulator Protein in a Glutathione Response to Bronchopulmonary Pseudomonas Infection" Infection and Immunity 72(4):2045-2051 (2004).
Day, Brian J. "Glutathione-A Radical Treatment for Cystic Fibrosis Lung Disease?" Chest 127(1):12-14 (2005).
Donnelly et al. "Defective Phagocytosis in Airways Disease" Chest 141(4):1055-1062 (2012).
D'Orazio et al. "Extracellular Glutathione Decreases the Ability of Burkholderia cenocepacia to Penetrate into Epithelial Cells and to Induce an Inflammatory Response" PLOS One 7(10):e47550 (2012).
Elsheikh et al. "Enhanced antigenicity leads to altered immunogenicity in sulfamethoxazole-hypersensitive patients with cystic fibrosis" Journal of Allergy and Clinical Immunology 127(6):15431551.e3 (2011).
England et al., Nasal pH measurement: a reliable and repeatable parameter (Clin Otolaryngol Allied Sci. Feb. 1999;24(1):(67-68).
Feuillet-Fieux et al. "Glutathione S-transferases Related to P. aeruginosa Lung Infection in Cystic Fibrosis Children: Preliminary Study" Clinical Biochemistry 42(1-2):57-63 (2009).
Fischer "Mechanisms and Function of DUOX in Epithelia of the Lung" Antioxidants & Redox Signaling 11(10):2453-2465 (2009).
Fisher et al. (Anesth Analg. Sep.-Oct. 1966;45(5):531-4) (Year: 1966).
Flamant et al. "Glutathione-S-transferase M1 M3, P1 and T1 polymorphisms and severity of lung disease in children with cystic fibrosis" Pharmacogenetics 14(5):295-301 (2004).
Gao et al. "Abnormal glutathione transport in cystic fibrosis airway epithelia" American Journal of Physiology-Lung Cellular and Molecular Physiology 21:L113-L118 (1999).
Gao et al. "Synthetic chloride channel restores glutathione secretion in cystic fibrosis airway epithelia" American Journal of Physiology-Lung Cellular and Molecular Physiology 281(1):L24-L30 (2001).
Geller "Aerosol Antibiotics in Cystic Fibrosis" Respiratory Care 54(5):658-670 (2009).
Gerson et al. "The Lactoperoxidase System Functions in Bacterial Clearance of Airways" Am J. Respir. Cell Mol. Biol. 22:665-671 (2000).
Gould et al. "Targeting maladaptive glutathione responses in lung disease" Biochemical Pharmacology 81(2):187-193 (2011).
Govindaraju et al. "Analysis of Glutathione in Rat Airway Surface Liquid by Capillary Zone Electrophoresis with Conductivity Detection" Journal of Chromatography B-Analytical Technologies in the Biomedical and Life Sciences 788(2):369-376 (2003).
Griese et al. "Improvement of Alveolar Glutathione and Lung Function but Not Oxidative State in Cystic Fibrosis" American Journal of Respiratory and Critical Care Medicine 169(7):822-828 (2004).
Griese et al. "Inhalation Treatment with Glutathione in Patients with Cystic Fibrosis" American Journal of Respiratory and Critical Care Medicine 188:83-89 (2013).
Grigoras et al. "Functional Characterization of the Saccharomyces cerevisiae ABC-transporter Yor1p Overexpressed in Plasma Membranes" Biochimica Biophysica Acta-Biomembranes 1778(1):68-78 (2008).
Gukasyan et al. "Glutathione and its transporters in ocular surface defense" The Ocular Surface 5(4):269-279 (2007).
Hartl et al. "Inhaled glutathione decreases $PGE_2$ and increases lymphocytes in cystic fibrosis lungs" Free Radical Biology and Medicine 39(4):463-472 (2005).
Wood et al. "Biomarkers of lipid peroxidation, airway inflammation and asthma" European Respiratory Journal 21(1):177-186 (2003).
Hector et al. "Glutathione in Airway Neutrophils in Cystic Fibrosis" Pediatric Pulmonology 44(Suppl. 32) Abstract 420:359-360 (2009).
Hector et al. "Novel Method to Process Cystic Fibrosis Sputum for Determination of Oxidative State" Respiration 80(5):393-400 (2010).
Henrion-Caude et al. "Liver disease in pediatric patients with cystic fibrosis is associated with glutathione S-transferase P1 polymorphism" Hepatology 36(4):913-917 (2002).
Howell et al. "ATP hydrolysis by a CFTR domain: Pharmacology and effects of G551D mutation" Biochemical and Biophysical Research Communications 271(2):518-525 (2000).
Huang et al. "Airway Microbiota and Bronchial Hyperresponsiveness in Patients with Suboptimally Controlled Asthma" Journal of Allergy and Clinical Immunology 127(2):372-381.e3 (2011).
Hudson, Valerie "Differing Compartments of Intracellular Glutathione Have Differing Levels of Glutathione in Cystic Fibrosis" Medical Hypotheses 68(4):919-920 (2007).
Hudson, Valerie "Rethinking cystic fibrosis pathology: The critical role of abnormal reduced glutathione (GSH) transport caused by CFTR mutation" Free Radical Biology and Medicine 30(12):1440-1461 (2001).

(56) References Cited

OTHER PUBLICATIONS

Inci et al. "Prevention of primary graft dysfunction in lung transplantation by N-acetylcysteine after prolonged cold ischemia" Journal of Heart and Lung Transplantation 29(11):1293-1301 (2010).
Innis et al. "Choline-related supplements improve abnormal plasma methionine-homocysteine metabolites and glutathione status in children with cystic fibrosis" American Journal of Clinical Nutrition 85(3):702-708 (2007).
Lehr "Global Markets for Asthma and COPD Drugs" BCC Research Market Forecasting: 1-159 (2012).
Nagavarapu "Pulmonary Drug Delivery Systems: Technologies and Global Markets" BCC Research Market Forecasting: 1-222 (2012).
Jungas et al. "Glutathione levels and BAX activation during apoptosis due to oxidative stress in cells expressing wild-type and mutant cystic fibrosis transmembrane conductance regulator" Journal of Biological Chemistry 277(31):27912-27918 (2002).
Kariya et al. "A role for CFTR in the elevation of glutathione levels in the lung by oral glutathione administration" American Journal of Physiology-Lung Cellular and Molecular Physiology 292(6):L1590-L1597 (2007).
Kogan et al. "CFTR directly mediates nucleotide-regulated glutathione flux" The EMBO Journal 22(9):1981-1989 (2003).
Korytina, GF "Polymorphism of glutathione S-transferase M1 and P1 in patients with cystic fibrosis and chronic respiratory diseases" Russian Journal of Genetics 40(3):314-320 (2004).
Lands et al. "Lymphocyte Glutathione Levels in Children with Cystic Fibrosis" Chest 116:201-205 (1999).
Lands et al. "Total Plasma Antioxidant Capacity in Cystic Fibrosis" Pediatric Pulmonology 29(2):81-87 (2000).
Lands, Larry C. "Nutrition in pediatric lung disease" Paediatric Respiratory Reviews 8(4):305-312 (2007).
Laskowska-Klita et al. "Antioxidant status in erythrocytes of cystic fibrosis children" Acta Biochimica Polonica 48(1):283-285 (2001).
Lasry et al. "Inflammatory networks underlying colorectal cancer," Nature Immunology, 17, 230-240 (2016).
Li et al. "Spatiotemporal Coupling of cAMP Transporter to CFTR Chloride Channel Function in the Gut Epithelia" Cell 131(5):940-951 (2007).
Lima et al. "Cystic fibrosis transmembrane conductance regulator gene mutations and glutathione S-transferase null genotypes in cystic fibrosis patients in Brazil" Journal Brasileiro De Pneumologia 38(1):50-56 (2012).
Lothian et al. "Effect of whey protein to modulate immune response in children with atopic asthma" International Journal of Food Sciences and Nutrition 57(3-4):204-211 (2006).
Madarasi et al. "Antioxidant Status in Patients with Cystic Fibrosis" Annals of Nutrition and Metabolism 44(5-6):207-211 (2000).
Martin et al. "Host-microbe interactions in distal airways: relevance to chronic airway diseases" European Respiratory Review 24:78-91 (2015).
McKone et al. "Variants in the Glutamate-Cysteine-Ligase Gene Are Associated with Cystic Fibrosis Lung Disease" American Journal of Respiratory and Critical Care Medicine 174(4):415-419 (2006).
Moskwa et al. "A Novel Host Defense System of Airways is Defective in Cystic Fibrosis" American Journal Respir. Crit. Care Med . 175:174-183 (2007).
Murphy, Timothy F. "The role of bacteria in airway inflammation in exacerbations of chronic obstructive pulmonary disease" Current Opinion in Infectious Diseases 19(3):225-230 (2006).
None et al. "Residual Gravimetric Method to Measure Nebulizer Output" Journal of Aerosol Medicine 17(1):63-72 (2004).
O'Brien "Peroxidases" Chemico-Biological Interactions 129:113-139 (2000).
Perez-Vilar et al. "Reevaluating Gel-Forming Mucins' Roles in Cystic Fibrosis Lung Disease" Free Radical Biology and Medicine 37(10):1564-1577 (2004).
Pitt, Bruce R. "CFTR trafficking and signaling in respiratory epithelium" American Journal of Physiology-Lung Cellular and Molecular Physiology 281(1): L13-L15 (2001).

Prousky "The Treatment of Pulmonary Diseases and Respiratory-Related Conditions with inhaled (Nebulized or Aerosolized) Glutathione" eCAM 5(1):27-35 (2008).
Rada "The Pseudomonas Toxin Pyocyanin Inhibits the Dual Oxidase-Based Antimicrobial System as It Imposes Oxidative Stress on Airway Epithelial Cells" J Immunol 181:4883-4893 (2008).
Remund et al. "Infections Relevant to Lung Transplantation" Proceedings of the American Thoracic Society 6:94-100 (2009).
Rogan et al. "Loss of Microbicidal Activity and increased Formation of Biofilm Due to Decreased Lactoferrin Activity in Patients with Cystic Fibrosis" JID 190:1245-1253 (2004).
Roux et al. "Mycobacterium abscessus, pathogène émergent dans la mucoviscidose" Immuno-analyse et biologie specialisee 25(1):26-33 (2010) English Abstract Only.
Schwarzer et al. "Organelle redox of CF and CFTR-corrected airway epithelia" Free Radical Biology and Medicine 43(2):300-316 (2007).
Schwarzer et al. "Oxidative Stress Caused by Pyocyanin Impairs CFTR Cl-Transport in Human Bronchial Epithelial Cells" Free Radical Biology and Medicine 45(12):1653-1662 (2008).
Šidlová et al. "Serum alpha-glutathione S-transferase as a sensitive marker of hepatocellular damage in patients with cystic fibrosis" Physiological Research 52(3):361-365 (2003).
Snyder et al. "Acute effects of aerosolized S-nitrosoglutathione in cystic fibrosis" American Journal of Respiratory and Critical Care Medicine 165(7):922-926 (2002).
Sonni et al. "Antioxidant Action of Glutathione and the Ascorbic Acid/Glutathione Pair in a Model White Wine" Journal of Agricultural and Food Chemistry 59:3940-3949 (2011).
Speich et al. "Epidemiology and Management of Infections after Lung Transplantation" Clinical Infectious Diseases 33(Suppl 1):S58-S65 (2001).
Szentpétery et al. "Functional Studies on the MRP1 Multidrug Transporter: Characterization of ABC-Signature Mutant Variants" Anticancer Research 24(2A):449-455 (2004).
Thomas et al. "Lactoperoxidase, peroxide, thiocyanate antimicrobial system: correlation of sulfhydryl oxidation with antimicrobial action" Infect. Immun. 20(2):456-483 (1978).
Thome et al. "Novel SIN-1 Reactive Intermediates Modulate Chloride Secretion Across Murine Airway Cells" Free Radical Biology and Medicine 35(6):662-675 (2003).
Tirouvanziam et al. "High-dose oral N-acetylcysteine, a glutathione prodrug, modulates inflammation in cystic fibrosis" Proceedings of the National Academy of Sciences of the United States of America 103(12):4628-4633 (2006).
Tournoud et al. "Structural equations to model relationships between pulmonary function, fatty acids and oxidation in cystic fibrosis" Scandinavian Journal of Clinical & Laboratory Investigation 69(1):36-44 (2009).
Vasu et al. "Evaluation of thiol-based antioxidant therapeutics in cystic fibrosis sputum: Focus on myeloperoxidase" Free Radical Research 45(2):165-176 (2011).
Velsor et al. "Antioxidant imbalance in the lungs of cystic fibrosis transmembrane conductance regulator protein mutant mice" American Journal of Physiology—Lung Cellular and Molecular Physiology 281(1):L31-L38 (2001).
Venglarik et al. "Hypochlorous acid alters bronchial epithelial cell membrane properties and prevention by extracellular glutathione" Journal of Applied Physiology 95(6):2444-2452.
Vilela et al. "High hydrostatic pressure enhances whey protein digestibility to generate whey peptides that improve glutathione status in CFTR-deficient lung epithelial cells" Molecular Nutrition & Food Research 50(11):1013-1029 (2006).
Vilela et al. "Inhibition of IL-8 release from CFTR-deficient lung epithelial cells following pre-treatment with fenretinide" International Immunopharmacology 6(11):1651-1664 (2006).
Visca et al. "Improvement in clinical markers in CF patients using a reduced glutathione regimen: An uncontrolled, observational study" Journal of Cystic Fibrosis 7:433-436 (2008).
Wang et al. "Reversible silencing of CFTR chloride channels by glutathionylation" Journal of General Physiology 125(2):127-141 (2005).

(56) References Cited

OTHER PUBLICATIONS

Ward et al. "Lactoferrin and host defense" Biochem. Cell Biol. 80:95-102 (2002).
Willing et al. "Shifting the balance: antibiotic effects on host-microbiota mutualism" Nature Reviews Microbiology 9(4):233-243 (2011) (Abstract Only).
Dewan "Advanced Drug Delivery Systems: Technologies and Global Markets" BCC Research Market Forecasting: 1-278 (2011).
Dewan "Global Markets for Orphan Drugs" BCC Research Market Forecasting: 1-212 (2013).
Highsmith "Biologic Therapeutic Drugs: Technologies and Global Markets" BCC Research Market Forecasting: 1-168 (2013).
Hancock, R.E.W., and Wong, P.G.W., "Compounds Which Increase the Permeability of the Pseudomonas aeruginosa Outer Membrane," Antimicrobial Agents and Chemotherapy, 26(1): 48-52, American Society for Microbiology, United States (1984).
Hubert, D., et al., "Exhaled nitric oxide in cystic fibrosis: relationships with airway and lung vascular impairments," European Respiratory Journal, 34: 117-124, ERS Journal Ltd., Switzerland (2009).
Fischer, H., et al., "Vitamin C controls the cystic fibrosis transmembrane conductance regulator chloride channel," PNAS, 101(10): 3691-3696, The National Academy of Science of the USA, United States (2004).
Fischer, H., and Widdicombe, J.H., Mechanisms of Acid and Base Secretion by the Airway Epithelium, J Membr Biol., 211(3): 139-150, Springer Science, Germany (2006).
Fisher, A. J., et al., "Cross sectional study of exhaled nitric oxide levels following lung transplantation," Thorax, 53: 454-458, British Thoracic Society, United Kingdom (1998).
Jiao, J., et al., "The effects of vitamins C and B12 on human nasal ciliary beat frequency," BMC Complementary and Alternative Medicine 13110): 1-6, Springer Nature, Berlin (2013).
Griese, M., et al., "Inhalation Treatment with Glutathione in Patients with Cystic Fibrosis" Am J Respir Crit Care Med, 188(1): 83-89, The American Thoracic Society, United States (2013).
Birket, S.E., et al., "A Functional Anatomic Defect of the Cystic Fibrosis Airway," Am J Respir Crit Care Med, 190(4): 421-432, The American Thoracic Society, United States (2014).
Liu, L., et al., "Method for Quantitative Study of Airway Functional Microanatomy Using Micro-Optical Coherence Tomography," PLOS One, 8(1): e54473, 8 pages (2013).
Liu, L., et al., "An Autoregulatory Mechanism Governing Mucociliary Transport Is Sensitive to Mucus Load," Am J Prespir Cell Mol Biol., 51(4):485-93, The American Thoracic Society, United States (2014).
Gabbay, E., et al., "Post-lung Transplant Bronchiolitis Obliterans Syndrome (BOS) Is Characterized by Increase exhaled Nitric Oxide Levels and Epithelial Inducible Nitric oxide Synthase," Am J Respir Crit Care Med, 162:2182-2187, American Thoracic Society, United States (2000).
Gaggar, A., et al., "The role of matrix metalloproteases in cystic fibrosis lung disease," Eur Respir J., 38(3):721-727, European Respiratory Society, Switzerland (2011).
Martinez-Alemán, S. R., "Understanding the entanglement: Neutrophil Extracellular Traps (NETs) in Cystic Fibrosis," Front Cell Infect Microbiol., 7:104.
Morice, A.H., "Airway reflux as a cause of respiratory disease," Breathe, 9(4): 256-266, European Respiratory Society, Switzerland (2013).
Tang, X., et al., "Acidic pH increases airways surface liquid viscosity in cystic fibrosis," J Clin Invest., 126(3):879-891, American Society for Clinical Investigation (2016).
Tate, S., et al., "Airways in cystic fibrosis are acidified: detection by exhaled breath condensate," Thorax, 57:926-929, BMJ Publishing Group Ltd & British Thoracic Society, United Kingdom (2002).
Francoeur, C., and Denis, M., "Nitric oxide and interleukin-8 as inflammatory components of cystic fibrosis," Inflammation, 19: 587-598, Springer, Germany (1995).

Dickerhof, N., et al., "Oxidative stress in early cystic fibrosis ling disease is exacerbated by airway glutathione deficiency," Free Radical Biology and Medicine, 113: 236-243, Elsevier, Netherlands (2017).
Kharitonov, S.A., et al., "Increased nitric oxide in exhaled air of asthmatic patients" The Lancet, 343(8890): p. 133-p. 135, Elsevier, Netherlands (1994).
Klare, W., et al., "Glutatione-disrupted biofilms of clinical Pseudomonas aeruginosa strains exhibit an enhanced antibiotic effect and a novel biofilm transcriptome," Antimicrobial Agents and Chemotherapy, 60(8):4539-4551, American Society for Microbiology, United States (2016).
O'Donnell, M.D., et al., "Treatment of Idiopathic Bronchiectasis With Aerosolized Recombinant Human DNase I," Chest, 113(5): 1329-1334, Elsevier, Netherlands (1998).
Paez, P.L., et al., "Effect of the association of reduced glutathione and ciprofloxacin on the antimicrobial activity in *Staphylococcus aureus*," FEMS Microbiology Letters, 303(1):101-105, Oxford University Press, United Kingdom (2010).
Rawal, B.D., et al., "Inhibition of Pseudomonas aeruginosa by ascorbic acid acting singly and in combination with antimicrobials: in-vitro and in-vivo studies," Med J Aust, 1(6): 169-174, John Wiley & Sons, United States (1974).
Sakakura, Y., et al., "Mucociliary Function during experimentally Induced Rhinovirus Infection in Man," Annals of Otology, Rhinology & Laryngology, 82(2): 203-211, Sage Publications, United States (1973).
Vasilenko, A., "Antibacterial activity of glutathione in carbapenemase-producing Klebsiella pneumoniae and Pseudomonas aeruginosa," a Master's Thesis submitted to the Faculty of Richard L. Conolly College, Long Island University in fulfillment of the requirements for the degree of Masters of Science, May 2013, 52 pages.
WebAssign, "Lab 10—Electrochemical Cells," General Chemistry II Labs, accessed at www.webassign.net/question_assets/ncsugenchem2021abv1/lab_10/manual.html, downloaded on Sep. 2, 2020, 8 pages.
De Villiers, B.L., et al., "Optimizing MCPA (K-salt) activity with adjuvants," *South African Journal of Plant and Soil* 17(2):63-65, Taylor and Francis Ltd., United Kingdom (2000).
Pedemonte, et al. "Thiocyanate Transport in Resting and IL-4 Stimulated Human Bronchial Epithelial Cells; Role of Pendrin and Anion Channels," J Immunol 178:5144-5153, American Association of Immunologists, United States (2007).
Aliberti, S., et al., "Criteria and definitions for the radiological and clinical diagnosis of bronchiectasis in adults for use in clinical trials: international consensus recommendations," Lancet Respir Med 2600(21):1-9, Elsevier, Netherlands (Sep. 2021).
Chalmers, J. D., and Hill, A. T., "Mechanisms of immune dysfunction and bacterial persistence in non-cystic fibrosis bronchiectasis," Molecular Immunology 55(1):27-34, Elsevier, Netherlands (Aug. 2013).
Chalmers, J. D., et al., "Bronchiectasis," Nature Reviews Disease Primers 4:45, 18 pages, Nature Publishing Group, United Kingdom (Nov. 2018).
King, P. T., "The pathophysiology of bronchiectasis," Int J Chron Obstruct Pulmon Dis 4:411-419, Dove Press, New Zealand (Nov. 2009).
Nosotti, M., et al., "Infections after lung transplantation," Journal of Thoracic Disease 10(6):3849-3868, Pioneer Bioscience Publishing Company, Hong Kong (Jun. 2018).
Okamoto, K., and Santos, C. A. Q., "Management and prophylaxis of bacterial and mycobacterial infections among lung transplant recipients," Ann Transl Med 8(6):413, 12 pages, AME Publishing Company, China (Mar. 2020).
Schäfer, J., et al., "Pathogenesis, imaging and clinical characteristics of CF and non-CF bronchiectasis," BMC Pulm Med 18(1):79, 11 pages, BioMed Central Ltd., United Kingdom (May 2018).
Fux, C.A., et al., "Can laboratory reference strains mirror 'real-world' pathogenesis?," Trends Microbiol. 13(2):58-63, Elsevier, Netherlands (2005).
Grosso-Becerra, M-V., et al., "Pseudomonas aeruginosa clinical and environmental isolates constitute a single population with high

(56) References Cited

OTHER PUBLICATIONS phenotypic diversity," BMC Genomics 15(318): 1-14, BioMed Central, United Kingdom (2014).

Hanberger, H., et al., "Antibiotic Susceptibility Among Aerobic Gram-negative Bacilli in Intensive Care Units in 5 European Countries," JAMA 281 (1):67-71, American Medical Association, United States (1999).

Hayes, D., et al., "Lung transplantation for advanced bronchiectasis," Semin Respir Crit Care Med 31(2):123-38, American Thoracic Society, United States (Apr. 2010).

Visscher, D. W., et al., "Bronchiolitis: the pathologist's perspective," Proc Am Thorac Soc 3(1):41-47, American Thoracic Society, United States (2006).

Saayman, S., et al., "Cystic Fibrosis Transmembrane Receptor Expression is Regulated by Long Antisense Non-Coding RNAs," Molecular Therapy 22:S4, Cell Press, United States (May 2014).

Sodium Bicarbonate, PubChem ID 516892, accessed at https://pubchem.ncbi.nlm.nih.gov/compound/Sodium-bicarbonate, accessed on Oct. 6, 2022.

Ascorbic Acid, PubChem ID 54670067, accessed at https://pubchem.ncbi.nlm.nih.gov/compound/Ascorbic-acid, accessed on Oct. 6, 2022.

Glutathione, PubChem ID 124886, accessed at https://pubchem.ncbi.nlm.nih.gov/compound/Glutathione, accessed on Oct. 6, 2022.

Sass, R.L., and Scheuerman, R.F., "Sodium Bicarbonate, Entry for Nahcolite," in Handbook of Mineralogy, Mineral Data Publishing, United States (1962).

\* cited by examiner

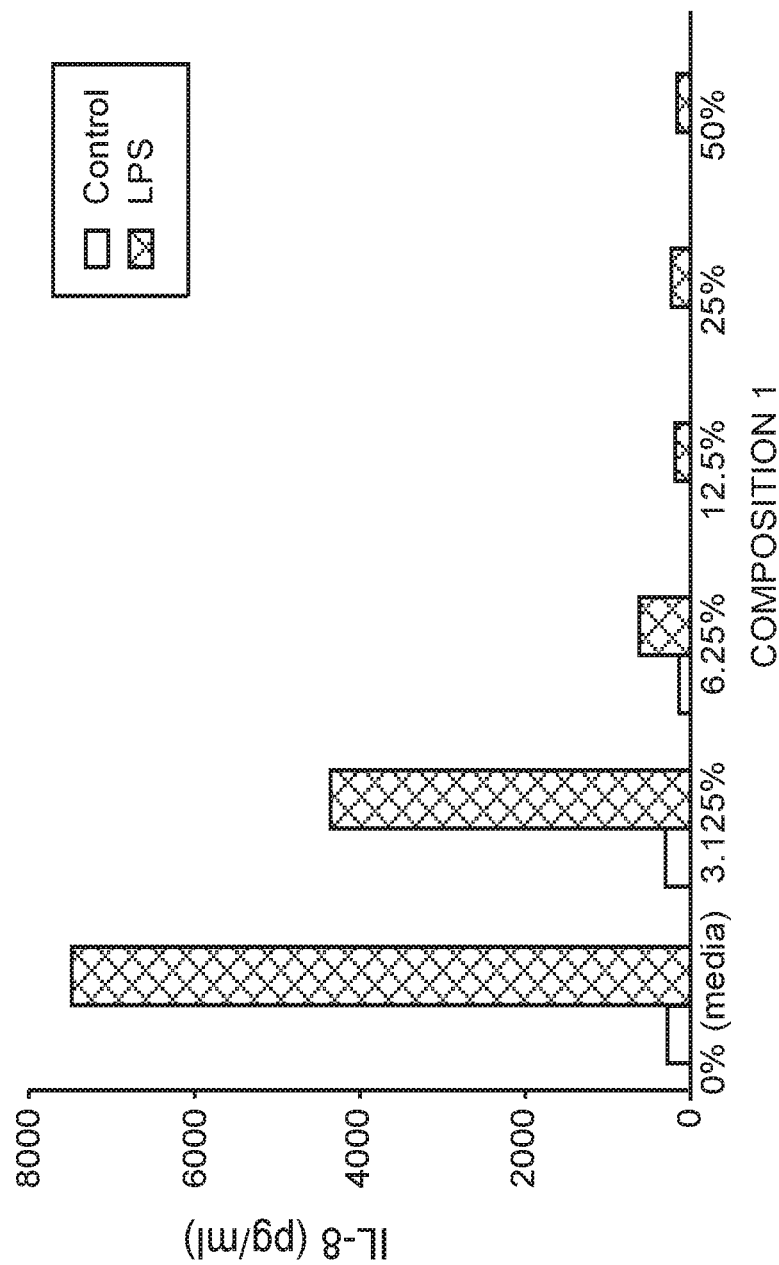

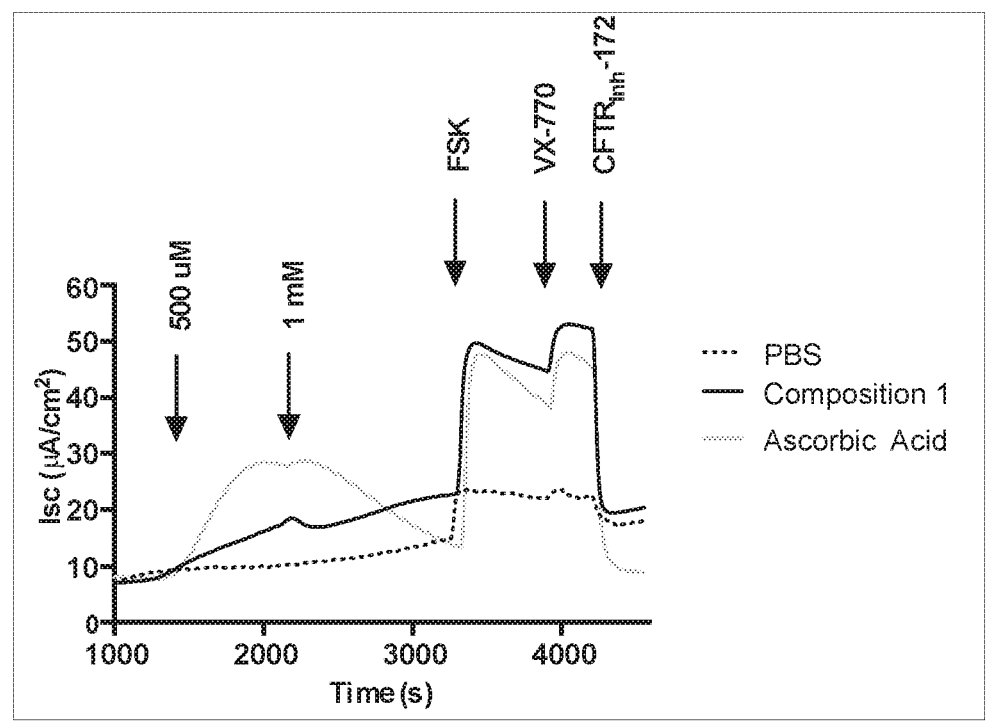
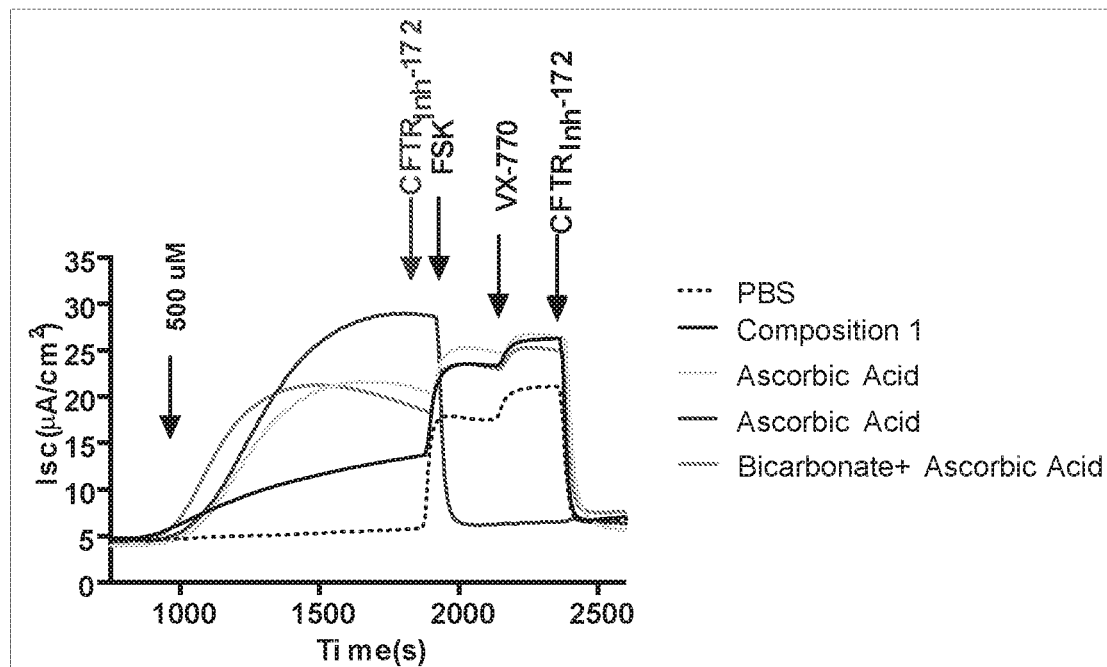
WT CFBE cells
FIG. 6

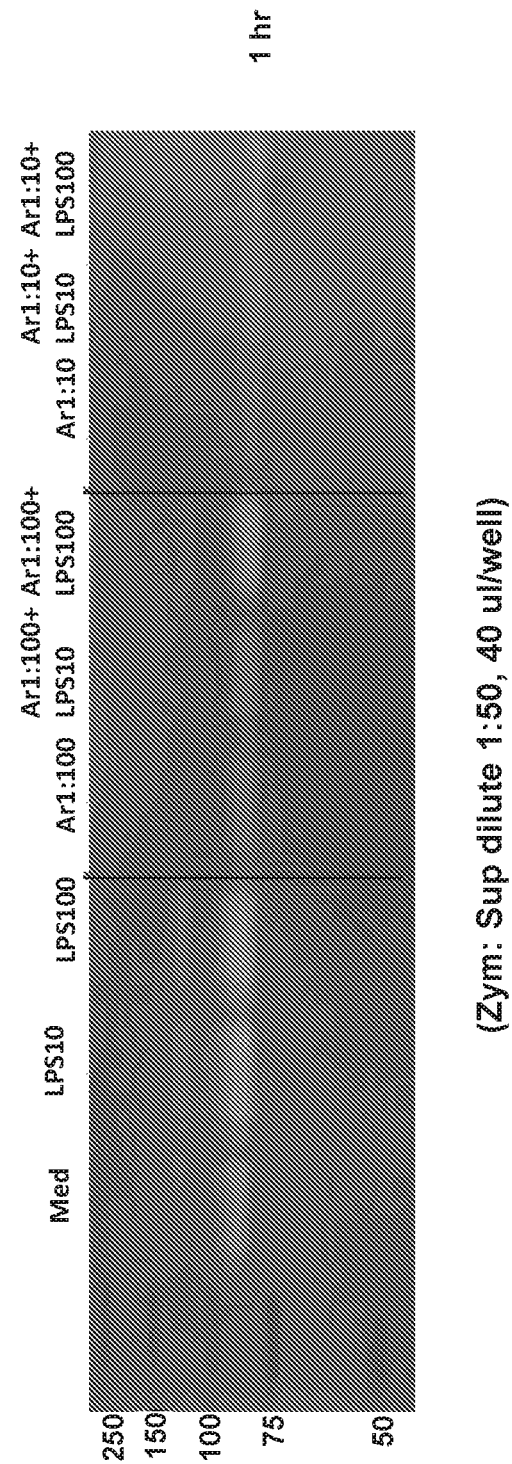

FIG. 11
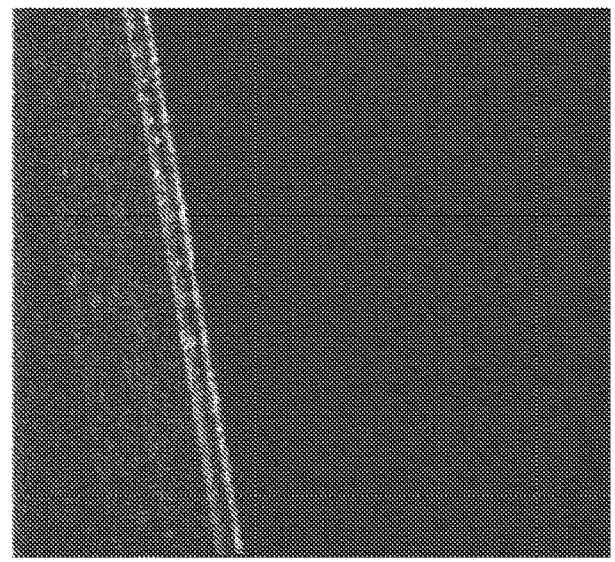
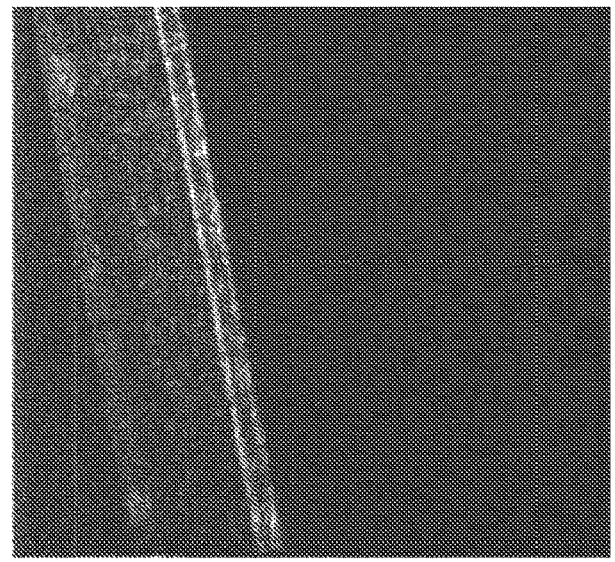
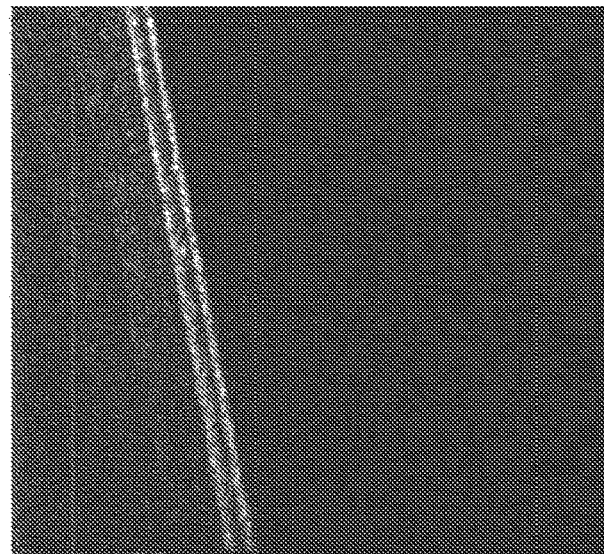

P<0.01, *P<0.001, ****P<0.0001

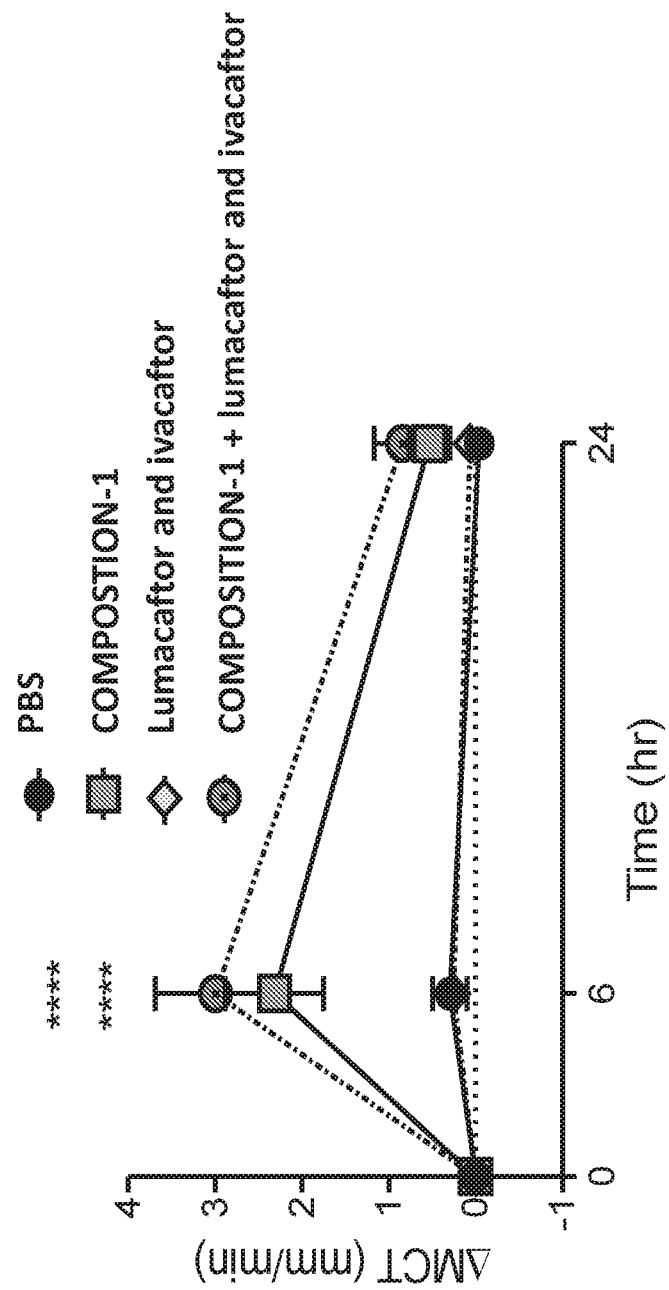

FIG. 14

| Patient | Enrollment (ppb) | Post-Composition 1 (ppb) | % Change in FENO |
|---|---|---|---|
| Patient 02 CF | 18 | 10 | -44% |
| Patient 03 ILD | 18 | 14 | -22% |
| Patient 04 CF | 12 | 6 | -50% |
| Patient 05 A1AT | 13 | 5 | -62% |

FIG. 15

| Formulation based on ratio | Formulation Description (GSH is mid concentration in all Formulations) | Solubility | Precipitate Formation after Storage (72 h, 2-8°C) | Approximate pH after Storage (72 h, 2-8°C) | Impurities after Storage (72 h, 2-8°C) |
|---|---|---|---|---|---|
| 1 | Low ASC, Low Buffer | Poor | Precipitate | <5 (Acidic) | 2.7% |
| 2 | Low ASC, Mid Buffer | Good | None | <5 (Acidic) | 1.5% |
| 3 | Low ASC, High Buffer | Good | None | >7 (Basic) | 7.9% |
| 4 | Mid ASC, Low Buffer | Poor | Precipitate | <5 (Acidic) | 2.6% |
| 5 | Mid ASC, Mid Buffer | Good | None | <5 (Acidic) | 1.9% |
| 6 | Mid ASC, High Buffer | Good | None | >7 (Basic) | 7.8% |
| 7 | High ASC, Low Buffer | Poor | Precipitate | <5 (Acidic) | 2.9% |
| 8 | High ASC, Mid Buffer | Poor | None | <5 (Acidic) | 2.5% |
| 9 (Composition 1) | High ASC, High Buffer | Good | None | 6-7 (Optimal) | 3.8% |

STABLE ASCORBIC ACID COMPOSITIONS AND METHODS OF USING SAME

CROSS-REFERENCE TO RELATED APPLICATIONS

This application is a Continuation of U.S. patent application Ser. No. 16/764,781, 371 (c) date May 15, 2020, which is a 35 U.S.C. § 371 National Stage of International Patent Application No. PCT/US2018/061686, filed Nov. 16, 2018, which claims the priority benefit of U.S. Provisional Application No. 62/588,300, filed Nov. 17, 2017; and U.S. Provisional Application No. 62/684,700, filed Jun. 13, 2018, each of which is hereby incorporated in its entirety.

FIELF OF THE INVENTION

The present disclosure relates to compositions comprising organic acid, glutathione, a glutathione derivative, a glutathione conjugate, a pharmaceutically-acceptable salt thereof, or any combination thereof and their use.

BACKGROUND

Glutathione or "GSH" refers to a compound having the formula:

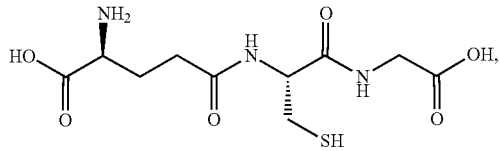 [SMILES: N[C@@H](CCC(=O)N[C@@H](CS)C(=O)NCC(=O)O)C(=O)O]

or a zwitterionic form thereof, e.g., a compound having the formula:

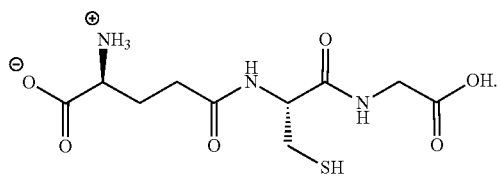 [SMILES: [NH3+][C@@H](CCC(=O)N[C@@H](CS)C(=O)NCC(=O)O)C(=O)[O-]]

In healthy individuals, there are high concentrations of GSH in the airway. However, in individuals with chronic inflammatory airway diseases, such as lung transplant patients, glutathione reserves are depleted. Both inflammation and infection are associated with lung graft rejection/dysfunction and failure. Current therapy for lung transplant, which includes high doses of immunosuppression agents and antimicrobials, has systemic side effects and toxicities that can lead to further inflammation and infections. Additionally, repeated use of high dose antibiotics has been shown to lead to multi-drug resistant infections.

Lower respiratory infections from chronic inflammatory airway diseases present in multiple airway disorders and diseases, including, for example, lung transplant patients and patients with cystic fibrosis (CF) and bronchiectasis (e.g., non-cystic fibrosis bronchiectasis or cystic fibrosis bronchiectasis).

BRIEF SUMMARY

The present disclosure provides compositions comprising: (a) glutathione, a glutathione derivative, a glutathione conjugate, a pharmaceutically-acceptable salt thereof, or any combination thereof; and (b) an organic acid, wherein the molar ratio of (a) to (b) is about 0.5-1:1 and the pH of the formulation is at least 5.5. In some embodiments, the organic acid is ascorbic acid. In some embodiments, the compositon further comprises (c) a bicarbonate salt (e.g., sodium bicarbonate). In some embodiments, the composition does not include a bicarbonate salt.

In some embodiments, the molar ratio of (a):(b):(c) is about 0.1-0.5:0.5-1:1. In some embodiments, the molar ratio of (a):(b):(c) is about 0.4-0.5:0.5-1:1. In some embodiments, the molar ratio of (a):(b):(c) is about 0.4-0.5:0.5:1 or 0.4-0.5:1:1.

In some embodiments, the reduced glutathione in the composition is more than about 80%, more than about 82%, more than about 84%, more than about 85%, more than about 88%, more than about 90%, more than about 91%, more than about 92%, more than about 93%, more than about 94%, more than about 95%, more than about 96%, or more than about 97% by weight of the total glutathione in the composition after storage of the composition for 4 weeks at about 5° C.

In some embodiments, the oxidized glutathione in the composition is less than about 20%, less than about 18%, less than about 16%, less than about 15%, less than about 12%, less than about 10%, less than about 9%, less than about 8%, less than about 7%, less than about 6%, less than about 5%, less than about 4%, or less than about 3% by weight of the total glutathione in the composition after storage of the composition for 4 weeks (e.g., at 5° C. in a $N_2$ atmosphere and/or ambient atmosphere).

In some embodiments, the reduced ascorbic acid is more than about 80%, more than about 85%, more than about 86%, more than about 87%, more than about 88%, more than about 89%, or more than about 90% by weight of the total ascorbic acid in the composition after storage of the composition after storage of the composition for 4 weeks at about 5° C.

In some embodiments, the oxidized ascorbic acid in the composition is less than about 20%, less than about 18%, less than about 16%, less than about 15%, less than about 12%, less than about 10%, or less than about 9% by weight of the total ascorbic acid in the composition after storage of the composition for 4 weeks at about 5° C.

In some embodiments, the composition is stored under ambient conditions, e.g., without nitrogen sparging. In some embodiments, the composition is stored with nitrogen sparging.

In some embodiments, the pH of the composition is about 5.5 to about 10, about 5.5 to about 8, about 6 to about 10, or about 6 to about 8. In some embodiments, the pH is about 5.5, about 6.5, about 7.0, or about 7.5. In some embodiments, the pH of the composition is 7±1.5. In some embodiments, the pH of the composition is about 6.

In some embodiments, the composition is an aqueous solution, a dry powder, or lyophilized.

Certain aspects of the disclosure are directed to a method of inhibiting or reducing growth of a clinical isolate bacteria comprising contacting the clinical isolate with a composition of the disclosure.

Certain aspects of the disclosure are directed to a method of inhibiting or reducing formation of a clinical isolate bacteria biofilm comprising contacting the clinical isolate with a composition comprising a composition of the disclosure.

Certain aspects of the disclosure are directed to a method of treating or reducing symptoms in a subject suffering from or at risk for a clinical isolate bacterial infection comprising contacting the clinical isolate with a composition of the disclosure.

In some embodiments, the subject has a pulmonary or airway disease or disorder. In some embodiments, the pulmonary or airway disease or disorder is cystic fibrosis or non-cystic fibrosis bronchiectasis.

Certain aspects of the disclosure are directed to a method of upregulating mucociliary clearance in a subject suffering from or at risk of impaired mucociliary clearance comprising administering to the subject a composition of the disclosure. In some embodiments, administering the composition decreases mucus viscosity of the patient. In some embodiments, administering the composition increases ciliary beat frequency of the patient's airway epithelial cells. In some embodiments, administering the composition increases the mucociliary transport rate of the patient's airway epithelial cells. In some embodiments, administering said composition increases the airway surface liquid height of the patient.

In some embodiments, the airway epithelium of the patient is not colonized by bacteria. In some embodiments, the airway epithelium of the patient is colonized by bacteria. In some embodiments, the patient suffers from an active bacterial infection. In some embodiments, the patient does not suffer from an active bacterial infection.

Certain aspects of the disclosure are directed to a method of reducing airway inflammation in a subject suffering from or at risk of airway inflammation comprising administering to the subject a composition of the disclosure.

In some embodiments, administering said composition inhibits myeloperoxidase activity of the patient's neutrophils. In some embodiments, administering said composition decreases the formation of neutrophil extracellular traps. In some embodiments, administering said composition downregulates the production of nitric oxide from the patient's neutrophils. In some embodiments, administering said composition reduces the patient's fractional exhaled nitric oxide (FeNO) by at least 20%. In some embodiments, the composition is administered twice a daily. In some embodiments, the composition is administered by nebulizer. In some embodiments, the administering the composition reduces the patient's fractional exhaled nitric oxide (FeNO) by at least 20% after 1 month of administration (e.g., twice daily) of the composition.

In some embodiments, administering said composition downregulates the production of at least one pro-inflammatory cytokine (e.g., TNF-α, IL-6, and/or IL-8) and/or at least one neutrophil and macrophage-associated cytokine (e.g., MIP1α and/or MIP1β).

Certain aspects of the disclosure are directed to a method of decreasing mucus viscosity in a subject suffering from or at risk of suffering from decreased mucus viscosity comprising administering to the subject a composition of the disclosure.

Certain aspects of the disclosure are directed to a method of activating cystic fibrosis transmembrane receptor (CFTR) function in a subject suffering from decreased CFTR function comprising administering to the subject a composition of the disclosure.

Certain aspects of the disclosure are directed to a method of enhancing the expression of cystic fibrosis transmembrane receptor (CFTR) in a subject suffering from decreased expression of CFTR comprising administering to the subject a composition of the disclosure.

Certain aspects of the disclosure are directed to a method comprising administering a composition of the disclosure in combination with a CFTR therapy selected from the group consisting of a CFTR amplifer (e.g., PTI-428), a CFTR corrector (e.g., VX-809 (lumacaftor), VX-661 (tezacaftor), VX-445, VX-659, VX-152, FDL169, GLPG2222, PT-801, or combinations thereof), a CFTR potentiator/modulator (e.g., VX-770 (ivacaftor), QBW 251, VX-561, PT1-808, or combinations thereof), a CFTR RNA modifier (e.g., QR-100, MRT5005, or the combination thereof), or any combination thereof. In some embodiments, the administration of the CFTR therapy is simultaneous or consecutive to administration of the composition of the disclosure to the subject and in any order (e.g., the composition can be administered before or after the CFTR therapy). In some embodiments, the CFTR therapy is administered orally and the composition of the disclosure is administered by inhalation. In some embodiments, both the cystic fibrosis therapy and the composition of the disclosure are administered by inhalation.

In some embodiments, the methods comprise administering a composition of the disclosure in combination with VX-770 (ivacaftor), VX-809 (lumacaftor), or the combination thereof to the subject.

In some embodiments, administering a composition of the disclosure in combination with administering VX-770 (ivacaftor), VX-809 (lumacaftor), or the combination of VX-770/VX-809 to a subject decreases mucus viscosity in the airway of the subject more than administering the composition of the disclosure or VX-770 (ivacaftor), VX-809 (lumacaftor), or the combination of VX-770/VX-809 alone.

In some embodiments, administering a composition of the disclosure in combination with administering VX-770 (ivacaftor), VX-809 (lumacaftor), or the combination of VX-770/VX-809 to a subject increases ciliary beat frequency of the subject's airway epithelial cells more than administering the composition alone.

In some embodiments, administering a composition of the disclosure in combination with administering VX-770 (ivacaftor), VX-809 (lumacaftor), or the combination of VX-770/VX-809 to a subject increases the mucociliary transport rate of the subject's airway epithelial cells more than administering the composition alone.

In some embodiments, administering a composition of the application in combination with administering VX-770, VX-809, or the combination of VX-770/VX-809 to the subject increases the airway surface liquid height of the subject more than administering the composition alone.

In some embodiments, the composition of the disclosure is administered in combination with VX-770, VX-809, or the combination of VX-770/VX-809, wherein the administration is simultaneous or consecutive to the subject and in any order (e.g., the composition can be administered before or after the combination of VX-770/VX-809).

In some embodiments, the composition is stable at 2-8° C. for at least 72 hours. In some embodiments, the composition after storage at 2-8° C. for at least 72 hours comprises any one or more of the following: (a) essentially free of precipitation, (b) comprises less than 4% impurities, (c) has a pH of 6.0-7.0, and (d) minimal loss of solubility.

BRIEF DESCRIPTION OF THE DRAWINGS/FIGURES

FIGS. 5A-5C show the concentration of pro-inflammatory cytokines TNF-α (FIG. 5A), IL-6 (FIG. 5B), and IL-8 (FIG. 5C) secreted by human neutrophils following administration of lipoplysaccharide (LPS) and Composition 1.

FIG. 6 shows a cystic fibrosis transmembrane conductance receptor (CFTR) functional assay performed with wild-type cystic fibrosis bronchial epithelial cells (WT CFBE).

FIG. 9 shows metalloprotease-9 (MMP-9) release from LPS-stimulated neutrophils after one hour treatment with Composition 1 (Ar) at dilutions of 1:100 and 1:10 compared to media (Med) and LPS only controls. MMP-9 is the 75-100 kDa band on the gel.

Figure 10A:
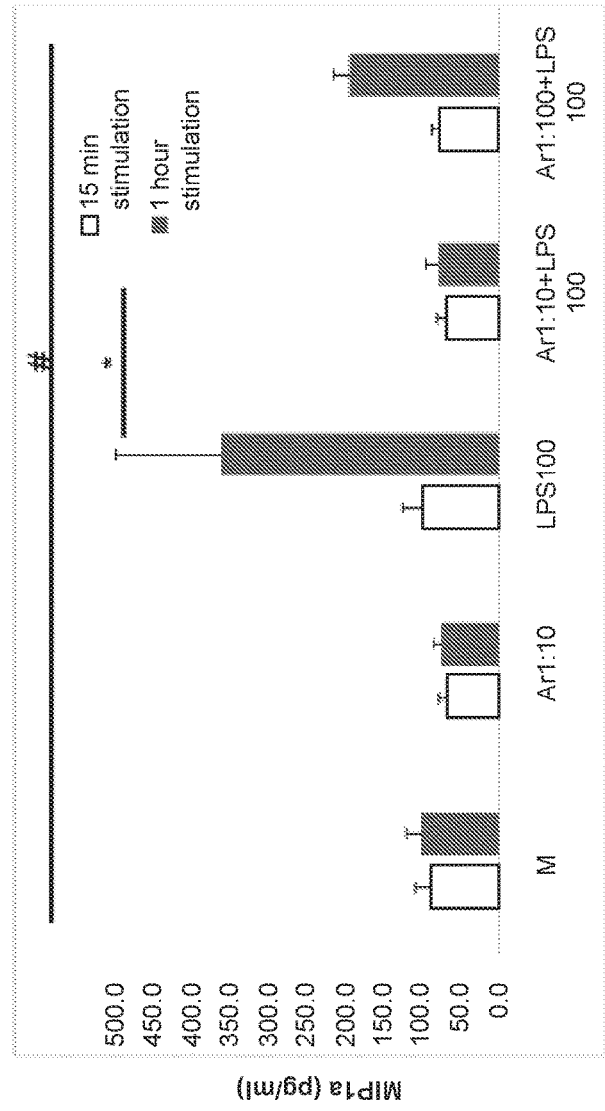
Figure 10B:
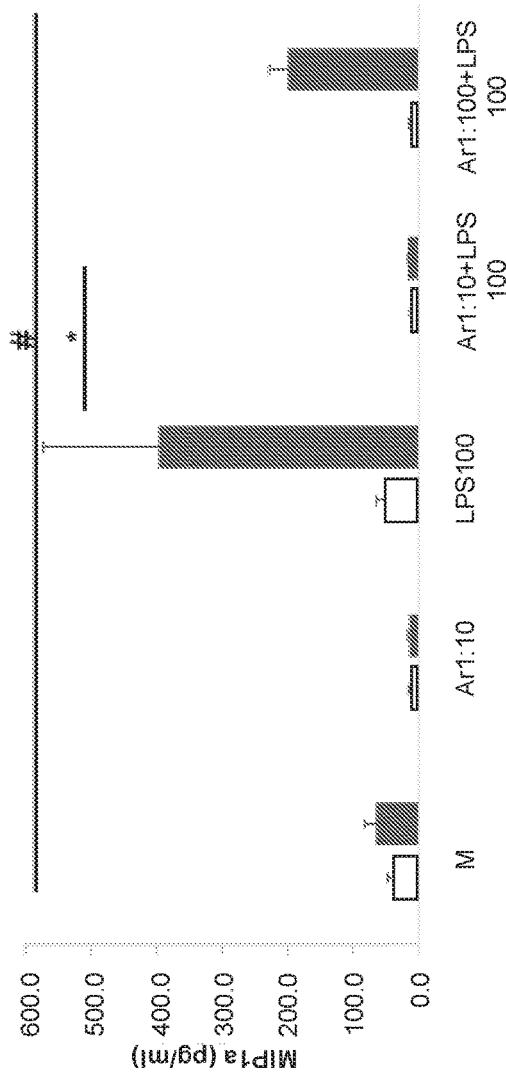

FIG. 10A-10B show neutrophil and macrophage-associated cytokines: macrophage inflammatory protein 1α (MIP1α) (FIG. 10A) and macrophage inflammatory protein 1β (MIP1β) (FIG. 10B) release levels from LPS-activated neutrophils after administration of Composition 1 (Ar) at dilutions of 1:100 and 1:10 compared to media (M) and LPS only controls. #ANOVA <0.01 for 1 hour. *p<0.05 LPS v. AR 1:10+LPS 100 via Tukey post-test.

FIG. 11 shows the affect of the combination of Composition 1 and VX-770/809 (COMP 1+VX-770/809, right panel) compared to PBS (left panel) and VX-770/809 alone (center panel) on the in vitro mucociliary transport (MCT) rate of primary human bronchial epithelial cells isolated from cystic fibrosis patients (dF508−/− cells).

Figure 12A:
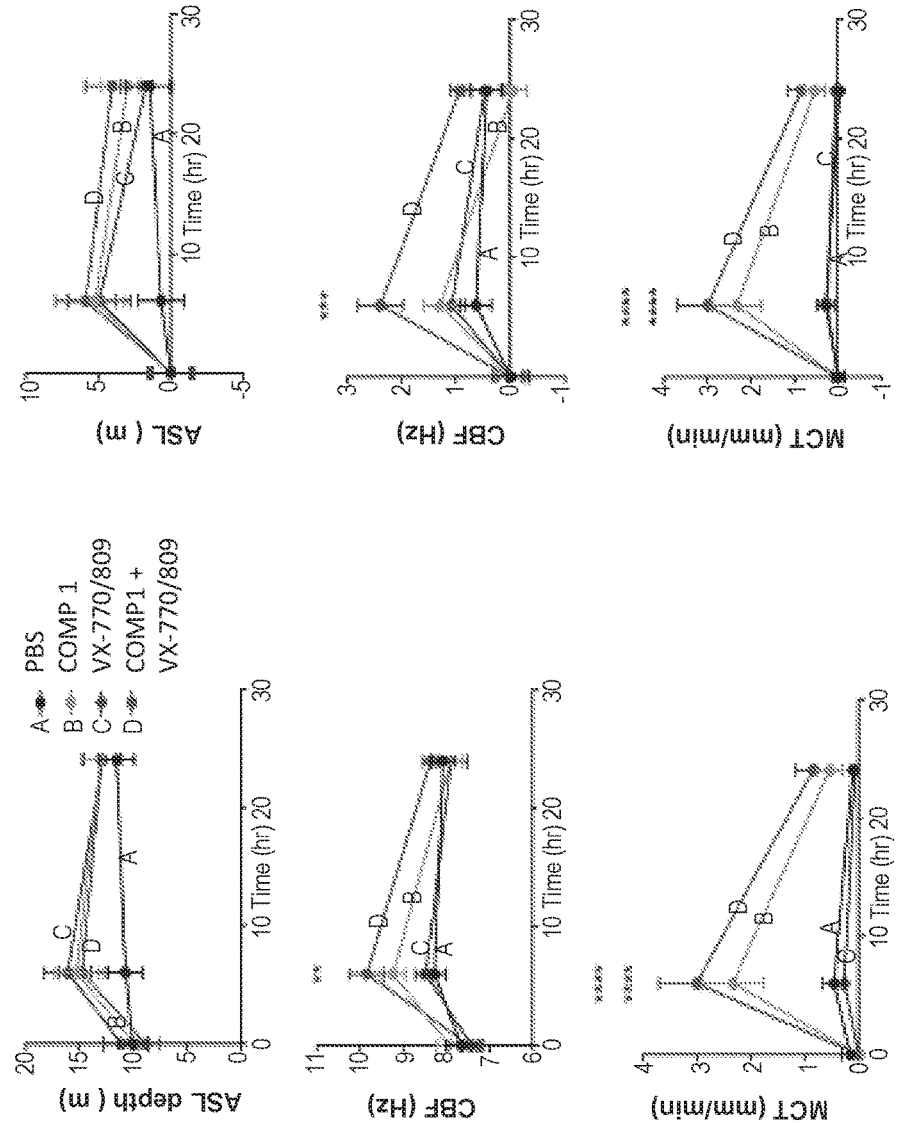

FIG. 12A shows a sample quantification of the airway surface liquid (ASL), ciliary beat frequency (CBF), and mucociliary transport (MCT) rate changes over time on dF508 CF HBE cells after administration of the combination of Composition 1 and VX-770/809 (COMP 1+VX-770/809), Composition 1 alone (COMP 1), VX-770/809 alone, or PBS control. Results show combined data (N=20 HBE monolayers across 3 CF donors homozygous for F508del). P<0.01, P<0.001, **P<0.0001.

FIG. 12B shows quantification of the mucociliary transport rate change from baseline vs. PBS (control) with Composition 1, VX-770/809, and a combination of Composition 1 with VX-770/809. Results show combined data (N=20 HBE monolayers across 3 CF donors homozygous for F508del). Mean±SEM ****P<0.0001.

Figure 13:
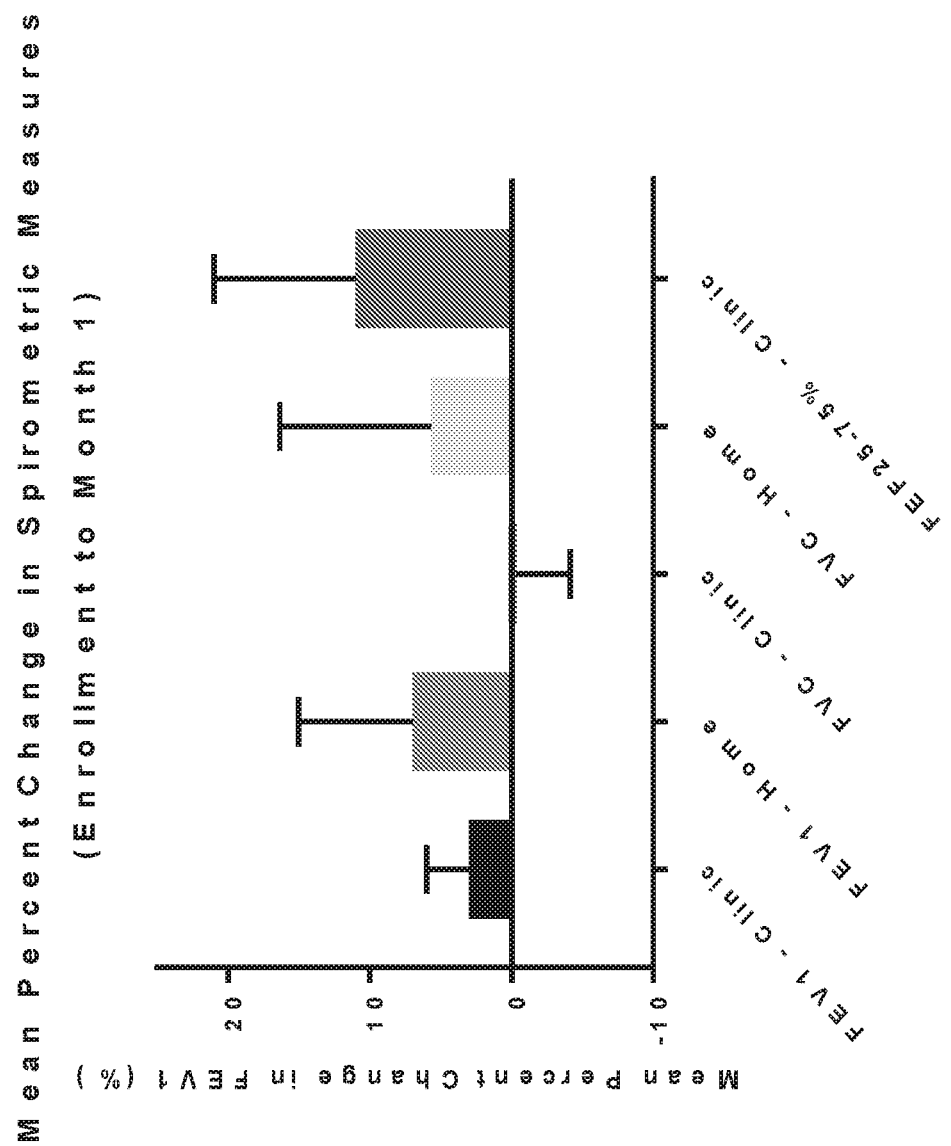

FIG. 13 shows mean percent change in spirometric measurements in patients post-lung transplant administered Composition 1 via nebulization for one month twice daily. The spirometric measurements include forced expiratory volume exhaled in one second (FEV1), forced vital capacity (volume) (FVC), and a measure of small-medium airway function (FEF25-75%). These results are after one month of treatment.

FIG. 14 shows percent change in fractional exhaled nitric oxide (FENO) in 4 patients post-lung transplant administered Composition 1 via nebulization for one month twice daily. CF, ILD, and A1AT refer to the background diseases of the patients (etiology of why they underwent transplant). These results are after one month of treatment.

FIG. 15 shows stability data after storage for about 72 hours at 2-8° C. for Formulations 1-9 having low, mid, or high concentrations of ascorbic acid and/or buffer. Glutathione (GSH) was the same concentration for each formulation. Composition 1 is shown as Formulation 9.

DETAILED DESCRIPTION

Definitions

To facilitate an understanding of the present invention, a number of terms and phrases are defined below.

As used in the present disclosure and claims, the singular forms "a," "an," and "the" include plural forms unless the context clearly dictates otherwise.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "about" as used herein means approximately ±10%. When the term "about" is used in conjunction with a numerical value or range, it modifies that value or range by extending the boundaries above and below the numerical values set forth. In general, the term "about" is used herein to modify a numerical value above and below the stated value by a variance of 10 percent, up or down (higher or lower), i.e., ±10%, unless a different variance is indicated (e.g., ±30%, ±20%, ±5%, ±1%, etc.).

"Clinical isolate bacteria" as used herein means a bacterial strain that has been isolated from a human subject or from a tissue sample taken from a human subject.

"Minimum inhibitory concentration" or "MIC" as used herein means the lowest concentration of an agent (e.g., an antibiotic and/or composition of the application) that will inhibit the visible growth of a bacteria species.

"Minimum bactericidal concentration" or "MBC" as used herein means the lowest concentration at which an agent (e.g., an antibiotic and/or composition of the application) will kill a bacteria species.

"Minimum biofilm eradication concentration" or "MBEC" as used herein means the lowest concentration of an agent (e.g., an antibiotic and/or composition of the application) that will inhibit the visible growth of a biofilm.

"Pharmaceutically acceptable" as used herein means safe and effective for use in humans. For example, a "pharmaceutically acceptable salt", as used herein, means those salts of the compounds disclosed herein that are safe and effective for use in a subject and that possess the desired biological activity of the compound.

"Biofilm" as used herein means a group of microorganisms, e.g., clinical isolate bacteria, in which cells of the microorganism stick to each other and often these cells adhere to a surface. In some embodiments, these adherent cells are embedded within a self-produced matrix of extracellular polymeric substance (EPS). In some embodiments, the biofilm comprises a single bacterial species. In other embodiments, the biofilm is a mixture of two or more species of bacteria.

"Mucoid bacteria" as used herein means alginate-producing bacteria.

"Nonmucoid bacteria" as used herein means bacteria that do not produce alginate.

"Aerobic" as used herein means an organism, e.g., bacteria that can survive and grow in an oxygenated environment.

"Anaerobic" or "anaerobe" as used herein means an organism, e.g., bacteria that do not require oxygen for growth. In some embodiments, the organism is an "obligate anaerobe", which means it is harmed by the presence of oxygen; an "aerotolerant organism", which means it cannot use oxygen for growth but tolerates its presence; or a "facultative anaerobe", which means it can grow without oxygen but will use oxygen if it is present.

"Extracellular" as used herein means outside a cell.

"Antibiotic resistance" refers to bacteria possessing a mechanism that makes an antibiotic ineffective at killing the bacteria. Exemplary mechanisms include, e.g., destruction of the antibiotic, antibiotic-target modification, and restricted penetration and/or efflux of the antibiotic. In some embodiments, the bacteria become antibiotic resistant due to a mutation.

"Multidrug resistance" (also referred to as "multiple drug resistance", "MDR", "multiresistance") as used herein means antimicrobial resistance shown by a species of microorganism, e.g., a species of bacteria, to multiple antimicrobial drugs, e.g., antibiotics.

"Antibiotic Tolerance" refers to specialized survivor (or persister) cells within a population of bacterial cells that are phenotypic variants (not mutants) that are non-growing dormant cells. Persisters are killed only slowly, if at all, by antibiotics and resume growth when antibiotic concentrations are lowered or stopped.

"Sensitized" as used herein means susceptibility of a microorganism, e.g., a bacteria, to an antimicrobial drug, e.g., an antibiotic.

"Synergistic effect" as used herein means an effect arising between two or more therapeutic agents, e.g., a composition disclosed herein and an antibiotic that produces an effect greater than the sum of the two or more therapeutic agent's individual effects.

"Inhibiting" as used herein means blocking or stopping, e.g., stopping bacterial growth.

"Reducing" as used herein means decreasing or lowering the amount of, e.g., lowering the amount of bacterial growth (e.g., as compared to a starting point or as compared between two or more groups).

"Treating" or "treatment" as used herein refers to partially or completely alleviating, ameliorating, improving, relieving, delaying onset of, inhibiting progression of, reducing severity of, and/or reducing incidence of one or more signs, symptoms or features of a disease.

By "subject" or "patient" is meant any subject, particularly a mammalian subject, for whom diagnosis, prognosis, or therapy is desired. In certain embodiments, the mammal is a human subject. In other embodiments, a subject is a human patient. In a particular embodiment, a subject is a human patient in need of treatment.

Administration "in combination with" one or more further therapeutic agents includes simultaneous (concurrent) or consecutive administration in any order.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered serially, by alternation, or in parallel as separate formulations; or (3) by some other regimen. When delivered in alternation therapy, a synergistic effect can be attained when the compounds are administered or delivered sequentially, e.g., by different injections in separate syringes or by inhalation of one therapy and oral administration of a second therapy or vice versa.

The term "pharmaceutical formulation" refers to a preparation which is in such form as to permit the biological activity of the active ingredient or active ingredients to be effective, and which contains no additional components which are unacceptably toxic to a subject to which the formulation would be administered. The formulation can be sterile.

An "effective amount" of a composition or active agent as disclosed herein is an amount sufficient to carry out a specifically stated purpose. An "effective amount" can be determined empirically and in a routine manner, in relation to the stated purpose.

The term "therapeutically effective amount" refers to an amount of composition or active agent as disclosed herein effective to "treat" a disease or disorder in a subject.

Glutathione and Glutathione Conjugate Compositions

In certain aspects, the compositions of the application comprise glutathione, a glutathione derivative, a glutathione conjugate, a pharmaceutically-acceptable salt thereof, or any combination thereof.

In some embodiments, the composition comprises glutathione or a pharmaceutically-acceptable salt thereof.

Glutathione or "GSH" refers to a compound having the Formula A:

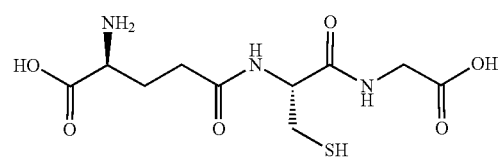 [SMILES: N[C@@H](CCC(=O)N[C@@H](CS)C(=O)NCC(=O)O)C(=O)O]

or a zwitterionic form thereof, e.g., a compound having the Formula B:

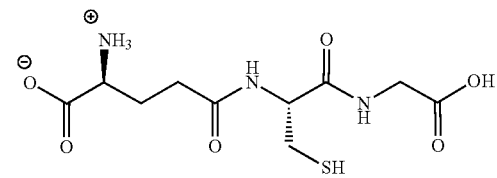 [SMILES: [NH3+][C@@H](CCC(=O)N[C@@H](CS)C(=O)NCC(=O)O)C(=O)[O-]]

Glutathione is the most abundant non-protein thiol in mammalian cells. It plays a role in the detoxification of xenobiotic compounds and in the antioxidation of reactive oxygen species and free radicals. See, e.g., Bray and Taylor, Canadian Journal of Physiology and Pharmacology 71:746-751 (1993).

In healthy individuals, there are high concentrations of GSH in the airway. However, in individuals with chronic inflammatory airway diseases, such as lung transplant patients, glutathione reserves are depleted.

In some embodiments, the composition comprises a glutathione-containing conjugate or a pharmaceutically-acceptable salt thereof. In certain embodiments, the glutathione-containing conjugate is metabolized to release glutathione, or a derivative thereof, upon administration to a subject. In some embodiments, the glutathione-containing conjugate is referred to herein as a "Conjugate Compound of the Disclosure" or "glutathione conjugate."

In one embodiment, a Conjugate Compound of the Disclosure is a compound having Formula I:

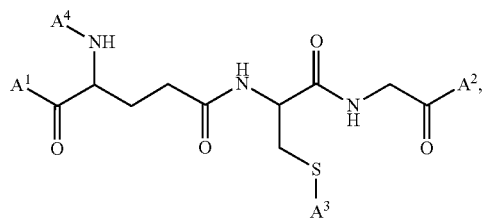

I and the pharmaceutically acceptable salts and solvates thereof, wherein, $A^1$ is —$OR^1$; $A^2$ is $Z^1$; $A^3$ is hydrogen; and $A^4$ is $R^{3a}$; or $A^1$ is $Z^1$; $A^2$ is —$OR^2$; and $A^3$ is hydrogen; and $A^4$ is $R^{3a}$; or $A^1$ is —OR % $A^2$ is —$OR^2$; and $A^3$ is $Z^3$; and $A^4$ is $R^{3a}$; or $A^1$ is $Z^2$; $A^2$ is —$OR^2$; and $A^3$ is hydrogen; and $A^4$ is $R^{3a}$; or $A^1$ is —$OR^1$; $A^2$ is $Z^2$; and $A^3$ is hydrogen; and $A^4$ is $R^{3a}$; or $A^1$ is —OR'; $A^2$ is —$OR^2$; $A^3$ is hydrogen; and $A^4$ is $Z^3$; or $A^1$ and $A^2$ are each $Z^1$, and $A^3$ is hydrogen;

$Z^1$ is selected from the group consisting of:

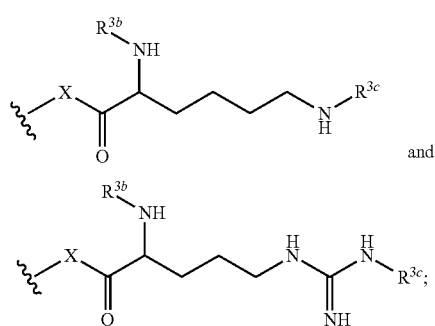

and $Z^2$ is selected from the group consisting of:

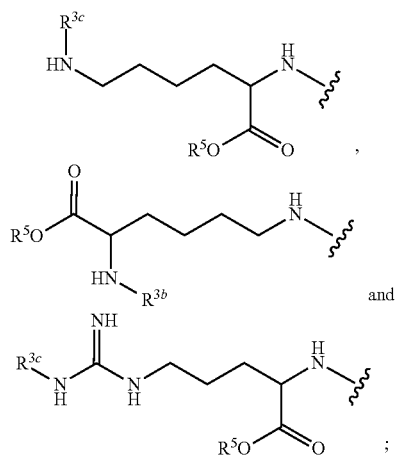

and

;

$Z^3$ is selected from the group consisting of:

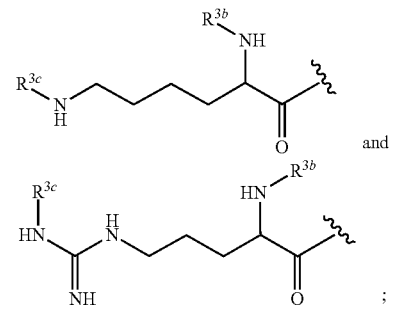

and

;

$R^1$ is selected from the group consisting of hydrogen and optionally substituted alkyl;
$R^2$ is selected from the group consisting of hydrogen and optionally substituted alkyl;
$R^{3a}$, $R^{3b}$, and $R^{3c}$ are each independently selected from the group consisting of hydrogen and protecting group;
X is selected from the group consisting of:
—O—;
—O(CH$_2$)$_m$O—;
—OCH$_2$CH(R$^4$)O—;
—OCH(R$^4$)CH$_2$O—; and
—O(CH$_2$CH$_2$O)$_n$—;
$R^4$ is:

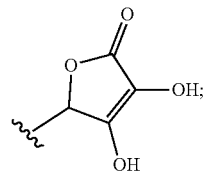

m is 1, 2, 3, 4, 5, 6, 7, or 8;
n is 2, 3, 4, 5, 6, 7, or 8; and
$R^5$ is selected from the group consisting of hydrogen and optionally substituted alkyl.

In another embodiment, a Conjugate Compound of the Disclosure is a compound having Formula I, and the pharmaceutically acceptable salts and solvates thereof, wherein m is 2, 3, 4, 5, 6, 7, or 8.

In another embodiment, a Conjugate Compound of the Disclosure is a compound having Formula II:

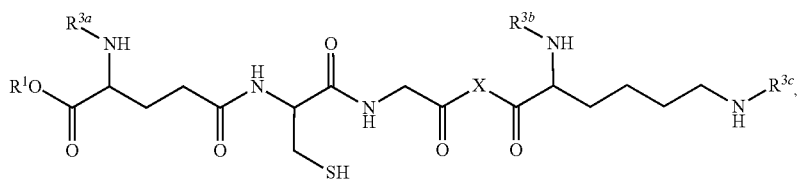

II or a pharmaceutically acceptable salt or solvate thereof, wherein R1, R3a, R3b, R3c, and X are as defined in connection with Formula I.

In another embodiment, a Conjugate Compound of the Disclosure is an enantiomerically enriched compound having any one or more of formulae of Table 1, and the pharmaceutically acceptable salts and solvates thereof, wherein $R^1$, $R^{3a}$, $R^{3b}$, $R^{3c}$, and X are as defined in connection with Formula I.

Compositions of the Disclosure

Glutathione, a glutathione derivative, a glutathione conjugate, a pharmaceutically-acceptable salt thereof, organic acid, or any combination thereof can be admixed with a pharmaceutical carrier, e.g., water, and, optionally, other components to give a "Composition of the Disclosure." In some embodiments, the amount of glutathione, a glutathione derivative, a glutathione conjugate, pharmaceutically-acceptable salt thereof, or any combination thereof, e.g., reduced glutathione, in the Composition of the Disclosure is about 30-90% by weight, about 30-85% by weight, about 30-80% by weight, about 30-75% by weight, about 30-70% by weight, about 30-65% by weight, about 30-60% by weight, about 30-55% by weight, about 30-50% by weight. In some embodiments, the amount of glutathione, a glutathione derivative, a glutathione conjugate, pharmaceutically-acceptable salt thereof, or any combination thereof, e.g., reduced glutathione, in the Composition of the Disclosure is 30-50% by weight.

In some embodiments, the Composition of the Disclosure further comprises an organic acid. In some embodiments, the organic acid is selected from the group of acids consisting of ascorbic, acetic, adipic, aspartic, benzenesulfonic, benzoic, butyric, camphorsulfonic, camsylic, carbonic, chlorobenzoic, cholic, citric, edetic, edisylic, estolic, ethanesulfonic, formic, fumaric, gluceptic, gluconic, glucuronic, glutamic, glycolic, glycolylarsanilic, hippuric, 1-hydroxy-2-naphthoic, isethionic, isobutyric, isonicotinic, lactic, lactobionic, maleic, malic, malonic, mandelic, methanesulfonic, mucic, muconic, napthalenesulfonic, nicotinic, oxalic, oleic, orotic, p-nitromethanesulfonic, pamoic, pantothenic, phthalic, polygalactouronic, propionic, saccharic, salicylic, stearic, suberic, succinic, sulfanilic, tannic, tartaric, p-toluenesulfonic and any combination thereof. In some embodiments, the amount of organic acid, e.g., reduced ascorbic acid, in the Composition of the Disclosure is about 10-90% by weight, about 10-85% by weight, about 10-80% by weight, about 10-75% by weight, about 10-70% by weight, about 10-65% by weight, about 10-60% by weight, about 10-55% by weight, about 10-50% by weight, about 10-45% by weight, about 10-40% by weight, about 10-35% by weight, about 10-30% by weight, about 1-30% by weight, about 1-20% by weight, or about 1-10% by weight. In some embodiments, the amount of organic acid, e.g., reduced ascorbic acid, in the Composition of the Disclosure is 25-40% by weight.

In some embodiments, the Composition of the Disclosure further comprises a bicarbonate salt. In some embodiments, the bicarbonate salt is sodium bicarbonate. In some embodiments, the amount of bicarbonate salt, e.g., sodium bicarbonate, in the Composition of the Disclosure is about 10-90% by weight, about 10-85% by weight, about 10-80% by weight, about 10-75% by weight, about 10-70% by weight, about 10-65% by weight, about 10-60% by weight, about 10-55% by weight, about 10-50% by weight, about 10-45% by weight, about 10-40% by weight, about 10-35% by weight, about 10-30% by weight, about 1-30% by weight, about 1-20% by weight, or about 1-10% by weight. In some embodiments, the amount of bicarbonate salt, e.g., sodium bicarbonate, in the Composition of the Disclosure is about 20-30% by weight. In some embodiments, the Composition of the Disclosure does not comprise a bicarbonate salt.

In some embodiments, the pH of the Composition of the Disclosure is about 6.0 to about 8. In some embodiments, the pH of the Composition of the Disclosure is greater than 5.5 or at least 6.0. (e.g., 5.6 to 14, 5.7 to 14, 5.8 to 14, 5.9 to 14, 6 to 14, 5.6 to 12, 5.7 to 12, 5.8 to 12, 5.9 to 12, 6 to 12, 5.6 to 10, 5.7 to 10, 5.8 to 10, 5.9 to 10, 6 to 10, 5.6 to 9, 5.7 to 9, 5.8 to 9, 5.9 to 9, 6 to 9, 5.6 to 8, 5.7 to 8, 5.8 to 8, 5.9 to 8, 6 to 8, 5.6 to 7.5, 5.7 to 7.5, 5.8 to 7.5, 5.9 to 7.5, 6 to 7.5, 5.6 to 7, 5.7 to 7, 5.8 to 7, 5.9 to 7, or 6 to 7).

In some embodiments, the Composition of the Disclosure is formulated to maximize formulation stability and minimize oxidation of glutathione. Oxidized glutathione is associated with the generation of protein-carbonyls via glutathionlyation. Glutathionylation occurs when oxidized glutathione dissociates and attaches to proteins. Maintaining the glutathione in the reduced state in solution prior to administration can decrease the risk of glutathionylation products that can result in clinical complications such as bronchiectasis. In some embodiments, the oxidized glutathione (e.g., % GSSG) in the Composition of the Disclosure is less than about 20%, less than about 18%, less than about 16%, less than about 15%, less than about 12%, less than about 10%, less than about 9%, less than about 8%, less than about 7%, less than about 6%, less than about 5%, less than about 4%, or less than about 3% by weight of the total glutathione in the Composition of the Disclosure after storage of the Composition of the Disclosure for 4 weeks (e.g., at 5° C. in a $N_2$ atmosphere and/or ambient atmosphere). In some embodiments, the percentage of oxidized glutathione (e.g., % GSSG) in the Composition of the Disclosure is no more than about 2% to about 20%, about 2% to about 18%, about 2% to about 16%, about 2% to about 16%, about 2% to about 10%, or about 2% to 8% by weight of the total glutathione in the Composition of the Disclosure following 4 weeks of storage (e.g., at 5° C. in a $N_2$ atmosphere and/or ambient atmosphere). In some embodiments, the percentage of oxidized glutathione (e.g., % GSSG) in the Composition of the Disclosure is less than about 20%, less than about 18%, less than about 16%, or less than about 10% by weight of the total glutathione in the Composition of the Disclosure following 4 weeks of storage (e.g., at 5° C. in a $N_2$ atmosphere and/or ambient atmosphere).

In some embodiments, the reduced glutathione in the Composition of the Disclosure is more than about 80%, more than about 82%, more than about 84%, more than about 85%, more than about 88%, more than about 90%, more than about 91%, more than about 92%, more than about 93%, more than about 94%, more than about 95%, more than about 96%, or more than about 97% by weight of the total glutathione in the Composition of the Disclosure after storage of the Composition of the Disclosure for 4 weeks at about 5° C. (e.g., in a $N_2$ or ambient atmosphere). In some embodiments, the percentage of reduced glutathione in the Composition of the Disclosure is between about 80% to about 100%, between about 80% to about 98%, between about 82% to about 98%, between about 84% to about 98%, between about 86% to about 98%, between about 88% to about 98%, between about 90% to about 98%, or between about 92% to to about 98% by weight of the total glutathione in the Composition of the Disclosure following 4 weeks of storage at 5° C. (e.g., in a $N_2$ or ambient atmosphere). In some embodiments, the percentage of reduced glutathione in the Composition of the Disclosure is at least 80%, at least 82%, at least 84%, at least 86%, at least 88%, or at least 90% by weight of the total glutathione in the Composition of the Disclosure following 4 weeks of storage at 5° C. in a $N_2$ or ambient atmosphere.

In some embodiments, the Composition of the Disclosure is further formulated to maximize formulation stability and minimize oxidation of organic acid, e.g., ascorbic acid. Additionally, when ascorbic acid is oxidized into dehydroascorbate (DHA), DHA can break down and result in the formation of protein adducts in process called ascorbylation. Maintaining the organic acid, e.g., ascorbic acid, in the reduced state in solution prior to administration can decrease the risk of ascorbylation from the breakdown products of dehydroascorbate. In some embodiments, the reduced ascorbic acid (e.g., % ASC) is more than about 80%, more than about 85%, more than about 86%, more than about 87%, more than about 88%, more than about 89%, or more than about 90% by weight of the ascorbic acid in the Composition of the Disclosure after storage of the Composition of the Disclosure for 4 weeks (e.g., at 5° C. in a $N_2$ atmosphere and/or ambient atmosphere). In some embodiments, the percentage of reduced ascorbic acid (e.g., % ASC) in the Composition of the Disclosure is between about 82% to about 100% or between about 85% to about 95% by weight of the total ascorbic acid in the Composition of the Disclosure following 4 weeks of storage (e.g., at 5° C. in a $N_2$ atmosphere and/or ambient atmosphere). In some embodiments, the percentage of reduced ascorbic acid (e.g., % ASC) in the Composition of the Disclosure is at least 80%, at least 85%, at least 86%, at least 87%, at least 88%, at least 89%, or at least 90% by weight of the total ascorbic acid in the Composition of the Disclosure following 4 weeks of storage (e.g., at 5° C. in a $N_2$ atmosphere and/or ambient atmosphere).

In some embodiments, the oxidized ascorbic acid in the Composition of the Disclosure is less than about 20%, less than about 18%, less than about 16%, less than about 15%, less than about 12%, less than about 10%, or less than about 9% by weight of the total ascorbic acid in the Composition of the Disclosure after storage of the Composition of the Disclosure for 4 weeks (e.g., at 5° C. in a $N_2$ atmosphere and/or ambient atmosphere). In some embodiments, the percentage of oxidized ascorbic acid in the Composition of the Disclosure is no more than about 5% to about 20%, about 5% to about 18%, about 5% to about 10%, or about 5% to 9% by weight of the total ascorbic acid in the Composition of the Disclosure following 4 weeks of storage (e.g., at 5° C. in a $N_2$ atmosphere and/or ambient atmosphere). In some embodiments, the percentage of oxidized ascorbic acid in the Composition of the Disclosure is less than about 20%, less than about 18%, less than about 16%, or less than about 10% by weight of the total ascorbic acid in the Composition of the Disclosure following 4 weeks of storage (e.g., at 5° C. in a $N_2$ atmosphere and/or ambient atmosphere).

In certain aspects, the ratios of the components of the Composition of the Disclosure are formulated to maximize formulation stability and minimize oxidation of glutathione and organic acid, e.g., ascorbic acid. In some embodiments, glutathione and organic acid (e.g., ascorbic acid) are formulated to comprise molar equivalents in solution, e.g., about 0.5-1:1, about 0.6-1:1, 0.7-1:1, 0.8-1:1, 0.9-1:1 or about 1:1 molar ratio of glutathione to ascorbic acid. In some embodiments, the glutathione and organic acid (e.g., ascorbic acid) are formulated to comprise molar excess of organic acid (e.g., ascorbic acid) relative to glutathione in solution, e.g., about 1:1.1, about 1:1.2, about 1:3, about 1:4, about 1:5 molar ratio of glutathione to ascorbic acid.

In some embodiments, the Composition of the Disclosure further comprises a bicarbonate salt (e.g., sodium bicarbonate). In some embodiments, glutathione, organic acid (e.g., ascorbic acid), and bicarbonate salt (e.g., sodium bicarbonate) are formulated to comprise a molar ratio of about 0.1-0.5:0.5-1:1, about 0.2-0.5:0.5-1:1, about 0.3-0.5:0.5-1:1, about 0.4-0.5:0.5-1:1, about 0.49:0.5-1:1, about 0.5:0.5-1:1, about 0.1-0.5:0.6-1:1, about 0.2-0.5:0.6-1:1, about 0.3-0.5:0.6-1:1, about 0.4-0.5:0.6-1:1, about 0.49:0.6-1:1, about 0.5:0.6-1:1, about 0.1-0.5:0.7-1:1, about 0.2-0.5:0.7-1:1, about 0.3-0.5:0.7-1:1, about 0.4-0.5:0.7-1:1, about 0.49:0.7-1:1, about 0.5:0.7-1:1, about 0.1-0.5:0.8-1:1, about 0.2-0.5:0.8-1:1, about 0.3-0.5:0.8-1:1, about 0.4-0.5:0.8-1:1, about 0.49:0.8-1:1, about 0.5:0.8-1:1, about 0.1-0.5:0.9-1:1, about 0.2-0.5:0.9-1:1, about 0.3-0.5:0.9-1:1, about 0.4-0.5:0.9-1:1, about 0.49:0.9-1:1, about 0.5:0.9-1:1, about 0.1-0.5:1:1, about 0.2-0.5:1:1, about 0.3-0.5:1:1, about 0.4-0.5:1:1, about 0.49:1:1, about 0.5:1:1, molar ratio of glutathione to organic acid (e.g., ascorbic acid) to bicarbonate salt (e.g., sodium bicarbonate). In some embodiments, the molar ratio of glutathione, organic acid (e.g., ascorbic acid), and bicarbonate salt (e.g., sodium bicarbonate) is 0.1-0.5:0.5-1:1, 0.4-0.5:0.5-1:1, 0.1-0.5:0.5:1, 0.1-0.5:1:1, or 0.4-0.5:1:1. In some embodiments, the molar ratio of glutathione, organic acid (e.g., ascorbic acid), and bicarbonate salt (e.g., sodium bicarbonate) is 0.49:0.5:1, 0.5:0.5:1, 0.49:1:1, or 0.5:1:1.

In some embodiments, the bicarbonate salt (e.g., sodium bicarbonate) is less than the combined molar ratio of (a) glutathione, a glutathione derivative, a glutathione conjugate, a pharmaceutically-acceptable salt thereof, or any combination thereof and (b) organic acid (e.g., ascorbic acid). In some embodiments, the molar ratio of glutathione, organic acid (e.g., ascorbic acid), and bicarbonate salt (e.g., sodium bicarbonate) is 0.1-0.49:0.5:1, 0.2-0.49:0.5:1, 0.3-0.49:0.5:1, or 0.4-0.49:0.5:1.

In some embodiments, Composition of the Disclosure comprises or consists essentially of (a) a glutathione, a glutathione derivative, a glutathione conjugate, pharmaceutically-acceptable salt thereof, or any combination thereof, and (b) an organic acid, wherein the molar ratio of (a) to (b) is about 0.5-1:1, about 0.6-1:1, 0.7-1:1, 0.8-1:1, 0.9-1:1 or about 1:1 and the pH of the composition is about 5.5 to 14, about 6 to about 8, 7±1.5, 6±0.5, or about 6.

In some embodiments, Composition of the Disclosure comprises or consists essentially of (a) a glutathione, a glutathione derivative, a glutathione conjugate, pharmaceutically-acceptable salt thereof, or any combination thereof, (b) an organic acid, (c) a bicarbonate salt, wherein the molar ratio of (a) to (b) to (c) is about 0.1-0.5:0.5-1:1, 0.4-0.5:0.5-1:1, 0.1-0.5:0.5:1, 0.1-0.5:1:1, 0.4-0.5:1:1, 0.1-0.49:0.5:1, 0.2-0.49:0.5:1, 0.3-0.49:0.5:1, or 0.4-0.49:0.5:1 and the pH of the composition is about 5.5 to 14, about 6 to about 8, 7±1.5, 6±0.5, or about 6.

Pharmaceutical compositions for use in the present disclosure can be formulated using one or more physiologically acceptable carriers and/or excipients that facilitate administration of organic acid, glutathione, a glutathione derivative, a glutathione conjugate, a pharmaceutically-acceptable salt thereof, or any combination thereof to a subject by an intended route, e.g., delivery by inhalation. In some embodiments, the pharmaceutical composition is an aqueous solution. In some embodiments, the pharmaceutical composition is a dry powder.

Compositions of the Disclosure can be manufactured by conventional mixing, dissolving, granulating, dragee-making, emulsifying, encapsulating, entrapping, spray drying, or lyophilizing processes that are known in the art. The particular formulation depends upon the route of administration chosen. In one embodiment, glutathione, a glutathione derivative, a glutathione conjugate, a pharmaceutically-acceptable salt thereof, or any combination thereof is dissolved in a solvent, e.g., water, for administration to the airway of a subject (e.g., intranasal administration).

The term "pharmaceutically acceptable carrier" refers to a pharmaceutically-acceptable material, composition, or vehicle, such as a liquid (e.g., water), or a solid filler, diluent, excipient, solvent, or encapsulating material. A carrier is "pharmaceutically acceptable" in the sense of being compatible with the other ingredients of a pharmaceutical formulation and suitable for use in humans without toxicity, irritation, allergic response, immunogenicity, or other complications commensurate with a reasonable benefit/risk ratio. See, Remington: The Science and Practice of Pharmacy, 21st Edition; Lippincott Williams & Wilkins: Philadelphia, Pa., 2005; Handbook of Pharmaceutical Excipients, 5th Edition; Rowe et al., Eds., The Pharmaceutical Press and the American Pharmaceutical Association: 2005; and Handbook of Pharmaceutical Additives, 3rd Edition; Ash and Ash Eds., Gower Publishing Company: 2007; Pharmaceutical Preformulation and Formulation, Gibson Ed., CRC Press LLC: Boca Raton, Fla., 2004).

In some embodiments, Compositions of the Disclosure comprise an excipient. In some embodiments, the excipient is selected from the group consisting of a pH adjusting agent, a preservative, a chelating agent, and any combination thereof.

In certain embodiments, the Compositions of the Disclosure can comprise a pH adjusting agent. pH adjusting agents are known in the art See, e.g., Remington's Pharmaceutical Sciences, 18th edition, A. R Gennaro, Ed., Mack Publishing Company (1990) and Handbook of Pharmaceutical Excipients, 3rd edition, A. Kibbe, Ed., Pharmaceutical Press (2000). Suitable examples of pharmaceutically acceptable pH adjusting agents include, but are not limited to, ascorbic acid, citric acid, sodium citrate, sodium bicarbonate, potassium bicarbonate, dibasic sodium phosphate, magnesium oxide, calcium carbonate, magnesium hydroxide, buffers (e.g., acetate buffers, citrate buffers, phosphate buffers, lactic acid buffers, and borate buffers, and any combination thereof), fat-soluble fatty acid esters of ascorbic acid (vitamin C) (e.g., alone or in combination with a-hydroxy acids), oxidation-resistant saturated fatty acid esters of ascorbic acid (e.g., ascorbyllaurate, ascorbyl myristate, ascorbyl palmitate, ascorbyl stearate, and ascorbyl behenate, and any combination thereof), and any combination thereof. In some embodiments, esters can be prepared using hydrogenated oils or fats, or fractions thereof, and contain small amounts of another ester. Ascorbyl stearate prepared using canola, for example, can commonly contain about 4% ascorbyl palmitate.

In one embodiment, the pH adjusting agent, e.g., ascorbic acid, is present in a Composition of the Disclosure in an amount of about 0.01-50% by weight, about 10-90% by weight, about 10-85% by weight, about 10-80% by weight, about 10-75% by weight, about 10-70% by weight, about 10-65% by weight, about 10-60% by weight, about 10-55% by weight, about 10-50% by weight, about 10-45% by weight, about 10-40% by weight, about 10-35% by weight, about 10-30% by weight, about 1-30% by weight, about 1-20% by weight, or about 1-10% by weight. In some embodiments, the pH adjusting agent is present in a Composition of the Disclosure at an amount of about 1% by weight, about 5% by weight, about 10% by weight, about 15% by weight, about 20% by weight, about 25% by weight, about 30% by weight, about 35% by weight, about 40% by weight, about 45% by weight, or about 50% by weight of the composition.

In certain embodiments, the Compositions of the Disclosure can comprise preservatives. Pharmaceutically acceptable preservatives include, but are not limited to, various antibacterial and antifungal agents, solvents (e.g., ethanol, propylene glycol, benzyl alcohol and chlorobutanol, and any combination thereof), quaternary ammonium salts (e.g., cetylypridinium chloride, benzalkonium chloride and parabens including, but not limited to, methyl paraben, ethyl paraben and propyl paraben), chlorhexidine, benzoic acid and the salts thereof, parahydroxybenzoic acids and the salts thereof, alkyl esters of parahydroxybenzoic acid and the salts thereof, phenylmercuric salts such as nitrate, chloride, acetate, and borate, antioxidants, EDTA, sorbitol, phenol, boric acid and the salts thereof, sorbic acid and the salts thereof, thimerosal and nitromersol, and any combinations thereof.

In one embodiment, the preservative is present in a Composition of the Disclosure in about 0.01-50% by weight, e.g., about 1-30% by weight, about 1-20% by weight, or about 1-10% by weight, e.g., about 1% by weight, about 5% by weight, about 10% by weight, about 15% by weight, about 20% by weight, about 25% by weight, about 30% by weight, about 35% by weight, about 40% by weight, about 45% by weight, or about 50% by weight of the composition.

In certain embodiments, the Compositions of the Disclosure can comprise a chelating agent. Non-limiting examples of chelating agents include lactic acid, acetic acid, oxalic acid, malonic acid, succinic acid, maleic acid, fumaric acid, aconitic acid, pimelic acid, sebacic acid, allymalonic acid, ethylmalonic acid, citric acid, malic acid, glyceric acid, tartaric acid, mevaloic acid, oxyglutaric acid, oxaloacetic acid, a-ketoglutaric acid, a-ketomalonic acid, glucuronic acid, galaceturonic acid, mannuronic acid, aspartic acid, glutamic acid, glycine, alanine, lysine, histidine, alginine, cysteine, s-aminocaproic acid, phenylalanine, phenylglycine, p-hydroxyphenylglycine, p-aminophenylalanine, y-carboxyglutamic acid, iminodiacetic acid, hydroxyethyliminodiacetic acid, ethylenediaminediacetic acid, ethylenediaminetetraacetic acid, trans-cyclohexane-diaminetetraacetic acid, diethylenediaminepentaacetic acid, alaninediacetic acid, diaminopimelic acid, phthalic acid, terephthalic acid, homophthalic acid, phenylsuccinic acid, phenylmalonic acid, oxanylic acid-o-carboxylic acid, anthralininoacetic acid, 2,4-dihydroxybenzoic acid, p-aminosalicyclic acid, phthalyglutamic acid, kynurenine, 1,2-hyroxybenzene-3,5-disulfonic acid, 4-amino-phenol-2-sulfonic acid, cysteic acid, 2-phosphoglyceric acid, glycero-3-phosphoric acid, glucose-1,6-diphosphoric acid, fructose-1,6-diphosphoric acid and phosphates (e.g., sodium phosphate, sodium aluminum phosphate, sodium acid phosphate, dipotassium phosphate, disodium phosphate, monobasic and sodium hexametaphosphate), and any combination thereof. Chelating agents can be included in the pharmaceutical compositions of this disclosure either as the parent molecule or in the salt form where appropriate. For example, compounds containing an acid function can be used in the protonated form or as a pharmaceutically acceptable inorganic or organic salt which retains the chelating activity of the parent compound In one embodiment, the chelating agent is present in a Composition of the Disclosure in about 0.01-50% by weight, e.g., about 1-30% by weight, about 1-20% by weight, or about 1-10% by weight, e.g., about 1% by weight, about 5% by weight, about 10% by weight, about 15% by weight, about 20% by weight, about 25% by weight, about 30% by weight, about 35% by weight, about 40% by weight, about 45% by weight, or about 50% by weight of the composition.

In certain embodiments, the Composition of the Disclosure comprises glutathione, a glutathione derivative, a glutathione conjugate, a pharmaceutically-acceptable salt thereof, or any combination thereof; a bicarbonate (e.g., sodium bicarbonate or potassium bicarbonate) and/or a pH modifier (e.g., ascorbic acid). In some embodiments, the Composition of the Disclosure comprises glutathione, a glutathione derivative, a glutathione conjugate, a pharmaceutically-acceptable salt thereof, or any combination thereof and/or a pH modifier such as an organic acid (e.g., ascorbic acid). In some embodiments, the composition claimed wherein the amount of each component is present such that the amount of ascorbic acid is approximately molar equivalent or in molar excess of that of glutathione, a glutathione derivative, a glutathione conjugate, a pharmaceutically-acceptable salt thereof, or any combination thereof.

In some embodiments, a Composition of the Disclosure comprises (a) glutathione, a glutathione derivative, a glutathione conjugate, a pharmaceutically-acceptable salt thereof; (b) an organic acid; and (c) a bicarbonate salt. In further embodiments, the molar ratio of (a):(b):(c) in a Composition of the Disclosure is 0.1-0.5:0.5-1:1 (e.g., 0.4-0.5:0.5-1:1, 0.1-0.5:0.5:1, 0.1-0.5:1:1, 0.4-0.5:1:1, 0.1-0.49:0.5:1, 0.2-0.49:0.5:1, 0.3-0.49:0.5:1, or 0.4-0.49:0.5:1).

In some embodiments, the organic acid in a Compositon of the Disclosure is ascorbic acid. In some embodiments, the bicarbonate salt in a Composition of the Disclosure is sodium bicarbonate. In some embodiments, the composition comprises: (a) glutathione; (b) ascorbic acid; and (c) sodium bicarbonate. In certain embodiments, the molar ratio of (a):(b):(c) is about 0.1-0.5:0.5-1:1 (e.g., about 0.49:about 0.50:about 1). In other embodiments, the molar ratio of (a):(b):(c) is about 0.1-0.5:1:1 (e.g., about 0.49:about 1:about 1).

In some embodiments, the pH of a Composition of the Disclosure is from about 5.5 to about 14 (e.g. 5.5 to 7.5). In some embodiments, the pH of a Composition of the Disclosure is from about 6 to about 14 (e.g., 6 to 7.5). In some embodiments, the pH of the composition is 7±1.5, 7±1.4, 7±1.3, 7±1.2, 7±1.1, 6±0.5, 6±0.4, 6±0.3, 6±0.2, 6±0.5, 6±0.1, or about 6.

In some embodiments, the Composition of the Disclosure is storage stable at 2-8° C. for at least 72 hours. In some embodiments, the Composition of the Disclosure can (a) remain essentially free of precipitation after storage at 2-8° C. for at least 72 hours, (b) comprise less than 7%, less than 6%, less than 5%, or less than 4% impurities after storage at 2-8° C. for at least 72 hours, (c) have or maintain a pH from about 6 to 7.5 (e.g., 6.0-7.0) after storage at 2-8° C. for at least 72 hours, and/or (d) have minimal loss of solubility after storage at 2-8° C. for at least 72 hours.

Methods of Use

In some embodiments, the Compositions of the Disclosure are useful for treating, reducing the symptoms of, or preventing a disease, condition, or disorder of the lung. In particular, Compositions of the Disclosure can be used to inhibit or reduce the growth clinical isolate bacteria and/or to inhibit or reduce the formation of a clinical isolate bacteria biofilm. Compositions of the Disclosure can be used to treat or reduce the symptoms in a subject suffering from or at risk of a clinical isolate bacteria infection. In other embodiments, Compositions of the Disclosure are useful for upregulating mucociliary clearance in a subject suffering from or at risk of impaired mucociliary clearance, e.g., in a subject with our without an active bacterial infection in the lung. In other embodiments, Compositions of the Disclosure are useful for reducing airway inflammation in a subject suffering from or at risk of airway inflammation, e.g., with our without an active bacterial infection lung.

In some embodiments, the subject has a pulmonary or airway disease or disorder. In some embodiments, the pulmonary or airway disorder is selected from the group consisting of chronic inflammatory lung disease, pulmonary fibrosis, pulmonary vasculitis, pulmonary sarcoidosis, inflammation and/or infection associated with lung transplantation, acute or chronic lung rejection and/or dysfunction, pulmonary artery hypertension, bronchitis, sinusitis, asthma, cystic fibrosis, bronchiectasis (e.g., non-cystic fibrosis bronchiectasis or cystic fibrosis bronchiectasis), bacterial infection, fungal infection, parasite infection, viral infection, chronic obstructive pulmonary disease (COPD), bronchiolitis obliterans syndrome (BOS), primary ciliary dyskinesia (PCD), alveolar protienosis, idiopathic pulmonary fibrosis, eosinophilic pneumonia, eosinophilic bronchitis, acute respiratory distress syndrome (ARDS), inflammation and/or infection associated with mechanical ventilation, ventilator-associated pneumonia, asbestos-related airway disorder or disease, dust-related airway disorder or disease, silicosis, and radiation or chemical agent-related airway disease or disorder, and any combination thereof.

In some embodiments, the pulmonary or airway disease or disorder is selected from the group consisting of chronic inflammatory lung disease, an inflammation and/or infection associated with lung transplantation, acute or chronic lung rejection or dysfunction, asthma, cystic fibrosis, bronchiectasis (e.g., non-cystic fibrosis bronchiectasis or cystic fibrosis bronchiectasis), or chronic obstructive pulmonary disease (COPD), or any combination thereof. In another embodiment, the pulmonary or airway disease or disorder is cystic fibrosis. In another embodiment, the subject is a lung transplant patient. In another embodiment, the subject is a patient with non-cystic fibrosis bronchiectasis. In another embodiment, the subject is infected with a biofilm producing bacteria.

In some embodiments, the pulmonary or airway disease or disorder is bronchiectasis (BrE). Bronchiectasis can be diagnosed in patients suffering from cystic fibrosis (CF bronchiectasis) or patients without cystic fibrosis (non-CF bronchiectasis). To date, therapies that have been used in cystic fibrosis (CF) have not worked and have been shown to be potentially harmful in non-CF bronchiectasis.

Non-CF bronchiectasis and CF disease, including CF-associated bronchiectasis, are clinically distinct although they do have some of the same features. CF BrE affects primarily the upper lobes of the airways, whereas non-CF BrE is associated with more lower lobe involvement. Because non-CF BrE patients lack adequate mucociliary transport mechanisms, therapies that only break up components of mucus (e.g., DNase) cause sputum to pool in the lower airways and the lung parachyma rather than being expectorated. Sputum in CF contains more DNA compared to BrE patients, indicating distinct underlying physiologies. BrE patients are generally older with a higher prevalence in women, and CF patients are diagnosed at an early age and include equal male/female prevalence. (O'Donnell et al., Chest 1998 Volume 113, Issue 5, Pages 1329-1334).

In some embodiments, Compositions of the Disclosure are useful for treating, reducing the symptoms of, or preventing (e.g., non-cystic fibrosis bronchiectasis or cystic fibrosis bronchi ectasi s).

In another embodiment, the present disclosure provides methods of treating or preventing a clinical isolate bacteria infection in the airway of a subject in need thereof, the method comprising administering to the subject a therapeutically effective amount of a Composition of the Disclosure. In another embodiment, a Composition of the Disclosure is administered to the subject in combination with one or more antibiotics. The antibiotics can be administered locally to the lungs and/or systemically.

In another embodiment, the present disclosure provides methods of treating or preventing inflammation in the airway of a subject in need thereof, the method comprising administering to the subject a therapeutically amount of a Composition of the Disclosure.

In another embodiment, the present disclosure provides methods of treating or preventing a disease or disorder in mucosal tissue in a subject in need thereof, the method comprising administering to the subject a therapeutically effective amount of a Composition of the Disclosure. Non-limiting examples of mucosal tissue include the mouth, nose, eye, ear, upper respiratory tract, lower respiratory tract, gastrointestinal tract, vagina, rectum and urethra.

In another embodiment, the present disclosure provides methods of treating or preventing a disease or disorder associated with mucosal membranes, in a subject in need thereof, the method comprising administering to the subject a therapeutically amount of a Composition of the Disclosure to the appropriate mucosal membranes. In one embodiment, the mucosal membranes are the lungs, such as the deep lung (alveolar region), and in other embodiments, the mucosal membranes are one or more of the eyes, mouth, nose, rectum, and vagina.

In another embodiment, a Composition of the Disclosure can be used to treat or prevent bronchiolitis obliterans and military-related lung damage, i.e., lung damage of military personnel who have damaged airways secondary to unknown exposures.

In another embodiment, the present disclosure provides the use of a Composition of the Disclosure for the manufacture of a medicament for treatment of a pulmonary or airway disorder. In another embodiment, the use further comprises administering one or more additional therapeutic agents to the subject.

The therapeutic methods of this disclosure comprise administering a therapeutically effective amount of a Composition of the Disclosure to a subject in need thereof, e.g., a human patient. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

In one embodiment, the present disclosure provides a method for treating a pulmonary or airway disorder or disease in a subject infected with a clinical isolate bacteria or at risk for infection with a clinical isolate bacteria, the method comprising administering to the subject an effective amount of a Composition of the Disclosure.

In another embodiment, the pulmonary or airway disorder or disease is selected from the group consisting of chronic inflammatory lung disease, an inflammation and/or infection associated with lung transplantation, acute lung rejection, asthma, cystic fibrosis, bronchiectasis (e.g., non-cystic fibrosis bronchiectasis or cystic fibrosis bronchiectasis), and chronic obstructive pulmonary disease (COPD), and any combination thereof.

In another embodiment, the pulmonary or airway disorder or disease is treated by inhibiting clinical isolate bacteria growth in the airway of the subject.

In another embodiment, the pulmonary or airway disorder or disease is treated by restoring homeostasis to and/or maintaining homeostasis in a mucosal membrane of a subject in need thereof, the method comprising administering to the subject an effective amount of a Composition of the Disclosure.

In another embodiment, the present disclosure provides a method of restoring homeostasis to and/or maintaining homeostasis in a mucosal membrane of a subject in need thereof, the method comprising administering to the subject an effective amount of a Composition of the Disclosure.

In another embodiment, the present disclosure provides a method of restoring or maintaining homeostasis in a mucosal membrane comprising administering to the subject an effective amount of a Composition of the Disclosure.

In some embodiments, the methods of the disclosure comprise administering to the airway of the subject an effective amount of a composition comprising: a glutathione conjugate and/or glutathione, or a pharmaceutically acceptable salt thereof. In another embodiment, the composition further comprises: an organic acid, or a pharmaceutically acceptable salt thereof. In another embodiment, the organic acid is ascorbic acid. In another embodiment, the composition further comprises: a bicarbonate salt. In another embodiment, the bicarbonate salt is sodium bicarbonate or potassium bicarbonate. In some embodiments, the organic acid in a Compositon of the Disclosure is ascorbic acid. In some embodiments, the bicarbonate salt in a Composition of the Disclosure is sodium bicarbonate. In some embodiments, the composition comprises: (a) glutathione; (b) ascorbic acid; and (c) sodium bicarbonate. In certain embodiments, the molar ratio of (a):(b):(c) is about 0.1-0.5:0.5-1:1 (e.g., about 0.49:about 0.50:about 1). In other embodiments, the molar ratio of (a):(b):(c) is about 0.1-0.5:1:1 (e.g., about 0.49:about 1:about 1).

In another embodiment, the amount of each of component the glutathione conjugate and/or the glutathione, or a pharmaceutically acceptable salt thereof, the organic acid, or a pharmaceutically acceptable salt thereof, and the bicarbonate salt of the composition is present such that the amount of bicarbonate salt results in a pH in a range from about 5.5 to about 14. In some embodiments, the pH of a Composition of the Disclosure is from about 5.5 to about 14 (e.g. 5.5 to 7.5). In some embodiments, the pH of a Composition of the Disclosure is from about 6 to about 14 (e.g., 6 to 7.5). In some embodiments, the pH of the composition is 7±1.5, 7±1.4, 7±1.3, 7±1.2, 7±1.1, 6±0.5, 6±0.4, 6±0.3, 6±0.2, 6±0.5, 6±0.1, or about 6.

In another embodiment, the composition further comprises from about 0.01% to about 5% by weight of a pharmaceutically-acceptable thiocyanate salt.

In another embodiment, the composition is in the form of a particle. In another embodiment, the particle is mixed with a gas or liquid propellant for use in inhalation therapy.

In another embodiment, the glutathione is reduced glutathione.

In another embodiment, administration of the composition to the subject gives a concentration of about 0.1 mM to about 1.0 mM glutathione in the airway surface liquid of the subject. In another embodiment, administration of the composition to the subject gives a concentration of about 0.5 mM to about 3.0 mM thiocyanate in the airway surface liquid of the subject.

In some embodiments, the oxidized glutathione (e.g., % GSSG) in the Composition of the Disclosure is less than about 20%, less than about 18%, less than about 16%, less than about 15%, less than about 12%, less than about 10%, less than about 9%, less than about 8%, less than about 7%, less than about 6%, less than about 5%, less than about 4%, or less than about 3% by weight of the total glutathione in the Composition of the Disclosure after storage of the Composition of the Disclosure for 4 weeks (e.g., at 5° C. in a $N_2$ atmosphere and/or ambient atmosphere).

In some embodiments, the reduced glutathione in the Composition of the Disclosure is more than about 80%, more than about 82%, more than about 84%, more than about 85%, more than about 88%, more than about 90%, more than about 91%, more than about 92%, more than about 93%, more than about 94%, more than about 95%, more than about 96%, or more than about 97% by weight of the total glutathione in the Composition of the Disclosure after storage of the Composition of the Disclosure for 4 weeks at about 5° C. (e.g., in a $N_2$ or ambient atmosphere).

In some embodiments, the reduced ascorbic acid (e.g., % ASC) is more than about 80%, more than about 85%, more than about 86%, more than about 87%, more than about 88%, more than about 89%, or more than about 90% by weight of the ascorbic acid in the Composition of the Disclosure after storage of the Composition of the Disclosure for 4 weeks (e.g., at 5° C. in a $N_2$ atmosphere and/or ambient atmosphere).

In some embodiments, the oxidized ascorbic acid in the Composition of the Disclosure is less than about 20%, less than about 18%, less than about 16%, less than about 15%, less than about 12%, less than about 10%, or less than about 9% by weight of the total ascorbic acid in the Composition of the Disclosure after storage of the Composition of the Disclosure for 4 weeks (e.g., at 5° C. in a $N_2$ atmosphere and/or ambient atmosphere).

In some embodiments, the composition is an aqueous solution or a dry powder. In another embodiment, the composition is administered by inhalation to the subject.

a. Antibacterial Methods of Use

While most antibacterial agents (e.g., antibiotics) have activity solely against Gram negative bacteria or solely against Gram positive bacteria, Composition of the Disclosure demonstrate broad spectrum activity against both Gram negative and Gram positive bacteria. Such properties are unexpected in view of studies showing that ascorbic acid alone acts in a strain-dependent and highly concentration-dependent manner (see, e.g., Med J Aust. 1974 Feb. 9; 1(6):169-74; Hancock and Wong. Antimicrob agents and chemotherapy, July 1984: 48-52). Clinical conditions complicate the use of broad-spectrum antibiotics in chronic inflammatory airways diseases such as cystic fibrosis, bronchiectasis (e.g., non-cystic fibrosis bronchiectasis or cystic fibrosis bronchiectasis), and lung transplant. Moreover, physicians often use antibiotics empirically and based on patient response. In contrast to the Compositions of the Disclosure, current antibiotic therapies do not show consistent efficacies against bacteria commonly found in chronic inflammatory airway diseases.

Compositions of the Disclosure can actively inhibit multiple bacterial species without conferring bacteria protective mechanisms.

Accordingly, in some embodiments, the Compositions of the Disclosure are useful for inhibiting or reducing growth of a clinical isolate bacteria. In some embodiments, the Compositions of the Disclosure are useful for inhibiting or reducing formation of a clinical isolate bacteria biofilm. In some embodiments, the Compositions of the Disclosure are useful for treating or reducing symptoms in a subject suffering from or at risk for a clinical isolate bacteria infection.

In certain aspects, clinical isolate of the application can comprise a single bacterial strain or a combination (i.e., two or more) of bacterial strains. In certain embodiments, the clinical isolate is selected from the group consisting of *Pseudomonas aeruginosa, Staphylococcus aureus*,Methicillin-resistant *Staphylococcus aureus* (MRSA), *Actinobacter baumannii, Burkholderia pseudomallei, Burkholderia cepacia*, or any combination thereof.

In some embodiments, the clinical isolate is gram negative. In certain embodiments, the gram negative clinical isolate is selected from the group consisting of *Burkholderia cepacia, Pseudomonas aeruginosa, Actinobacter baumannii, Burkholderia pseudomallei*, or any combination thereof. In some embodiments, the *Pseudomonas aeruginosa* is mucoidy or nonmucoid, or combination thereof.

In some embodiments, the clinical isolate is gram positive. In certain embodiments, the gram positive clinical isolate is selected from the group consisting of *Enterococcus, Streptococcus, Pneumococcus, Staphylococcus* (e.g., *Staphylococcus aureus* or Methicillin-resistant *Staphylococcus aureus* (MRSA), and any combination thereof. In some embodiments, the Gram positive clinical isolate is *Staphylococcus aureus* or Methicillin-resistant *Staphylococcus aureus* (MRSA) or a combination thereof.

In some embodiments, the clinical isolate is mucoid. In certain embodiments, the mucoid clinical isolate is *Pseudomonas aeruginosa, Burkholderia cepacia*, and any combination thereof.

In some embodiments, the clinical isolate is non-mucoid. In certain embodiments, the clinical isolate is clinical non-mucoid *Pseudomonas aeruginosa*.

In some embodiments, the clinical isolate is aerobic. In certain embodiments, the aerobic clinical isolate is

*Pseudomonas aeruginosa, Burkholderia cepacia, Staphylococcus aureus*, and Methicillin-resistant *Staphylococcus aureus* (MRSA), and any combination thereof. In certain embodiments, the aerobic condition is with nitrate. In certain embodiments, the aerobic condition is without nitrate.

In some embodiments, the clinical isolate is anaerobic or aerotolerant. In certain embodiments, the anaerobic or aerotolerant clinical isolate is selected from the group consisting of *Staphylococcus aureus*, Methicillin-resistant *Staphylococcus aureus* (MRSA), *Burkholderia cepacia*, *Pseudomonas aeruginosa*, *Staphylococcus aureus*, and any combination thereof. In certain embodiments, the anaerobic or aerotolerant condition is with nitrate. In certain embodiments, the anaerobic or aerotolerant condition is without nitrate.

In some embodiments, the clinical isolate can live extracellularly. In certain embodiments, the clinical isolate that can live extracellularly is *Burkholderia cepacia, Pseudomonas aeruginosa, Staphylococcus aureus*, and Methicillin-resistant *Staphylococcus aureus* (MRSA), and any combination thereof.

In some embodiments, the clinical isolate is multidrug resistant. In certain embodiments, the multidrug resistant clinical isolate is selected from the group consisting of *Staphylococcus aureus*, Methicillin-resistant *Staphylococcus aureus* (MRSA), *Pseudomonas aeruginosa*, *Burkholderia cepacia*, and any combination thereof.

In some embodiments, the clinical isolate is resistant to cationic protein treatment. In certain embodiments, the cationic protein treatment resistant clinical isolate is selected from the group consisting of *Pseudomonas aeruginosa, Burkholderia cepacia*, and any combination thereof.

*Pseudomonas Aeruginosa*

In one embodiment, the clinical isolate bacteria are *Pseudomonas aeruginosa*.

*Pseudomonas aeruginosa* is a gram-negative bacterium that can cause infection, especially in patients with compromised host defense mechanisms. It is the most common pathogen isolated from patients who have been hospitalized longer than 1 week, and it is a frequent cause of nosocomial infections. Pseudomonal infections can be life-threatening.

*Pseudomonas aeruginosa* is a metabolically versatile bacterium that can cause a wide range of severe opportunistic infections in patients with compromised natural defenses. Predisposing conditions can include, e.g., a disrupted epithelial barrier (as found in burn wound patients), a depletion of neutrophils (for example, in a cancer patient receiving chemotherapy), the presence of a foreign body (a patient with a central venous catheter), and altered mucociliary clearance (e.g., in individuals with cystic fibrosis). *Pseudomonas aeruginosa* is intrinsically resistant to a large number of antibiotics and can acquire resistance to others, making treatment difficult. The propensity of *Pseudomonas aeruginosa* to form biofilms further protects it from antibiotics and from a host immune system. In some embodiments, the clinical isolate is the mucoid *Pseudomonas aeruginosa*. In some embodiments, the clinical isolate is the non-mucoid *Pseudomonas aeruginosa*.

*Pseudomonas aeruginosa* is commonly isolated from the respiratory tracts of individuals with cystic fibrosis and is associated with an accelerated decline in lung function in these patients. Chronic lung colonization and infection also occurs in bronchiectasis (e.g., non-cystic fibrosis bronchiectasis or cystic fibrosis bronchiectasis), a disease characterized by irreversible dilation of the bronchial tree, and in chronic obstructive pulmonary disease, a disease characterized by narrowing of the airways and abnormalities in air flow. In addition, *Pseudomonas aeruginosa* is one of the most common causes of hospital acquired pneumonia, especially in mechanically ventilated patients; it is associated with a particularly high mortality rate.

Exposure to various in vivo environments results in activation of a variety of metabolic patterns in *Pseudomonas aeruginosa* to defend itself against reactive nitrogen species. This can result in host mucoidy production.

*Burkholderia Cepacia*

In another embodiment, the clinical isolate bacteria are *Burkholderia cepacia*.

*Burkholderia cepacia* is an aerobic gram-negative bacillus found in various aquatic environments. *Burkholderia cepacia* is an organism of low virulence and is a frequent colonizer of fluids used in the hospital (e.g., irrigation solutions, intravenous fluids). *Burkholderia cepacia* rarely causes infection in healthy hosts. Based on phenotypic and genotypic analyses, *Burkholderia cepacia* is one of the divided into 9 genovars that constitute the *Burkholderia cepacia* complex (BCC).

BCC is an important group of pathogens affecting patients with cystic fibrosis and chronic granulomatous disease as well as immunocompromised and hospitalised patients. Avgeri et al. Int J Antimicrob Agents. 2009 May; 33(5):394-404. BCC mutates frequently and acquires high levels of resistance to many antimicrobial agents. These bacteria are associated with clinical decline and mortality in chronic inflammatory airways diseases and even could develop multi-drug resistance. Although they generally are thought to be aerobic, some exhibit fermentation and nitrate respiration. Sass et al. ISME J. 2013 August; 7(8):1568-81.

*Staphylococcus Aureus* and methicillin-resistant *Staphylococcus Aureus* (MRSA)

In another embodiment, the clinical isolate bacteria are *Staphylococcus aureus* or methicillin-resistant *Staphylococcus aureus* (MRSA), both of which are Gram positive cocci.

*Staphylococcus aureus* is an important cause of pneumonia. These bacteria are specifically implicated in the development of pleuropulmonary infections, and generally co-localize with *Pseudomonas aeruginosa* or *Burkholderia cepacia* in chronic inflammatory airways diseases. Tong et al. Clin Microbiol Rev. 2015 July; 28(3):603-61. In one embodiment, *Staphylococcus aureus* is identified in lung transplant patients with acute and chronic rejection.

MRSA infection is caused by *Staphylococcus aureus* that has become resistant to many of the antibiotics used to treat ordinary staph infections. HA-MRSA infections typically are associated with invasive procedures or devices, such as surgeries, intravenous tubing or artificial joints. Community-associated MRSA (CA-MRSA) is another type of MRSA infection that has occurred in the wider community often among otherwise healthy people. This form, often begins as a painful skin boil. It is spread by skin-to-skin contact. At-risk populations include groups such as high school wrestlers, child care workers and people who live in crowded conditions.

b. Methods of Increasing Mucociliary Clearance

Mucociliary clearance is critical in preventing infections and inflammation in the lung. However, mucociliary clearance is often absent or impaired in chronic inflammatory airways diseases such as cystic fibrosis, bronchiectasis (e.g., non-cystic fibrosis bronchiectasis or cystic fibrosis bronchiectasis), lung transplant and chronic obstructive pulmonary disease. Moreover, airway epithelial cells from cystic fibrosis patients are known to completely lack mucociliary clearance ability without other inflammatory insults or bacterial colonization or infection. Although some studies have focused on modification of the airway microenvironment to restore function to previously functional tissue, Compositions of the Disclosure are capable of activating mucociliary clearance functions in epithelial cells otherwise devoid of such functions.

Ascorbic acid can directly modulate CFTR activity (Proc Natl Acad Sci USA. 2004 Mar. 9; 101(10): 3691-3696.). However, ascorbic acid has also been shown to have limited effect on mucociliary clearance (BMC Complement Altern Med. 2013; 13:110.) and limited clinical efficacy (Sakasura Ann Otol 82; 1973). However, the Compositions of the Disclosure can restore mucociliary function in the absence of a bacterial infection.

When administered individually, glutathione, ascorbic acid, and bicarbonate do not have any clinical impact on mucociliary clearance or clinical outcomes (Sakasura Ann Otol 82; 1973; Am J Respir Crit Care Med. 2013 Jul. 1; 188(1):83-9. doi: 10.1164/rccm.201303-04270C.). Moreover, the effects of bicarbonate have been inconclusive despite clinical data that directly effects the pH of the airway.

Compositions of the Disclosure generate a synergistic effect between glutathione, ascorbic acid, and bicarbonate, and can activate mucociliary clearance to levels seen in normal cells (Am J Respir Crit Care Med. 2014 Aug. 15; 190(4): 421-432.). Accordingly, in some embodiments, Composition of the Disclosure are useful in upregulating mucociliary clearance in a subject suffering from or at risk of impaired mucociliary clearance.

In some embodiments, the disclosure comprises a method of upregulating mucociliary clearance in a subject suffering from or at risk of impaired mucociliary clearance comprising administering to the subject a composition comprising: (a) glutathione, a glutathione derivative, a glutathione conjugate, a pharmaceutically-acceptable salt thereof and (b) an organic acid.

In another embodiment, the organic acid is ascorbic acid. In another embodiment, the composition further comprises: (c) a bicarbonate salt. In another embodiment, the bicarbonate salt is sodium bicarbonate or potassium bicarbonate. In some embodiments, the organic acid in a is ascorbic acid. In some embodiments, the composition comprises: (a) glutathione; (b) ascorbic acid; and (c) sodium bicarbonate. In certain embodiments, the molar ratio of (a):(b):(c) is about 0.1-0.5:0.5-1:1 (e.g., about 0.49:about 0.50:about 1). In other embodiments, the molar ratio of (a):(b):(c) is about 0.1-0.5:1:1 (e.g., about 0.49:about 1:about 1).

In another embodiment, the amount of each of component the glutathione conjugate and/or the glutathione, or a pharmaceutically acceptable salt thereof, the organic acid, or a pharmaceutically acceptable salt thereof, and the bicarbonate salt of the composition is present such that the amount of bicarbonate salt results in a pH in a range from about 5.5 to about 14. In some embodiments, the pH of a Composition of the Disclosure is from about 5.5 to about 14 (e.g. 5.5 to 7.5). In some embodiments, the pH of a Composition of the Disclosure is from about 6 to about 14 (e.g., 6 to 7.5). In some embodiments, the pH of the composition is 7±1.5, 7±1.4, 7±1.3, 7±1.2, 7±1.1, 6±0.5, 6±0.4, 6±0.3, 6±0.2, 6±0.5, 6±0.1, or about 6.

In another embodiment, the composition further comprises from about 0.01% to about 5% by weight of a pharmaceutically-acceptable thiocyanate salt.

In another embodiment, the composition is in the form of a particle. In another embodiment, the particle is mixed with a gas or liquid propellant for use in inhalation therapy.

In another embodiment, the glutathione is reduced glutathione.

In another embodiment, administration of the composition to the subject gives a concentration of about 0.1 mM to about 1.0 mM glutathione in the airway surface liquid of the subject. In another embodiment, administration of the composition to the subject gives a concentration of about 0.5 mM to about 3.0 mM thiocyanate in the airway surface liquid of the subject.

In some embodiments, the oxidized glutathione (e.g., % GSSG) in the Composition of the Disclosure is less than about 20%, less than about 18%, less than about 16%, less than about 15%, less than about 12%, less than about 10%, less than about 9%, less than about 8%, less than about 7%, less than about 6%, less than about 5%, less than about 4%, or less than about 3% by weight of the total glutathione in the Composition of the Disclosure after storage of the Composition of the Disclosure for 4 weeks (e.g., at 5° C. in a $N_2$ atmosphere and/or ambient atmosphere).

In some embodiments, the reduced glutathione in the Composition of the Disclosure is more than about 80%, more than about 82%, more than about 84%, more than about 85%, more than about 88%, more than about 90%, more than about 91%, more than about 92%, more than about 93%, more than about 94%, more than about 95%, more than about 96%, or more than about 97% by weight of the total glutathione in the Composition of the Disclosure after storage of the Composition of the Disclosure for 4 weeks at about 5° C. (e.g., in a $N_2$ or ambient atmosphere).

In some embodiments, the reduced ascorbic acid (e.g., % ASC) is more than about 80%, more than about 85%, more than about 86%, more than about 87%, more than about 88%, more than about 89%, or more than about 90% by weight of the ascorbic acid in the Composition of the Disclosure after storage of the Composition of the Disclosure for 4 weeks (e.g., at 5° C. in a $N_2$ atmosphere and/or ambient atmosphere).

In some embodiments, the oxidized ascorbic acid in the Composition of the Disclosure is less than about 20%, less than about 18%, less than about 16%, less than about 15%, less than about 12%, less than about 10%, or less than about 9% by weight of the total ascorbic acid in the Composition of the Disclosure after storage of the Composition of the Disclosure for 4 weeks (e.g., at 5° C. in a $N_2$ atmosphere and/or ambient atmosphere).

In some embodiments, the composition is an aqueous solution or a dry powder. In another embodiment, the composition is administered by inhalation to the subject.

In some embodiments, administering the composition decreases mucus viscosity of the patient. In some embodiments, administering the composition increases ciliary beat frequency of the patient's airway epithelial cells. In some embodiments, administering the composition increases the mucociliary transport rate of the patient's airway epithelial cells. In some embodiments, administering said composition increases the airway surface liquid height of the patient.

In some embodiments, the patient suffers from or is at risk of suffering from a chronic inflammatory airway disease. In some embodiments, the inflammatory airway disease is cystic fibrosis, bronchiectasis (e.g., non-cystic fibrosis bronchiectasis or cystic fibrosis bronchiectasis), asthma, chronic obstructive pulmonary disease, or pulmonary fibrosis. In some embodiments, the inflammatory airway disease is cystic fibrosis. In some embodiments, the airway epithelial cells of the patient lack mucociliary clearance ability prior to administration of said composition. In some embodiments, the airway epithelial cells of said patient lack mucociliary clearance ability due to a genetic deficiency.

In some embodiments, the patient has received a lung transplant.

In some embodiments, the airway epithelium of the patient is not colonized by bacteria. In other embodiments, the airway epithelium of the patient is colonized by bacteria. In some embodiments, the patient suffers from an active bacterial infection. In other embodiments, the patient does not suffer from an active bacterial infection.

In some embodiments, the patient is a pediatric patient. In other embodiments, the patient is an adult patient.

c. Anti-Inflammatory Methods of Use

Hallmarks of inflammation in airway disease include the production of neutrophil extracellular traps (NETs), increased neutrophil myeloperoxidase activity, increased nitric oxide production, and increased production of pro-inflammatory cytokines. Studies suggest that ascorbic acid specifically enhances myeloperoxidase (MPO) activity and promotes leukocyte recruitment, and that the presence of MPO is directly associated with clinical complication and deterioration (Free Radic Biol Med. 2017 Oct. 2; 113:236-243). Moreover, neutrophil extracellular trap formation caused by phorbol myristate acetate (PMA) is prevented under acidic conditions and elicited under more basic conditions resulting from high concentrations of sodium bicarbonate.

Compositions of the Disclosure directly inhibit the inflammatory process. In particular, Compositions of the Disclosure inhibit MPO activity, as well as downregulate cytokines associated with NET formation, macrophage activation and neutrophil and T cell recruitment in a mechanism independent of reducing functions. The Compositions of the Disclosure can downregulate the level of pathological nitric oxide production and therefore not disrupt endogenous antibacterial properties. In some embodiments, administering said composition reduces the patient's fractional exhaled nitric oxide (FeNO) by at least 20%. Accordingly, in some embodiments, Compositions of the Disclosure are useful for reducing airway inflammation in a subject suffering from or at risk of airway inflammation.

In some embodiments, the disclosure comprises a method of reducing airway inflammation in a subject suffering from or at risk of airway inflammation comprising administering to the subject a composition comprising: (a) glutathione, a glutathione derivative, a glutathione conjugate, a pharmaceutically-acceptable salt thereof and (b) an organic acid.

In another embodiment, the organic acid is ascorbic acid. In another embodiment, the composition further comprises: (c) a bicarbonate salt. In another embodiment, the bicarbonate salt is sodium bicarbonate or potassium bicarbonate. In some embodiments, the organic acid in a is ascorbic acid. In some embodiments, the composition comprises: (a) glutathione; (b) ascorbic acid; and (c) sodium bicarbonate. In certain embodiments, the molar ratio of (a):(b):(c) is about 0.1-0.5:0.5-1:1 (e.g., about 0.49:about 0.50:about 1). In other embodiments, the molar ratio of (a):(b):(c) is about 0.1-0.5:1:1 (e.g., about 0.49:about 1:about 1).

In another embodiment, the amount of each of component the glutathione conjugate and/or the glutathione, or a pharmaceutically acceptable salt thereof, the organic acid, or a pharmaceutically acceptable salt thereof, and the bicarbonate salt of the composition is present such that the amount of bicarbonate salt results in a pH in a range from about 5.5 to about 14. In some embodiments, the pH of a Composition of the Disclosure is from about 5.5 to about 14 (e.g. 5.5 to 7.5). In some embodiments, the pH of a Composition of the Disclosure is from about 6 to about 14 (e.g., 6 to 7.5). In some embodiments, the pH of the composition is 7±1.5, 7±1.4, 7±1.3, 7±1.2, 7±1.1, 6±0.5, 6±0.4, 6±0.3, 6±0.2, 6±0.5, 6±0.1, or about 6.

In another embodiment, the composition further comprises from about 0.01% to about 5% by weight of a pharmaceutically-acceptable thiocyanate salt.

In another embodiment, the composition is in the form of a particle. In another embodiment, the particle is mixed with a gas or liquid propellant for use in inhalation therapy.

In another embodiment, the glutathione is reduced glutathione.

In another embodiment, administration of the composition to the subject gives a concentration of about 0.1 mM to about 1.0 mM glutathione in the airway surface liquid of the subject. In another embodiment, administration of the composition to the subject gives a concentration of about 0.5 mM to about 3.0 mM thiocyanate in the airway surface liquid of the subject.

In some embodiments, the oxidized glutathione (e.g., % GSSG) in the Composition of the Disclosure is less than about 20%, less than about 18%, less than about 16%, less than about 15%, less than about 12%, less than about 10%, less than about 9%, less than about 8%, less than about 7%, less than about 6%, less than about 5%, less than about 4%, or less than about 3% by weight of the total glutathione in the Composition of the Disclosure after storage of the Composition of the Disclosure for 4 weeks (e.g., at 5° C. in a $N_2$ atmosphere and/or ambient atmosphere).

In some embodiments, the reduced glutathione in the Composition of the Disclosure is more than about 80%, more than about 82%, more than about 84%, more than about 85%, more than about 88%, more than about 90%, more than about 91%, more than about 92%, more than about 93%, more than about 94%, more than about 95%, more than about 96%, or more than about 97% by weight of the total glutathione in the Composition of the Disclosure after storage of the Composition of the Disclosure for 4 weeks at about 5° C. (e.g., in a $N_2$ or ambient atmosphere).

In some embodiments, the reduced ascorbic acid (e.g., % ASC) is more than about 80%, more than about 85%, more than about 86%, more than about 87%, more than about 88%, more than about 89%, or more than about 90% by weight of the ascorbic acid in the Composition of the Disclosure after storage of the Composition of the Disclosure for 4 weeks (e.g., at 5° C. in a $N_2$ atmosphere and/or ambient atmosphere).

In some embodiments, the oxidized ascorbic acid in the Composition of the Disclosure is less than about 20%, less than about 18%, less than about 16%, less than about 15%, less than about 12%, less than about 10%, or less than about 9% by weight of the total ascorbic acid in the Composition of the Disclosure after storage of the Composition of the Disclosure for 4 weeks (e.g., at 5° C. in a $N_2$ atmosphere and/or ambient atmosphere).

In some embodiments, the composition is an aqueous solution or a dry powder. In another embodiment, the composition is administered by inhalation to the subject.

In some embodiments, administering the composition inhibits myeloperoxidase activity of the patient's neutrophils. In some embodiments, administering the composition decreases the formation of neutrophil extracellular traps. In some embodiments, administering the composition downregulates the production of nitric oxide from the patient's neutrophils. In some embodiments, administering the composition reduces the patient's fractional exhaled nitric oxide by at least 20%, at least 21%, at least 22%, at least 23%, at least 24%, or at least 25%. In some embodiments, administering the composition reduces the patient's baseline fractional exhaled nitric oxide by at least 20%.

In some embodiments, administering the composition downregulates the production of at least one inflammatory cytokine. In some embodiments, the at least one inflammatory cytokine comprises a cytokine associated with macrophage activation and/or neutrophil and T cell recruitment. In some embodiments, the at least one inflammatory cytokine comprises TNF-α. In some embodiments, the at least one inflammatory cytokine comprises IL-6. In some embodiments, the at least one inflammatory cytokine comprises IL-8.

In some embodiments, the patient suffers from or is at risk of suffering from a chronic inflammatory airway disease. In some embodiments, the inflammatory airway disease is cystic fibrosis, bronchiectasis (e.g., non-cystic fibrosis bronchiectasis or cystic fibrosis bronchiectasis), asthma, chronic obstructive pulmonary disease, or pulmonary fibrosis. In some embodiments, the inflammatory airway disease is cystic fibrosis.

In some embodiments, the patient has received a lung transplant.

In some embodiments, the airway epithelium of the patient is not colonized by bacteria. In some embodiments, the airway epithelium of the patient is colonized by bacteria. In certain embodiments, the patient suffers from an active bacterial infection. In other embodiments, the patient does not suffer from an active bacterial infection.

In some embodiments, the patient is a pediatric patient. In other embodiments, the patient is an adult patient.

In some embodiments, administering the composition does not significantly alter the pH of the patient's airway endothelium.

Administration

The therapeutic methods of this disclosure can be accomplished by administering a Composition of the Disclosure to a subject. Administration of a Composition of the Disclosure can be performed before, during, or after the onset of the disease, condition, or disorder of interest. Typically, the pharmaceutical compositions are sterile, and contain no toxic, carcinogenic, or mutagenic compounds that would cause an adverse reaction when administered to the subject.

Compositions of the Disclosure are administered in a manner compatible with the dosage formulation in such an amount as will be effective for the desired result. In particular embodiments, Compositions of the Disclosure are administered to the subject in a therapeutically effective amount. A therapeutically effective amount of Compositions of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of glutathione that are sufficient to maintain the desired therapeutic effects. The desired dose can be administered in a single dose, or as multiple doses administered at appropriate intervals, for example as one, two, three, four or more subdoses per day. Multiple doses often are desired, or required. For example, glutathione, a glutathione derivative, a glutathione conjugate, a pharmaceutically-acceptable salt thereof, or any combination thereof can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days' rest, and another five daily doses (5/2/5); or, any dose regimen determined to be appropriate for the circumstance.

Compositions of the Disclosure can be administered for a sustained period, such as for at least about one month, at least about 2 months, at least about 3 months, at least about 6 months, or at least about 12 months or longer (e.g., as a chronic life-long treatment).

Any suitable dosing schedule can be followed. For example, the dosing frequency can be a once weekly dosing. The dosing frequency can be a once daily or multiple times daily dosing. The dosing frequency can be more than once weekly dosing. The dosing frequency can be more than once daily dosing, such as any one of 2, 3, 4, 5, 6, 7, 8, 9, 10 or more than 10 daily doses. The dosing frequency can be intermittent (e.g., multiple daily dosing for 7 days followed by no doses for 7 days, repeated for any 14 day time period, such as 2 months, 4 months, 6 months or more). The dosing frequency can be continuous (e.g., one weekly dosing for continuous weeks).

Glutathione, a glutathione derivative, a glutathione conjugate, a pharmaceutically-acceptable salt thereof, or any combination thereof used in a therapeutic method of the present disclosure can be administered in an amount of about 0.005 to about 1,000 milligrams per dose, about 0.05 to about 250 milligrams per dose, or about 0.5 to about 100 milligrams per dose. For example, glutathione, a glutathione derivative, a glutathione conjugate, a pharmaceutically-acceptable salt thereof, or any combination thereof can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 1,000 milligrams.

The dosage of glutathione, a glutathione derivative, a glutathione conjugate, a pharmaceutically-acceptable salt thereof, or any combination thereof, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition can be at any dosage including, but not limited to, about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

In one embodiment, glutathione, a glutathione derivative, a glutathione conjugate, a pharmaceutically-acceptable salt thereof, or any combination thereof is delivered to the upper third of the nasal cavity, to the superior meatus, the olfactory region and/or the sinus region of the nose. The olfactory region is a small area that is typically about 2-10 cm$^2$ in man located in the upper third of the nasal cavity for deposition and absorption by the olfactory epithelium and subsequent transport by olfactory receptor neurons. Located on the roof of the nasal cavity, in the superior meatus, the olfactory region is useful for delivery in some embodiments, because it is the only known part of the body in which an extension of the CNS comes into contact with the environment (Bois et al. Fundamentals of Otolaryngology, p. 184, W. B. Saunders Co., Philadelphia, 1989).

In some embodiments, a Composition of the Disclosure can be administered in a single "shock" dose, for example, during a bronchoscopy. In other embodiments, the methods of the disclosure can be carried out on an as-needed basis by self-medication.

Any of the dosing frequencies can be used with any dosage amount. Further, any of the dosing frequencies and/or dosage amounts can be used with any of the Compositions of the Disclosure.

A Composition of the Disclosure can be delivered in any suitable volume of administration, In representative embodiments of the disclosure, the administration volume for intranasal delivery ranges from about 25 microliters to 200 microliters or from about 50 to 150 microliters or from about 50, 100, 250 or 500 microliters to about 1, 2, 3, 3.5 or 4 milliliters in a human. Typically, the administration volume is selected to be large enough to allow for delivery of therapeutic quantities while accounting for dilution in ASL in maintenance conditions in relatively "normal" airways (10-30 ml ASL) and in cystic fibrosis (CF) airways (40-50 ml ASL or more plus thick, tenacious, and heavily infected mucus secretions).

The Compositions of the Disclosure can find use in both veterinary and/or medical applications. Suitable subjects of the present disclosure include, but are not limited to mammals. The term "mammal" as used herein includes, but is not limited to, primates (e.g., simians and humans), non-human primates (e.g., monkeys, baboons, chimpanzees, gorillas), bovines, ovines, caprines, ungulates, porcines, equines, felines, canines, lagomorphs, pinnipeds, rodents (e.g., rats, hamsters, and mice), etc. In some embodiments of the present disclosure, the subject is a human. Human subjects include both males and females and subjects of all ages including neonatal, infant, juvenile, adolescent, adult, and geriatric subjects.

In some embodiments, a Composition of the Disclosure is administered one or more times daily (e.g., 1, 2, 3, 4, 5, 6, 7, 8, 9, 10 or more times a day). In particular embodiments, the subject is a human.

In some embodiments of the methods of this disclosure, a Composition of the Disclosure can be administered via inhalation, intranasally, via the eye, via the ear, via sinus irrigation, or via bronchoscope, or any combination thereof.

Intranasal administration of a Composition of the Disclosure can be achieved by any known method. In particular embodiments, intranasal administration is by inhalation (e.g., using an inhaler, atomizer or nebulizer device), alternatively, by spray, tube, catheter, syringe, dropper, packtail, pipette, pledget, and the like.

As a further illustration, a Composition of the Disclosure can be administered intranasally as (1) nose drops, (2) powder or liquid sprays or aerosols, (3) liquids or semisolids by syringe, (4) liquids or semisolids by swab, pledget or other similar means of application, (5) a gel, cream or ointment, (6) an infusion, or (7) by injection, or by any means now known or later developed in the art. In particular embodiments, the method of delivery is by nasal drops, spray or aerosol. As used herein, aerosols can be used to deliver powders, liquids or dispersions (solids in liquid).

In some embodiments, the pharmaceutical formulation is directed upward during administration, so as to enhance delivery to the upper third (e.g., the olfactory epithelium in the olfactory region) and the side walls (e.g., nasal epithelium) of the nasal cavity. Further, orienting the subject's head in a tipped-back position or orienting the subject's body in Mygind's position or the praying-to-Mecca position can be used to facilitate delivery to the olfactory region.

The formulations can be provided in single or multidose form. In the latter case a means of dose metering can be provided. In the case of a dropper or pipette, this can be achieved by the patient or caregiver administering an appropriate, predetermined volume of the composition. In the case of a spray, this can be achieved, for example, by means of a metering atomizing spray pump.

In a further aspect, the present disclosure provides an intranasal spray device comprising a Composition of the Disclosure.

Many devices are known in the art for nasal delivery. Exemplary devices include particle dispersion devices, bidirectional devices, and devices that use chip-based ink jet technologies.

When a therapeutically effective amount of a Composition of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A composition for intravenous, cutaneous, or subcutaneous injection typically contains an isotonic vehicle.

Compositions of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of glutathione, a glutathione derivative, a glutathione conjugate, a pharmaceutically-acceptable salt thereof, or any combination thereof can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Glutathione, a glutathione derivative, a glutathione conjugate, a pharmaceutically-acceptable salt thereof, or any combination thereof also can be formulated in rectal compositions, such as suppositories or retention enemas, e.g., containing conventional suppository bases. In addition to the formulations described previously, glutathione, a glutathione derivative, a glutathione conjugate, a pharmaceutically-acceptable salt thereof, or any combination thereof also can be formulated as a depot preparation. Such long-acting formulations can be administered by implantation (for example, subcutaneously or intramuscularly) or by intramuscular injection. Thus, for example, glutathione, a glutathione derivative, a glutathione conjugate, a pharmaceutically-acceptable salt thereof, or any combination thereof can be formulated with suitable polymeric or hydrophobic materials (for example, as an emulsion in an acceptable oil) or ion exchange resins.

Compositions of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compositions of the Disclosure also can be injected parenterally, for example, intravenously, intramuscularly, subcutaneously, or intracoronarily. For parenteral administration, the Compositions of the Disclosure are typically used in the form of a sterile aqueous solution which can contain other substances, for example, salts or monosaccharides, such as mannitol or glucose, to make the solution isotonic with blood.

Compositions of the Disclosure can be present, for example, as a solid formulation, such as a particle formulation, or as a solution. When in a particle formulation, the particles can be mixed with gases, or liquid propellants, for use in inhalation therapy. Other solid formulations include formulations for oral administration, buccal administration or colonic administration, and suppositories for rectal or vaginal administration. Exemplary formulations include, but are not limited to, the following: eye drops, nebulizers, topical gels and ointments, dry powders, particles, sprays, liquids, anesthetic machines or vaporizers, autoinjectors, intrauterine devices, respimats, liniments, liposomes, lotions, formulations for intramuscular, intrathecal, or subcutaneous injection, douches, infusions, and face masks.

In solution form, the formulations can be in the form of sprays for intranasal administration, formulations for use in nebulizers, and formulations for rectal administration, such as enemas and colonies. Solutions that include water-miscible organic solvents, such as propylene glycol and/or glycerol, and other components normally found in vaginal and rectal lubricants, can also be used. Regardless of the solvents used, the solvent is typically present in a weight ratio of from about 15 to about 85 percent by weight, relative to the weight of the solids, and, more typically, is from about 50 to about 85% by weight.

The compositions and/or formulations of this invention can be used to treat disorders associated with a mucosal membrane, by delivering the compositions and/or formulations to the mucosal membrane(s) to be treated. In some embodiments, the mucosal membrane can be in or near the lungs, such as the deep lung (alveolar region), and in other embodiments, the mucosal membrane(s) can be in or near one or more of the eyes, mouth, nose, rectum, and/or vagina.

Additional Therapeutic Agents

In another embodiment, the present disclosure provides a method comprising administering to the subject an effective amount of an additional therapeutic agent.

Compositions comprising glutathione, a glutathione derivative, a glutathione conjugate, a pharmaceutically-acceptable salt thereof, organic acid, or any combination thereof can also be combined with antibiotics to increase efficacy of treatment.

In another emobodiment, one object of the invention is to identify clinical isolates in a patient sample and test efficacy of treatment in vitro by treatment with a composition comprising glutathione, a glutathione derivative, a glutathione conjugate, a pharmaceutically-acceptable salt thereof, organic acid, or any combination thereof.

Drugs administered to the lungs are often associated with certain side effects, in some cases because of dosage, and in other cases because they damage the lung tissue. In some embodiments, therapeutic agents combined with the compositions disclosed herein are effective at lower doses, and at such lower doses, the incidence of side effects can be reduced. In other embodiments, where the therapeutic agent interacts unfavorably with lung tissue, the compositions described herein can help to restore homeostasis to the lung tissue, and thus help minimize or eliminate damage caused by the therapeutic agents.

In another embodiment, the present disclosure provides a the therapeutic agent is selected from the group consisting of Fluticasone, Budesonide, Mometasone, Ciclesonide, Flunisolide, Beclomethasone, Albuterol, Levalbuterol, Ipratropium, Tiotropium, Formoterol, Arformoterol, Indacaterol, Aclidinium, and Pirbuterol, penicillins such as Amoxicillin, Ampicillin, Azlocillin, Carbenicillin, Cloxacillin, Cayston, Dicloxacillin, Flucloxacillin, Mezlocillin, Methicillin, Nafcillin, Oxacillin, Penicillin G, Penicillin V, Piperacillin, Penicillin G, Temocillin, and Ticarcillin, and combinations of penicillins with other therapeutic agents, such as Amoxicillin/clavulanate, Ampicillin/sulbactam, Piperacillin/tazobactam, Ticarcillin/clavulanate, and any combination thereof.

In one embodiment, the therapeutic agent is selected from the group consisting of Fluticasone, Budesonide, Mometasone, Ciclesonide, Flunisolide, Beclomethasone, Albuterol, Levalbuterol, Ipratropium, Tiotropium, Formoterol, Arformoterol, Indacaterol, Aclidinium, Cayston, Pirbuterol, and any combination thereof.

Additional therapeutic agents that can be combined with the compositions and formulations of this invention include, but are not limited to, Fluticasone (for example, sold as Flovent diskus 50 or as Flonase, GlaxoSmithKline), Budesonide (for example, sold as Pulmicort respules or Rhinocort by Astra Zeneca ("AZ"), Mometasone (sold as Nasonex as a spray, or as Asmanex Twisthaler by Merck/S-P), Ciclesonide (sold as Alvesco or Onmaris by Takeda Pharmaceuticals), Flunisolide (sold as Aerobid by Roche Palo or by Aerospan HFA by GSK), Beclomethasone (sold as Qvar or Onasl by Teva Pharmaceuticals), Albuterol (sold as ProAir HFA by Teva and as Ventolin HFA by GSK), Levalbuterol (sold as Xopenex by Sunovion), Ipratropium (sold as Atrovent by BI), Tiotropium (sold as Spiriva by BI), Salmeterol (sold as Serevent by GSK), Formoterol (sold as Foradil by Novartis and as Perforomist by Dey Pharma), Arformoterol (sold as Brovana by Sunovion), Indacaterol (sold as Arcapta by Novartis), Aclidinium (sold as Tudorza by Forest Labs), Pirbuterol (sold as Maxair by Medicis), and any combination thereof.

The present methods encompass administering one or more additional therapeutic agents to the subject in combination with a Composition of the Disclosure. In one embodiment, a Composition of the Disclosure further comprises, or the Composition is administered in combination or in alternation with, an additional therapeutic agent. That is, in some embodiments, the composition and further therapeutic agents are directed to the same locus in the same formulation, and in other embodiments, the composition can be administered via one pathway, and the further therapeutic agent(s) can be administered via a different pathway.

In some embodiments, the additional therapeutic agent comprises a cystic fibrosis transmembrane receptor (CFTR) therapy. In some embodiments, the CFTR therapy comprises a CFTR amplifer (e.g., PTI-428), a CFTR corrector (e.g., VX-809 (lumacaftor), VX-661 (tezacaftor), VX-445, VX-659, VX-152, FDL169, GLPG2222, PT-801, or combinations thereof), a CFTR potentiator/modulator (e.g., VX-770 (ivacaftor, which is approved as Kalydeco), QBW 251, VX-561, PT1-808, or combinations thereof), a CFTR RNA modifier (e.g., QR-100, MRT5005, or the combination thereof), or any combination thereof.

In some embodiments, the additional therapeutic agent comprises a CFTR amplifier. CFTR amplifiers increase the amount of CFTR protein in a cell. In cystic fibrosis, there are six mutation classes that confer differ degrees of CFTR dysfunction. The most severe cystic fibrosis mutations have a genetic defect, such as a premature stop codon, that prevent CFTR from being made into a protein. Therapies proposed to treat this mutation include amplifiers that increase the amount of CFTR RNA in a cell. These are also known as 'read-through therapies'. In some embodiments, the CFTR amplifier is PTI-428.

In some embodiments, the additional therapeutic agent comprises a CFTR corrector. CFTR correctors shuttle CFTR protein to a cell surface. The most common cystic fibrosis mutation class is Class II in which CFTR is misfolded and is not adequately transported to the cell surface. Therapies used to treat Class II mutations, such as dF508, include a combination of correctors that aid in folding the protein and/or trafficking the protein to the cell surface and potentiators that increase CFTR gating or ion transport through the protein. In some embodiments, the CFTR corrector is selected from the group consisting of VX-809 (lumacaftor), VX-661 (tezacaftor), VX-445, VX-659, VX-152, FDL169, GLPG2222, PT-801, and a combination thereof.

In some embodiments, the additional therapeutic agent comprises a CFTR Potentiator/Modulator. CFTR Potentiators/Modulators increases ion transport through CFTR on the cell surface. Classes III and IV mutations include G551D and are mutations in which CFTR has impaired gating, or ion transport. Potentiators/modulators can be used for patients with these mutations to increase the opening of the channel and allow adequate ion transport. In some embodiments, the CFTR Potentiator/Modulator is selected from the group consisting of VX-770 (ivacaftor), QBW 251, VX-561, PT1-808, and a combination thereof.

In some embodiments, the additional therapeutic agent comprises a RNA modifier. RNA modifiers can be used to enable delivery of genetically corrected CFTR to the cell surface. Classes V-VI mutations result in decreased CFTR proteins on the cell surface either via decreased CFTR transcript numbers or accelerated turnover rates. Amplifiers and RNA modifiers may be used to treat these mutations. In some embodiments, the RNA modifier is selected from the group consisting of QR-100, MRT5005, or the combination thereof.

In some embodiments, the CFTR therapy comprises a CFTR corrector (e.g., VX-809 (lumacaftor), VX-661 (tezacaftor), VX-445, VX-659, VX-152, FDL169, GLPG2222, PT-801, or combinations thereof) and a CFTR potentiator/modulator (e.g., VX-770 (ivacaftor), QBW 251, VX-561, PT1-808, or combinations thereof). In some embodiments, the CFTR therapy comprises: a combination of VX-770 (ivacaftor) and VX-809 (lumacaftor), which is approved as Orkambi; a combination of VX-770 (ivacaftor) and VX-661 (tezacaftor), which is approved as Symdeko; a combination of VX-770 (ivacaftor), VX-661 (tezacaftor), and VX-445; a combination of VX-770 (ivacaftor), and VX-659; a combination of VX-770 (ivacaftor), VX-661 (tezacaftor), and VX-152; or a combination of VX-770 (ivacaftor) and GLPG2222.

In some embodiments, the CFTR therapy comprises a CFTR corrector (e.g., VX-809 (lumacaftor), VX-661 (tezacaftor), VX-445, VX-659, VX-152, FDL169, GLPG2222, PT-801, or combinations thereof) and a CFTR amplifier (e.g., PTI-428). In some embodiments, the CFTR therapy comprises: a combination of VX-770 (ivacaftor) and VX-809 (lumacaftor), which is approved as Orkambi, and PTI-428.

In some embodiments, the CFTR therapy comprises a CFTR corrector (e.g., VX-809 (lumacaftor), VX-661 (tezacaftor), VX-445, VX-659, VX-152, FDL169, GLPG2222, PT-801, or combinations thereof). a CFTR potentiator/modulator (e.g., VX-770 (ivacaftor), QBW 251, VX-561, PT1-808, or combinations thereof), and a CFTR amplifier (e.g., PTI-428).

In some embodiments, the CFTR therapy comprises a CFTR Potentiator/Modulator and a CFTR Corrector to enhance CFTR gating/ion transport.

In some embodiments, the administration of the CFTR therapy is simultaneous or consecutive to administration of the composition of the disclosure to the subject and in any order (e.g., the composition can be administered before or after the CFTR therapy). In some embodiments, the CFTR therapy is administered orally and the composition of the disclosure is administered by inhalation. In some embodiments, both the cystic fibrosis therapy and the composition of the disclosure are administered by inhalation.

In some embodiments, the composition of the disclosure is administered in combination with VX-770, VX-809, or the combination of VX-770/VX-809, wherein the administration is simultaneous or consecutive to the subject and in any order (e.g., the composition can be administered before or after the combination of VX-770/VX-809).

The additional therapeutic agent is typically selected from drugs known as useful in treating the disease, condition, or disorder afflicting the subject in need thereof. The choice of additional therapeutic agent(s) will depend on the disease, condition, or disorder to be treated or prevented in a subject. This determination is within the capability of those skilled in the art, especially in light of the present disclosure.

In one embodiment, one additional therapeutic agent is administered to the subject. In another embodiment, two additional therapeutic agents are administered to the subject. In another embodiment, three additional therapeutic agents are administered to the subject. In another embodiment, four additional therapeutic agents are administered to the subject. In another embodiment, five additional therapeutic agents are administered to the subject. In another embodiment, five or more additional therapeutic agents are administered to the subject. Non-limiting exemplary therapeutic agents are antifungal agents, antiviral agents, antibacterial agents, anti-inflammatory agents, immunosuppressive agents, bronchodilators, airway modulators, alpha lipoic acid, alpha tocopherol, docosahexanic acid, proline, glycine, curcumin, arginine, thiocyanate, glutathione, oxidized glutathione, reduced glutathione, cysteine, hypothiocyanate, lactoferrin, and lactoperoxidase, and any combination thereof. In another embodiment, the one or more therapeutic agents are glutathione, oxidized glutathione, or reduced glutathione.

A Composition of the Disclosure and an additional therapeutic agent can be administered together as a single-unit dose or separately as multi-unit doses, wherein the Composition of the Disclosure is administered before the additional therapeutic agent, after the additional therapeutic agent, or concurrently with the additional therapeutic agent. One or more doses of the Composition of the Disclosure and/or one or more doses of the additional therapeutic agent can be administered to the subject.

In another embodiment, the additional therapeutic agent treats the desired disorder for which it is administered, but can cause certain side effects, e.g., drying of the mucosal membranes that results in discomfort and/or injury that can be addressed by administering a Composition of the Disclosure.

In another embodiment, a Composition of the Disclosure treats the desired disorder for which it is administered, but can cause certain side effects, e.g., drying of the mucosal membranes that results in discomfort and/or injury that can be addressed by administering an additional therapeutic agent.

In some embodiments, the one or more additional therapeutic agent(s) and the Composition of the Disclosure both treat the underlying disorder, though via different means, such that an additive or synergistic effect can be achieved. As a result, in some aspects of this embodiment, lower doses of the additional therapeutic agent can be effective, which lower doses can result in fewer side effects, or provide other benefits to the subject.

When a Composition of the Disclosure and one or more additional therapeutic agents are not administered concurrently, it is understood that they can be administered in any order to a subject in need thereof. For example, a Composition of the Disclosure can be administered prior to, e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before, concomitantly with, or subsequent to, e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after, the administration of one or more additional therapeutic agents to a subject in need thereof. In some embodiments, a Composition of the Disclosure and the one or more additional therapeutic agents are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, or no more than 48 hours apart. In one embodiment, the components of the combination therapies are administered at about 1 minute to about 24 hours apart.

In another embodiment, the additional therapeutic agent is an inhaled corticosteroid (ICS) or bronchodilator.

Prophylaxis

In addition to providing methods of treatment, the Compositions of the Disclosure can also be used to reduce the symptoms of or provide prevention of various diseases and disorders associated with a bacterial clinical isolate infection, impaired mucociliary clearance, and/or airway inflammation.

Embodiments of the present disclosure can be further defined by reference to the following non-limiting examples, which describe in detail preparation of certain compositions of the present disclosure and methods for using compositions of the present disclosure. It will be apparent to those skilled in the art that many modifications, both to materials and methods, can be practiced without departing from the scope of the present disclosure.

In Vitro Analysis of Clinical Isolate Bacteria

Clinical isolate samples from a subject can include, but are not limited to, sputum, airway samples, surgical tissue samples, autopsy samples, and blood. Samples can be fixed and/or stored at −20° C. or −80° C.

Isolation of CI species of clinical isolate bacteria can be accomplished by any technique known in the art. Species of CIs can be isolated from pure cultures (i.e., having only one CI species) or from a sample with multiple bacteria. Common methods to isolate species of CIs include, but are not limited to, serial dilution of initial clinical sample, centrifugation, plate-streaking with or without an initial growth step in liquid medium, and growth of individual colonies of bacteria on a solid or liquid medium. CIs are grown using any media known in the art, including but not limited to, planktonic and solid media.

Clinical isolate bacteria can be identified using any technique known in the art including, but not limited to morphological techniques (e.g., Gram staining, acid fast stains); biochemical, serological, or protein expression tests (e.g., interaction with antibodies, slide agglutination, ELISA, Western blotting, immunohistochemistry, immunofluorescence, flow cytometry); phage typing; and DNA- and/or RNA-based methods (e.g., DNA sequencing, G+C comparisons, gPCR, RT-PCR, qPCR, rRNA sequencing, DNA fingerprinting by restriction fragment length polymorphisms (RFLPs), nucleic acid hybridization (e.g., Northern blotting, Southern blotting), microarrays, in situ hybridization, including FISH).

Growth of clinical isolates in the presence of a drug (e.g., an antibiotic) with or without the composition of the disclosure, in the absence of a drug with or without the composition of the disclosure, or a placebo with or without the composition of the disclosure can be tested using any technique known in the art including, but not limited to, dilution and time-lapsed growth of CIs; identification of minimum inhibitory concentrations (MICs); determination of minimum biofilm eliminating concentration (MBC); and other methods known in the art (e.g., disk diffusion method, E-test (AB Biodisk, Solna, Sweden), any commercially available automated susceptibility testing system (e.g., the Vitek System (bioMerieux, France), the Walk-Away System (Dade International, Sacramento, CA), enzyme (e.g., beta lactamase)). Growth of CIs is tested in planktonic or biofilm cultures.

In some aspects, the present disclosure includes measurement of the minimum inhibitory concentrations (MICs). MICs can be determined on MUller-Hinton (MH) agar plates or in planktonic cultures by broth microdilution in MH. MICs can be determined for clinical isolate strains and/or lab-type reference strain PAO1. In some embodiments, the clinically efficacious MIC range of the composition is about 1%-50%, about 1%-40%, about 5%-50%, about 5%-40%, about 5%-35%, about 10%-50%, about 10%-40%, about 10%-35%, or about 12%-32%.

In some aspects, the present disclosure includes measurement of biofilm formation in vitro for clinical isolate bacteria. In some embodiments, an overnight culture of bacteria is grown in LB with and without the composition of the disclosure with shaking. The culture is then diluted 1:100, and 100-L aliquots added to a 96-well plate, which are incubated for 72 h at 37° C. to allow for the adequate growth of the clinical isolates. After two to three washes with water, crystal violet is added for 15 min followed by three rinses with water then the addition of 95% ethanol. The materials are then transferred to a fresh 96-well plate, and absorbance at 540 nm determined.

In some aspects, the present disclosure includes measurement of the minimum biofilm eliminating concentration (MBC) of CIs. For the minimum biofilm concentrations (MBC), a protocol similar to the MIC protocol can be used except the bacteria is seeded on a plate used for bacterial adherence. In some embodiments, optical densities are measured to determine the MBC for bacterial isolate. In some embodiments, the assay involves the formation of 96 identical biofilms on plastic pegs on the lid of an MBC device. Biofilms are then exposed to test antibiotics for a defined time period, then placed in fresh bacteriologic medium in a second 96-well plate and incubated overnight. The MBC value is the lowest dilution that prevents regrowth of bacteria from the treated biofilm.

The present disclosure allows for any of the above techniques in the presence or absence of nitrate.

The present disclosure allows for any of the above techniques in the presence or absence of oxygen.

The present disclosure allows for any of the above techniques in the presence or absence of one or more antibiotics.

EXAMPLES

It is understood that the examples and embodiments described herein are for illustrative purposes only and that various modifications or changes in light thereof will be suggested to persons skilled in the art and are to be included within the spirit and purview of this application.

Example 1

Stability: Measuring Reduced Glutathione and Ascorbic Acid Levels

Composition 1 was prepared with 150 mg/ml glutathione, 88 mg/ml ascorbic acid and 84 mg/ml sodium bicarbonate based on 322 total mg/ml weight, which corresponds to % total weight of about 46.6%, 27.3% and 26.1%, respectively. The molar ratio of the components in Composition 1 were 0.49 M glutathione, 0.50 M ascorbic acid, and 1 M $HCO_3$.

Composition 2 was prepared with 150 mg/ml glutathione, 126 mg/ml ascorbic acid and 84 mg/ml sodium bicarbonate based on 360 total mg/ml weight, which corresponds to % total weight of about 33%, 38.9% and 28.9%, respectively. The molar ratio of the components in Composition 1 were 0.49 M glutathione, 1 M ascorbic acid, and 1 M $HCO_3$.

The amount of glutathione and ascorbic acid oxidation were determined for Composition 1 at pH 5.5, 6.0, and 6.5. Oxidized glutathione is associated with the generation of protein-carbonyls via glutathionlyation, which occurs when oxidized glutathione dissociates and attaches to proteins. The % oxidized glutathione (% GSSG) was determined after 4 weeks of storage of Composition 1 at pH 5.5, 6.0, and 6.5under $N_2$-sparged and ambient conditions. Additionally, when ascorbic acid is oxidized into dehydroascorbate (DHA), DHA can break down and result in the formation of protein adducts in process called ascorbylation (Simpson et al., Biochim biophys Acta 2000; 1501:12-24). The % reduced ascorbic acid maintained in Composition 1 (% ASC) was determined after 4 weeks of storage of Composition 1 at pH 5.5, 6.0, and 6.5 under $N_2$-sparged (anaerobic) and ambient conditions. Specifically, nitrogen-sparged samples were mixed under anaerobic conditions sparged with nitrogen, and the samples were packaged using nitrogen bubbling. Ambient samples were mixed under room air conditions and were not bubbled with nitrogen. The formulations were stored at 5° C. for 4 weeks, and the percent of oxidized glutathione (GSSG) and ascorbic acid (ASC) was measured for each sample according to standard techniques.

As shown in Table 2, oxidation of glutathione and ascorbic acid is pH- and oxygen-dependent, and the presence of glutathione increases the concentration of reduced ascorbic acid after 4 weeks of storage at 5° C. Moreover, when oxygen is present in solution, reduced glutathione (GSH) helped maintain ascorbic acid concentration, but the GSH is itself oxidized to GSSG in greater concentrations. These results demonstrate that the pH of Composition 1 is important for maintaining glutathione and ascorbic acid in their reduced state, and that the molar ratios of glutathione and ascorbic acid in Composition 1 further stabilizes the oxidation rates of both glutathione and ascorbic acid.

TABLE 1

| Formulation | pH | Atmosphere | % GSSG | % ASC |
| --- | --- | --- | --- | --- |
| Formulation 1 | 5.5 | $N_2$-sparged | 2.86 | 89.47 |
| Formulation 2 | 6.0 | $N_2$-sparged | 6.54 | 91.20 |
| Formulation 3 | 6.5 | $N_2$-sparged | 9.11 | 91.27 |
| Formulation 4 | 5.5 | Ambient | 6.44 | 90.66 |
| Formulation 5 | 6.0 | Ambient | 15.97 | 90.25 |
| Formulation 6 | 6.5 | Ambient | 19.94 | 91.25 |
| Ascorbic Acid Only | | Ambient | | 77.88 |

Example 2

In Vitro Minimal Inhibitory Concentration (MIC) of Glutathione Compositions Against Bacterial Clinical Isolates Composition 1 was prepared with 150 mg/ml glutathione, 88 mg/ml ascorbic acid and 84 mg/ml sodium bicarb based on 322 total mg/ml weight, which corresponds to % total weight of about 46.6%, 27.3% and 26.1%, respectively. The molar ratio of the components in Composition 1 were 0.49 M glutathione, 0.50 M ascorbic acid, and 1 M $HCO_3$.

The MICs of Composition 1 (glutathione, ascorbic acid, and $HCO_3$); glutathione and ascorbic acid; and $HCO_3$ were tested against clinical isolates, including *Burkholderia cepacia, Pseudomonas aeruginosa* (Schroeter) Migula (ATCC 27853), *Pseudomonas aeruginosa* (Schroeter) Migula (ATCC 9027), *Pseudomonas aeruginosa* (Schroeter) Migula (ATCC BAA-2114), *Klebsiella pneumonia*, methicillin resistant *Staphylococcus aureus*; laboratory strains of *Moraxella catarrhalis, Stenotrophomonas maltophilia, Acinetobacter baumannii*; and eight samples of mucoid and nonmucoid *Pseudomonas aeruginosa* clinical isolates from human lung. The MIC for laboratory clinical isolate *Pseudomonas aeruginosa* (Schroeter) Migula (ATCC BAA-47 (PAO1)) was also tested. The MICs were determined under anaerobic conditions on media supplemented with nitrate, under aerobic conditions supplemented with nitrate, or under ambient conditions.

The clinical isolates were inoculated in duplicate on agar plates overnight under anaerobic conditions at 36° C.±1.0° C. in a 96-well plate. Laboratory isolates of *Burkholderia cepacia* were also grown in duplicate overnight under aerobic conditions at 36° C.±1.0° C. in a 96-well plate. Colonies from each clinical isolate grown on the agar plates then were chosen to inoculate 96-well plates in duplicate and were tested under three test solution conditions: Composition 1 (glutathione, ascorbic acid, and HCO$_3$); glutathione and ascorbic acid; and HCO$_3$ were diluted and added to the media. Ten dilutions for each test solution were examined: 50%, 25%, 12.5%, 6.25%, 3.13%, 1.57%, 0.78%, 0.39%, 0.2%, and 0.1%. The colony isolates were incubated for 12 hours or 24 hours at 36° C.±1.0° C. under anaerobic conditions in media comprising Luria Agar/Broth and nitrate with one of the three test solutions. In an additional test, *Burkholderia cepacia* and *Klebsiella pneumoniae* were grown in aerobic media comprising only Luria Agar/Broth with Composition 1. The MIC of Composition 1 was also determined for certain *Pseudomonas aeruginosa* lab and clinical isolates, *Moraxella catarrhalis, Stenotrophomonas maltophilia, Acinetobacter baumannii*, and *Burkholderia cepacia* grown under aerobic conditions comprising 1% nitrate. MICs were determined via visual inspection and OD$_{620}$. The MICs at 12, 24, and/or 48 hours in the clinical isolates tested are listed in Table 2.

TABLE 2

| | Anaerobic (+nitrate) | | | Aerobic (+nitrate) | Aerobic (Ambient) |
|---|---|---|---|---|---|
| Organism | Composition 1 | GSH + ASC | HCO3 | Composition 1 | Composition 1 |
| Bc 25416 | 25% (24 hrs); 6.25% (48 hours) | | | 6.25% (12 hours) | 3.13% (12 hrs); 25% (24 hrs) |
| Kp 4352 | 25% (12 hrs); 25% (24 hrs) | | | 50% (12 hrs); 50% (24 hrs) | |
| Pa 27853 | 12.5% (12 hrs); 12.5% (24 hrs) | | | | |
| Pa 9027 | 6.25% (12 hrs); 25% (24 hrs) | 6.25% (12 hrs) | | | |
| Pa BAA-2114 | 3.13% (12 hrs) | 0.39% (12 hrs) | | | |
| Pa BAA-47 (PAO1) | 6.25% (12 hrs) | 0.39% (12 hrs) | 12.5% (12 hrs) | 6.25% (12 hours) | |
| Pa UAB-NM-1 | 12.5% (12 hrs) | 0.78% (12 hrs) | 12.5% (12 hrs) | 1.56% (12 hours) | |
| Pa UAB-M-2 | 6.25% (12 hrs) | 0.39% (12 hrs) | 12.5% (12 hrs) | 3.13% (12 hours) | |
| Pa UAB-NM-3 | 6.25% (12 hrs) | 0.78% (12 hrs) | 12.5% (12 hrs) | | |
| Pa UAB-4 | 6.25% (12 hrs) | | | | |
| Pa UAB-NM-5 | 6.25% (12 hrs) | 0.78% (12 hrs) | 12.5% (12 hrs) | | |
| MRSA UAB-1 | 12.5% (12 hrs) | 0.39% (12 hrs) | 25% (12 hrs) | | |
| MRSA UAB-2 | 25% (12 hrs) | 0.39% (12 hrs) | | | |
| MRSA UAB-3 | 6.25% (12 hrs) | 0.39% (12 hrs) | 25% (12 hrs) | | |
| MRSA UAB-4 | 25% (12 hrs) | 0.39% (12 hrs) | | | |
| Mc ATCC 25238 | | | | 1.56% (12 hours) | |
| Sm ATCC 13636 | | | | 6.25% (12 hours) | |
| Ab ATCC 19606 | | | | 6.25% (12 hours) | |

Bc: *Burkholderia cepacia*
Kp: *Klebsiella pneumonia*
Pa: *Pseudomonas aeruginosa*
Pa UAB: *P. aeruginosa* clinical isolates from lung
MRSA: Methicillin-resistant *Staphylococcus aureus*
Mc: *Moraxella catarrhalis*
Sm: *Stenotrophomonas maltophilia*
Ab: *Acinetobacter baumannii*
NM: Nonmucoidy
M: Mucoidy An in vitro assay for MIC, i.e., the lowest concentration of a test substance or drug that inhibits bacterial growth, can be measured by optical density or visualization of no growth. MIC is often used to indicate the efficacy of an antibacterial drug. A lower MIC generally corresponds to a more potent drug.

The results show that Composition 1 inhibits bacteria even though the bicarbonate in the solution decreased the efficacy of glutathione in vitro. MIC for bicarbonate alone was measured for representative bacterial isolates to determine the contribution of bicarbonate to the inhibition in vitro.

The results show that Composition 1 was clinically efficacious against *Pseudomonas aeruginosa* lab and clinical isolates, *Burkholderia cepacia, Klebsiella pneumoniae*, methicillin resistant *Staphylococcus aureus, Moraxella catarrhalis, Stenotrophomonas maltophilia*, and *Acinetobacter baumannii*. Notably, lab and clinical isolate *Pseudomonas aeruginosa* phenotypes can vary dramatically based on the conditions under which they are maintained, their passage number and the environment from which they were isolated. Therefore, PAO1 is not predictive of how other lab or clinical isolates will be inhibited.

The anaerobic and aerobic effects on *B. cepacia* and *K pneumoniae* were also assessed in vitro. Both of these bacteria are especially tenacious and are difficult to inhibit, even at high concentrations of antibacterial agents. They are both associated with clinical decline in chronic inflammatory airways diseases. For *B. cepacia*, the inhibitory effect lasted over a 48 hour period.

Composition 1 was also able to effectively inhibit MRSA in vitro. This was unexpected due to the high salt concentration of Composition 1 because MRSA generally thrives under high salt concentrations.

Composition 1 was also able to effectively inhibit a mucoid clinical isolate of *Pseudomonas aeruginosa* (Pa UAB-M-4). A mucoid phenotype is associated with multi-drug resistance and clinical decline in patients with chronic inflammatory airways diseases.

Composition 1 was also able to effectively inhibit *Burkholderia cepacia, Moraxella catarrhalis, Stenotrophomonas maltophilia*, and *Acinetobacter baumannii* under aerobic conditions with 1% nitrate. Each of these bacteria has been recognized as an emerging pathogen.

Example 3

In Vitro Analysis of Mucociliary Transport Rate in dF508−/− Primary Human Bronchial Epithelial Cells The ability of Composition 1 (as prepared in Example 1) to affect the mucociliary transport (MCT) rate of primary human bronchial epithelial cells isolated from cystic fibrosis patients was assessed in vitro. Mucociliary transport rate provides one measurement of mucociliary clearance, which is the mechanism by which epithelial cells clear mucus from the airway.

Briefly, primary human bronchial epithelial cells were isolated from the airways of patients with cystic fibrosis and were terminally differentiated. All cells isolated from cystic fibrosis patients were represented by the dF508−/− genotype. Cells were incubated with phosphate-buffered saline (PBS), a high concentration (25%) of Composition 1, or a low (12.5%) concentration of Composition 1. Micro-optical coherence tomography (uOCT) was used to assess the mucociliary transport rate according to methods described in Liu, L., et al., PLoS One. 2013; 8(1): e54473. The ratio of glutathione to ascorbic acid to bicarbonate salt in Composition 1 was 150 mg/ml glutathione:88 mg/ml ascorbic acid:84 mg/ml bicarbonate salt, which is represented by a molar ratio of 0.5 mol glutathione:0.5 mol ascorbic acid:1 mol bicarbonate.

Figure 1:
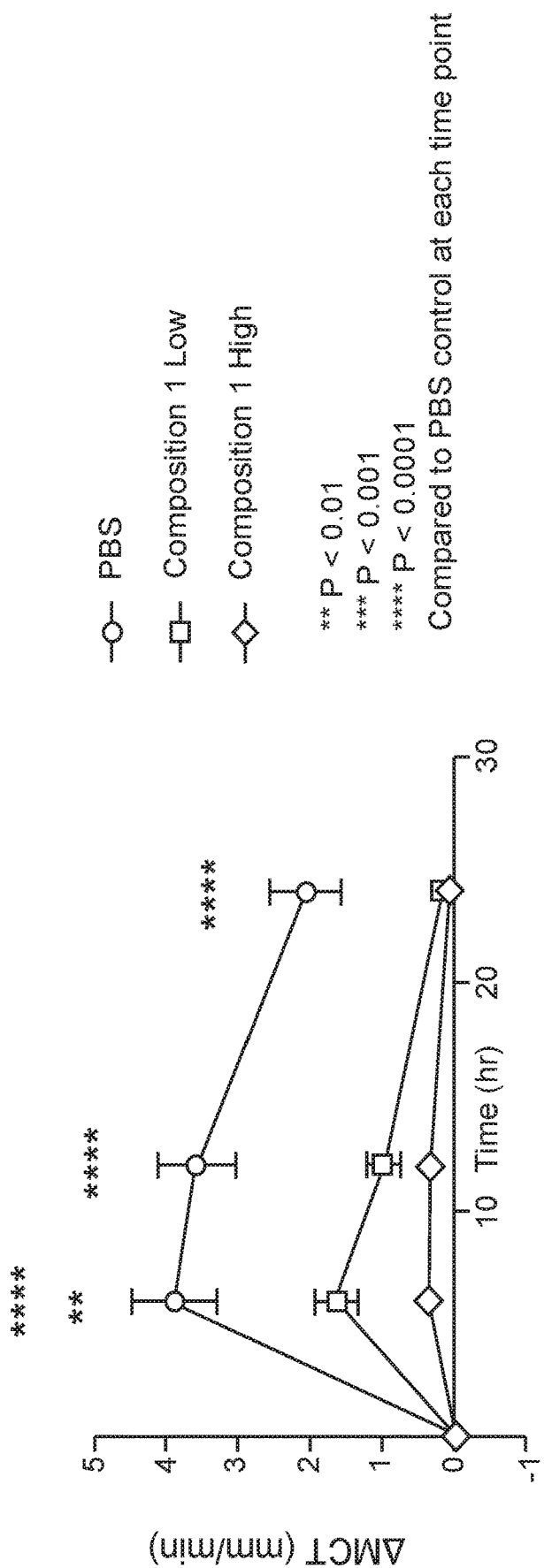
FIG. 1 shows the mucociliary transport rate of primary human bronchial epithelial cells (df508−/−) isolated from the airways of patients with cystic fibrosis following administration of Composition 1.

As shown in FIG. 1, incubation with Composition 1 increased the mucociliary transport of dF508−/− primary human bronchial epithelial cells compared to incubation with a PBS control. Additionally, at all time points tested, incubation with a high concentration of Composition 1 resulted in increased mucociliary transport rate compared to incubation with a low concentration of Composition 1. These data demonstrate that Composition enhances the mucociliary transport of primary human bronchial epithelial cells in a dose-dependent manner.

Example 4

In Vitro Analysis of Mucociliary Transport Rate in dF508−/− Primary Human Bronchial Epithelial Cells The mucociliary transport rate of dF508−/− primary human bronchial epithelial cells following administration of isolated components of Composition 1 (as prepared in Example 1) was assessed in vitro. As described above in Example 2, primary human bronchial epithelial cells were isolated from the airways of patients with cystic fibrosis, and uOCT was used to assess the mucociliary transport rate according to methods described in Liu, L., et al., PLoS One. 2013; 8(1): e54473. Cells were incubated with Composition 1, bicarbonate, glutathione, bicarbonate +glutathione, or bicarbonate +ascorbate prior to analysis via uOCT.

Figure 2:
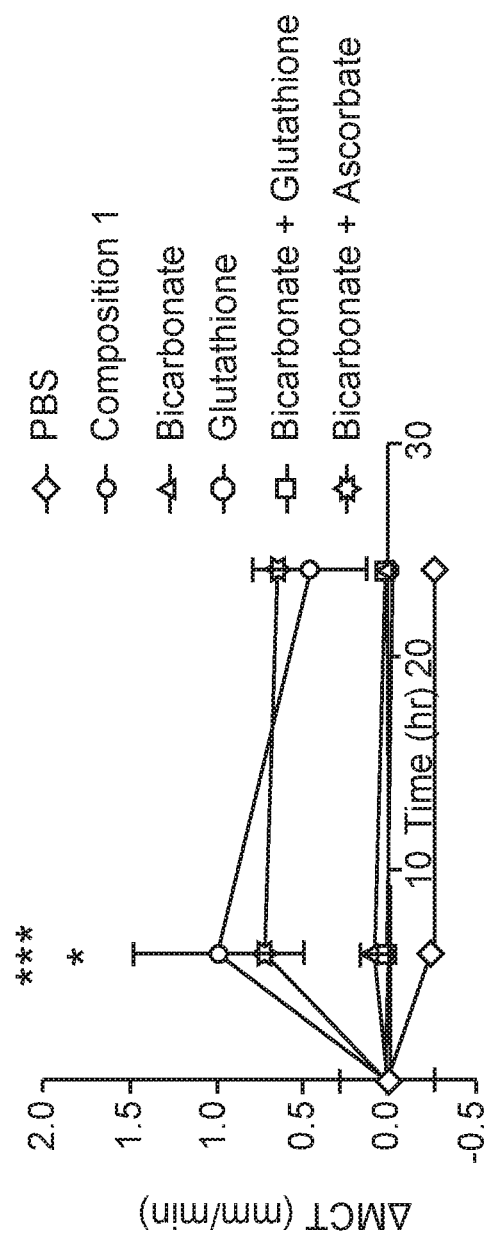
FIG. 2 shows the mucociliary transport rate of primary human bronchial epithelial cells (df508−/−) isolated from the airways of patients with cystic fibrosis following administration of Composition 1, bicarbonate, glutathione, bicarbonate+glutathione, or bicarbonate+ascorbate.

As shown in FIG. 2, incubation of dF508−/− primary human bronchial epithelial cells with Composition 1 increased their mucociliary transport rate compared to incubation with a PBS control, a solution containing only bicarbonate, a solution containing only glutathione, or a solution containing glutathione and bicarbonate. Incubation of cells with solutions containing only glutathione, only bicarbonate, or a combination of glutathione and bicarbonate did not alter the mucociliary transport rate compared to incubation with a PBS control. These data demonstrate that solutions containing only glutathione and bicarbonate (alone or in combination) do not have a significant effect on mucociliary transport rate, while Composition 1 enhanced the mucociliary transport of primary human bronchial epithelial cells isolated from cystic fibrosis patients.

Example 5

In Vitro Analysis of Neutrophil Extracellular Trap (NET) Formation in Human Neutrophils Composition 2 was prepared with 150 mg/ml glutathione, 126 mg/ml ascorbic acid and 84 mg/ml sodium bicarbonate based on 360 total mg/ml weight, which corresponds to % total weight of about 33%, 38.9% and 28.9%, respectively. The molar ratio of the components in Composition 1 were 0.49 M glutathione, 1 M ascorbic acid, and 1 M $HCO_3$.

The ability of Composition 2 to control the formation of neutrophil extracellular traps (NETs) from human neutrophils was assessed in vitro. NETs are defined as the release of myeloperoxidase (MPO), DNA strands, and other pro-inflammatory components (e.g., neutrophil elastase) from neutrophils, and NETs contribute to inflammation and infection in chronic inflammatory airway diseases (see, e.g., Martinez-Aleman, Front Cell Infect Microbiol. 2017; 7:104).

Briefly, neutrophils were isolated from healthy volunteers and incubated with phorbol myristate acetate (PMA) (50 mM) or a control solution for three hours. Cells were then incubated with dilutions of Composition 1, or Composition 2 and stained with DAPI (4',6-diamidino-2-phenylindole) to detect extracellular DNA release and MPO was detected. Images of NET formation were obtained by fluorescence microscropy.

Figure 3:
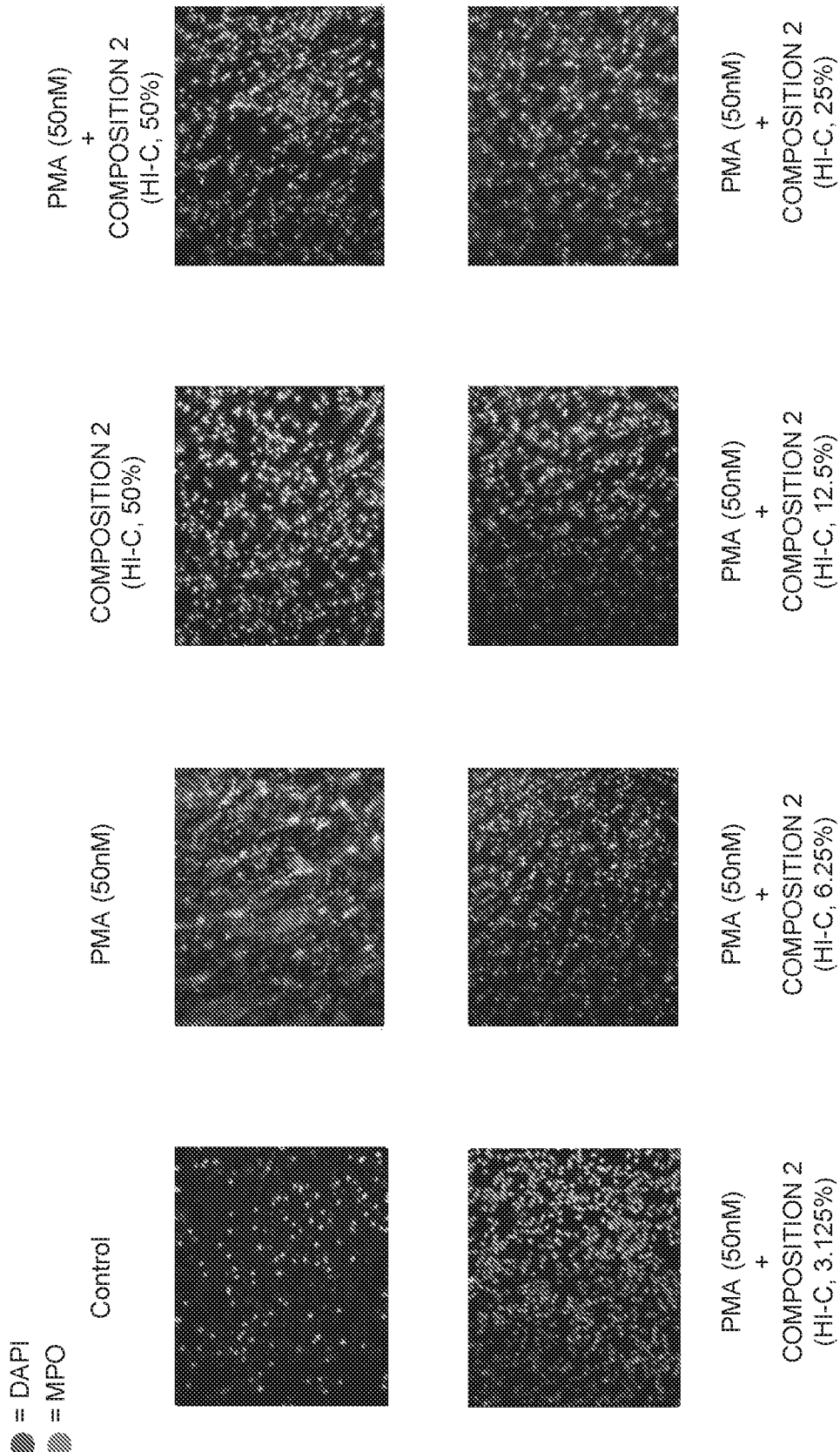
FIG. 3 shows NETosis staining of human neutrophils isolated from healthy volunteers following administration of phorbol myristate acetate (PMA) and Composition 2.

As shown in FIG. 3, neutrophils incubated with PMA alone showed extensive NET formation, while neutrophils incubated with Composition 2 showed a marked reduction in NET formation. In particular, neutrophils incubated with a solution containing 50% dilution of Composition 2 showed the lowest amount of NET formation following stimulation with PMA, while neutrophils incubated with increasingly dilute solutions of Composition 2 (25%, 12.5%, 6.25%, and 3.125%) showed less decrease in the amounts of NET formation. These data demonstrate that Composition 2 decreased NET formation from human neutrophils in a dose-dependent manner.

Example 6

In Vitro Analysis of Nitric Oxide (NO) Release from Human Neutrophils

The release of nitric oxide (NO) from human neutrophils following administration of Composition 1 (as prepared in Example 1) was assessed in vitro. NO is released from neutrophils in chronic inflammatory airway diseases and is associated with increased pulmonary infections and inflammation due to the conversion of NO to nitrates and nitrates (see, e.g., Francoeur, C. and Denis, M. Inflammation (1995) 19: 587).

Briefly, neutrophils were isolated from healthy volunteers, incubated with 10 µg/ml lipopolysaccharide (LPS) or a control solution, and incubated with various dilutions of Composition 1. Cells were stained with DAF-FM diacetate to detect NO, and images of NO release were obtained by fluorescence microscopy.

Figure 4:
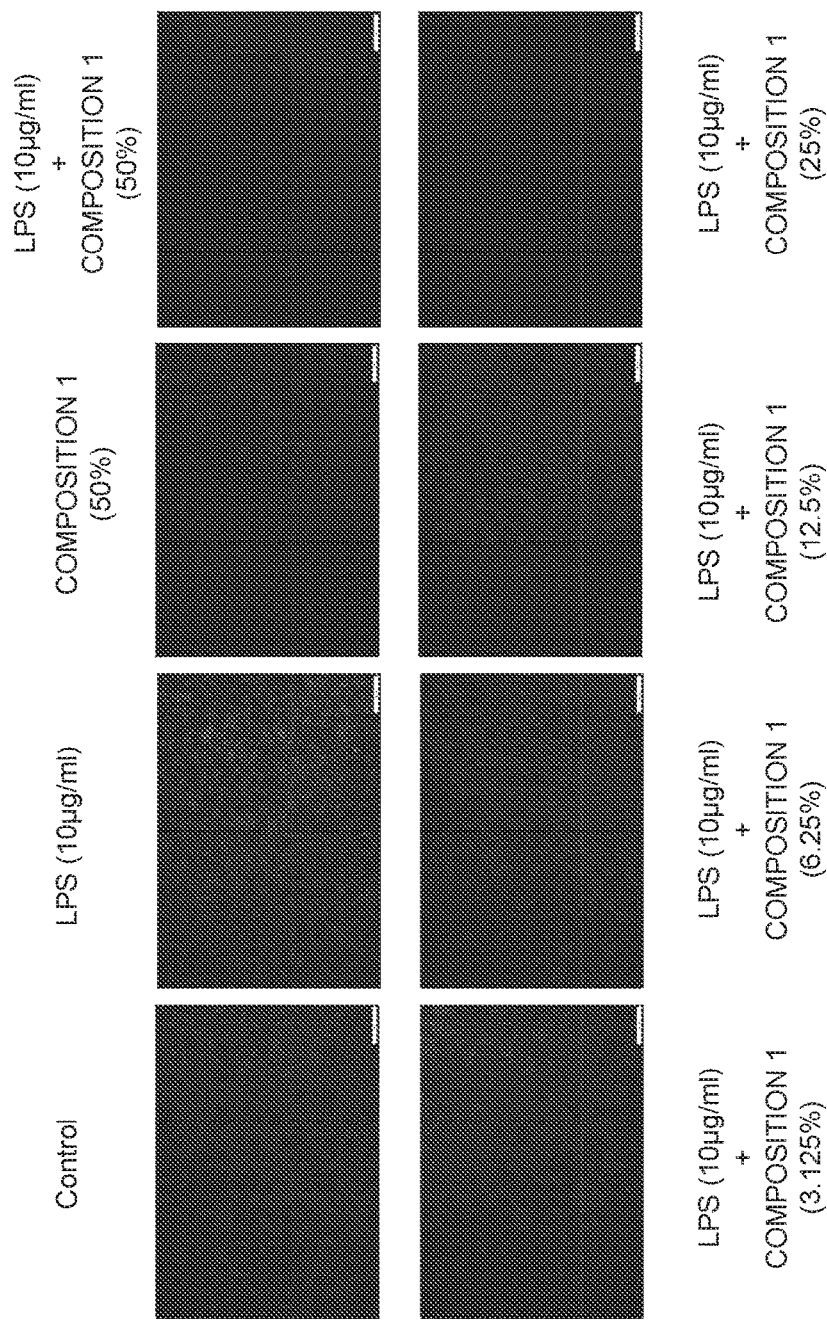
FIG. 4 shows DAF-FM diacetate staining for nitric oxide in human neutrophils following administration of lipopolysaccharide (LPS) and Composition 1.

As shown in FIG. 4, neutrophils incubated with LPS alone showed extensive release of NO, while neutrophils incubated with Composition 1 showed a marked reduction in NO release. In particular, neutrophils incubated with a solution containing 50% dilution of Composition 1 showed the lowest amount of NO release following stimulation with LPS, while neutrophils incubated with increasingly dilute solutions of Composition 1 (25%, 12.5%, 6.25%, and 3.125%) showed less decrease in the amounts of NO release. These data demonstrate that Composition 1 decreases NO release from human neutrophils in a dose-dependent manner.

Example 7

Clinical Study of Nitric Oxide (NO) Exhaled from a Bilateral Lung Transplant Patient The effect of Composition 1 (as prepared in Example 1) on pathological exhaled NO was assessed in a human patient in vivo. Briefly, measurements of fractional exhaled nitric oxide (FeNO) were taken from a bilateral lung transplant patient prior to administration of Composition 1 and again immediately following administration of Composition 1 using standard techniques (see, e.g., Fisher, Thorax 1998; 53:454-458; Gabbay, Am J Respir Crit Care Med 2000; 162: 2182-2187; Kharitonov, The Lancet 1994; 343 (8890): 133-135; and Hubert, European Respiratory Journal 2009 34: 117-124). While the patient exhibited a FeNO measurement of 119 ppb prior to administration of Composition 1, the patient's FeNO measurement decreased to 24 ppb immediately following administration of Composition 1. In some patients, normal levels of NO are considered to be 20-50 ppb, and NO levels above 50 ppb are associated with infection and inflammation. Accordingly, the patient exhibited a reduction from a pathological level of NO to a normal level of NO following a single treatment with Composition 1. These results were reproducible (data not shown). These data demonstrate the acute positive impact of Composition 1 on decreasing the level of exhaled NO in lung transplant patients.

Example 8

In Vitro Inflammatory Cytokine Analysis of Human Neutrophils

Inflammatory cytokine assays were performed in vitro with human neutrophils following administration of dilutions of Composition 1. Briefly, polymorphonuclear leukocytes (PMNs) were adjusted to a density of $4 \times 10^6$/ml in DMEM (Gibco 11995-065) without fetal bovine serum (FBS), and 0.25 ml of the resulting solution was added to duplicate wells of a 24-well plate ($1 \times 10^6$ PMN/2-cm$^2$ well). The cells were then pretreated with 0.25 ml of 3.125%, 6.25%, 12.5%, 25%, and 50% dilutions of a 2× dose of Composition 1 (88 mg/ml vitamin C) for 1 hour at 37° C. Half of the wells were then spiked with 100× E. coli 0111:B4 LPS (Sigma L4391) at 5 µl/well and incubated for 4 hours at 37° C. Conditioned media was collected from the wells and frozen for batch cytokine analysis. Quantification of human IL-6, human IL-8/CXCL8, and human TNF-α in conditioned media was performed under standard conditions using R&D Systems Quantikine ELISA kits.

Figure 5A:
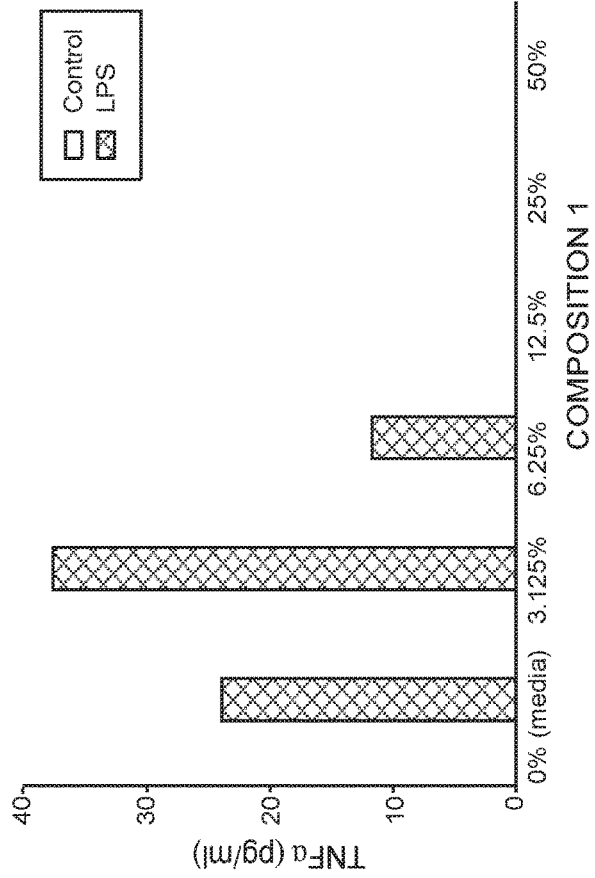
Figure 5B:
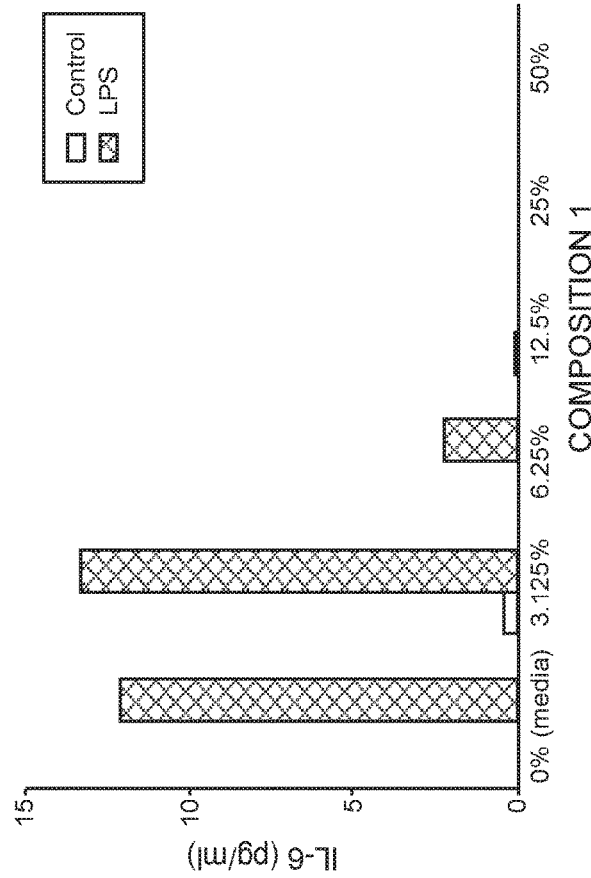

As shown in Table 3 and FIGS. 5A-5C, human neutrophils stimulated with LPS and incubated with dilutions of Composition 1 secreted significantly lower amounts of pro-inflammatory cytokines compared to those incubated with a control (media alone). In particular, neutrophils stimulated with LPS and incubated with media alone exhibited a TNF-α concentration of 23.8 pg/ml, while neutrophils incubated with 12.5% Composition 1, 25% Composition 1, or 50% Composition 1 did not produce any detectable TNF-α (Table 3 and FIG. 5A). Neutrophils incubated with 6.25% Composition 1 exhibited a TNF-α concentration of 11.7 pg/ml, about half that of neutrophils incubated with media alone (Table 3 and FIG. 5A). Similarly, neutrophils stimulated with LPS and incubated with 50% Composition 1, 25% Composition 1, or 12.5% Composition 1 did not produce any detectable levels of IL-6, while neutrophils incubated with 6.25% Composition 1 exhibited about a 6-fold reduction in the level of IL-6 compared to neutrophils incubated with media alone (Table 3 and FIG. 5B). Moreover, neutrophils stimulated with LPS and incubated with 50% Composition 1, 25% Composition 1, or 12.5% Composition 1 did not produce any detectable levels of IL-8, while neutrophils incubated with 6.25% Composition 1 exhibited about a 3-fold reduction in the level of IL-8 compared to neutrophils incubated with media alone (Table 3 and FIG. 5C). These data demonstrate that administration of Composition 1 results in a dose-dependent downregulation of pro-inflammatory cytokines implicated in chronic inflammatory diseases such as cystic fibrosis, lung transplant, and chronic obstructive pulmonary disease.

TABLE 3

| LPS Treatment | Composition 1 Treatment | IL-6 (pg/ml) | IL-8 (pg/ml) | TNF-α (pg/ml) |
| --- | --- | --- | --- | --- |
| Control | media | 0.0 | 289.0 | 0.0 |
| Control | 50% Composition 1 | 0.0 | 1.0 | 0.0 |
| Control | 25% Composition 1 | 0.0 | 0.0 | 0.0 |
| Control | 12.5% Composition 1 | 0.1 | 0.0 | 0.0 |
| Control | 6.25% Composition 1 | 0.0 | 130.0 | 0.0 |
| Control | 3.125% Composition 1 | 0.4 | 315.0 | 0.0 |
| LPS | media | 12.1 | 1993.0 | 23.8 |
| LPS | 50% Composition 1 | 0.0 | 0.0 | 0.0 |
| LPS | 25% Composition 1 | 0.0 | 0.0 | 0.0 |
| LPS | 12.5% Composition 1 | 0.0 | 0.0 | 0.0 |
| LPS | 6.25% Composition 1 | 2.2 | 643.0 | 11.7 |
| LPS | 3.125% Composition 1 | 13.3 | 1808.0 | 37.5 |

Example 9

Cystic Fibrosis Transmembrane Conductance Receptor (CFTR) Functional Assay

As shown in FIG. 6, Composition 1 (as prepared in Example 1) enhances Isc (µA/cm$^2$) in wild-type cystic fibrosis bronchial epithelial cells in a cystic fibrosis transmembrane conductance receptor (CFTR) assay.

Example 10

Figure 7:
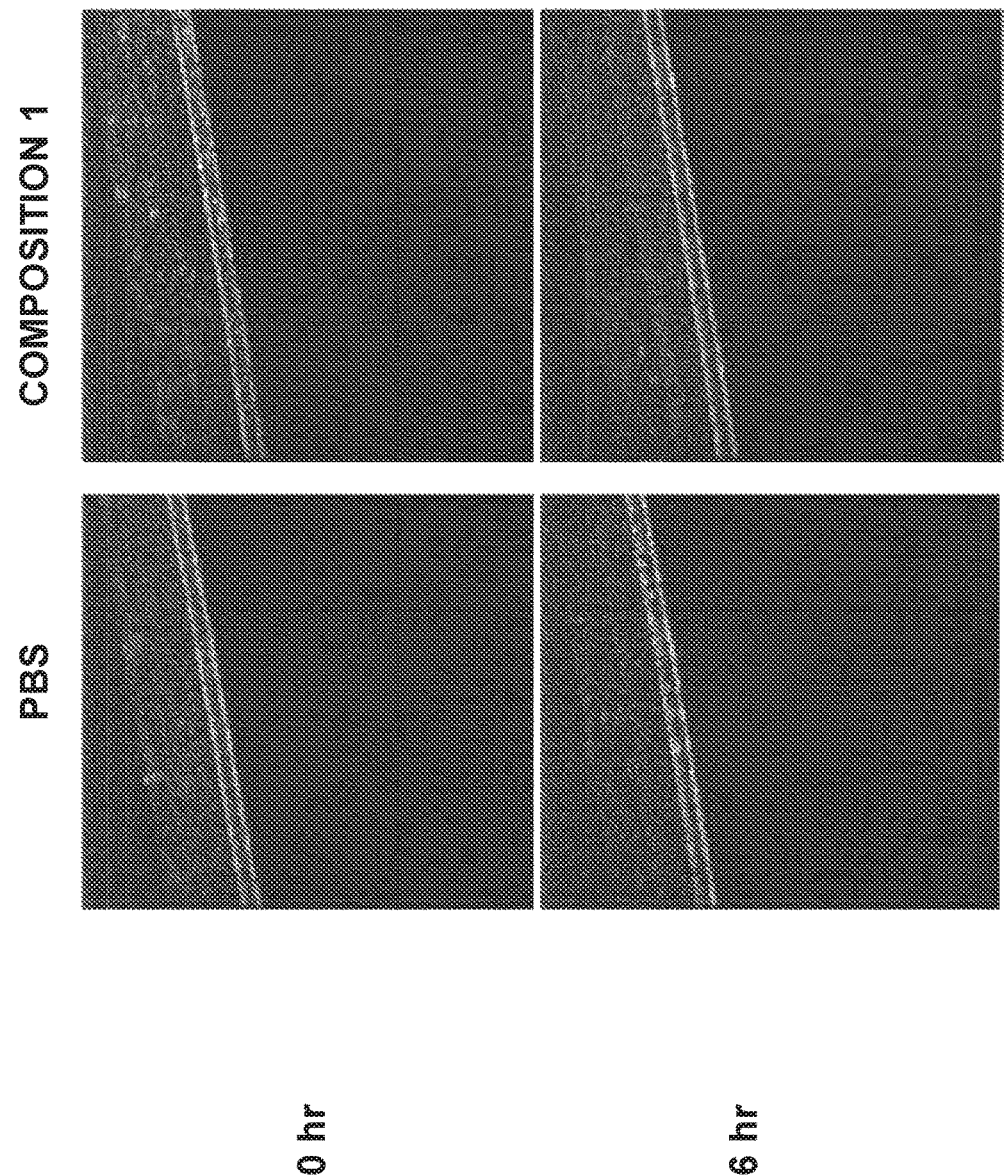
FIG. 7 shows an image from a video showing the effect of Composition 1 (right panels) compared to PBS (left panels) on the in vitro mucociliary transport (MCT) rate of primary human bronchial epithelial cells isolated from cystic fibrosis patients (dF508−/− cells) at 0 hours (top) and 6 hours (bottom) after administration.

In Vitro Analysis of MCT Rate, ASL and CBF in dF508-/- Primary Human Bronchial Epithelial Cells MCT rate was assessed in a mucociliary clearance assay according to the methods in Example 3 above. Images from a video showing the effect of Composition 1 on the functional microanatomy of the primary human bronchial epithelial cells isolated from cystic fibrosis patients (dF508-/- cells) at 0 and 6 hours after administration is shown FIG. 7. These results showed that Composition 1 enhanced MCT rate compared to PBS control 6 hours after administration.

Figure 8A:
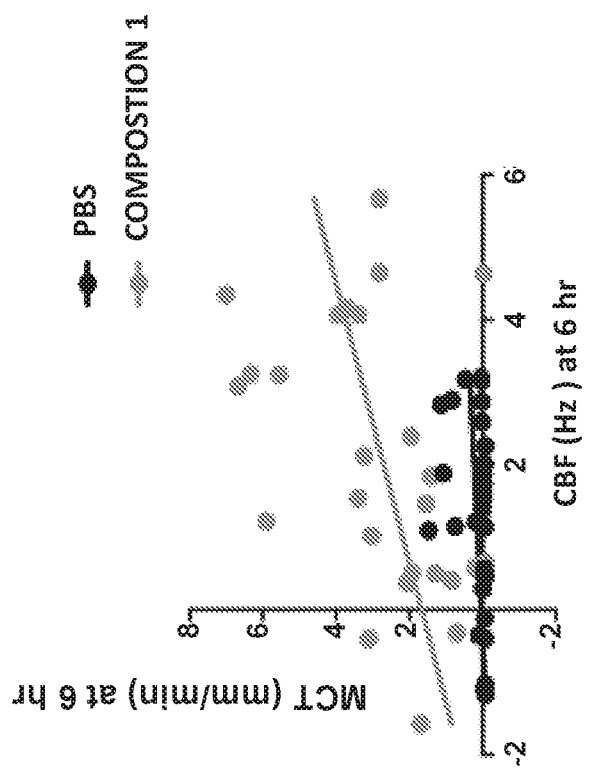
FIG. 8A-8B show slope analysis of MCT relative to airway surface liquid (ASL) (FIG. 8A) and ciliary beat frequency (CBF) (FIG. 8B) at 6 hours after administration of Composition 1 compared to PBS in primary human bronchial epithelial cells isolated from cystic fibrosis patients (dF508−/− cells). This correlation analysis indicates that mucus viscosity is decreased by Composition 1.
Figure 8B:
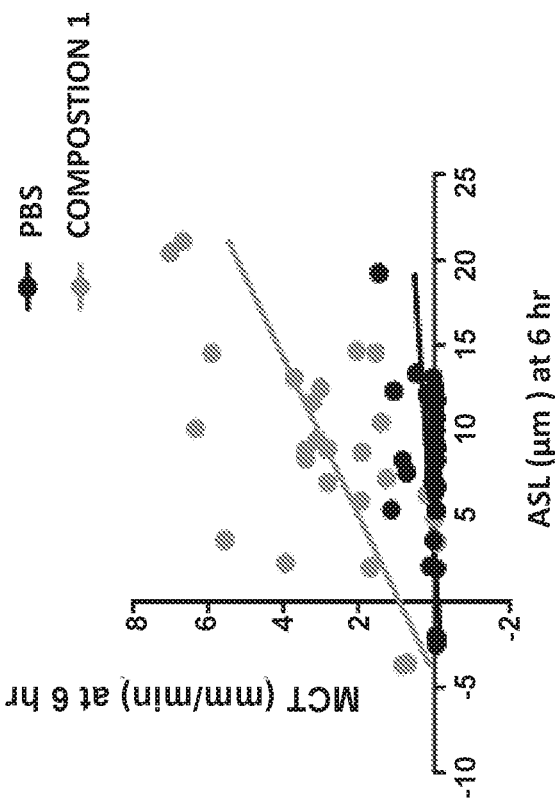

Mucus viscosity is the dominant mechanism in increasing MCT (Liu et al., Am J Prespir Cell Mol Biol. 2014, 51(4):485-93), rather than increasing airway surface liquid (ASL) and ciliary beat frequency (CBF). The slope analysis of MCT relative to airway surface liquid (ASL) and ciliary beat frequency (CBF) at 6 hours after administration of Composition 1 compared to PBS in primary human bronchial epithelial cells isolated from cystic fibrosis patients (dF508−/− cells) are shown in FIG. 8A and FIG. 8B, respectively. Composition 1 enhanced MCT and functionally and proportionally increased ASL and CBF. These results show that Compositon 1 can restore dF508 CF human bronchial epithelial (HBE) cells to normal MCT levels without increasing ASL and CBF to supranormal levels, which could disrupt MCT function by oversaturating the mucus layer or resulting in a fast, but too erratic ciliary beat pattern that disrupts mucus movement. These results support that Composition 1 has an effect on MCT is by decreasing mucus viscosity.

Example 11

Composition 1 Reduces Released MMP-9 Activity from Activated Neutrophils

Metalloprotease-9 (MMP-9) release from LPS-stimulated neutrophils after administration of Composition 1 at dilutions of 1:100 and 1:10 was assessed. Peripheral neutrophils were isolated from blood collected from a healthy donor. The neutrophils were treated with one of two dilutions of Composition 1 (1:10 or 1:100) or media (Med) only for 1 hour. They were then stimulated with 10 or 100 μg LPS for 1 hour. Supernatants from the cultures were collected and assessed via MMP-9 zymogram.

FIG. 9 shows metalloprotease-9 (MMP-9) release from LPS-stimulated neutrophils after 1-hour treatment with Composition 1 (Ar) at dilutions of 1:100 and 1:10 compared to media (Med) and LPS only controls. MMP-9 is the 75-100 kDa band on the gel.

During neutrophilic extracellular trap formation, or degranulation, matrix metalloproteinases (MMPs) are released and are associated with exacerbating chronic inflammatory airways diseases by breaking down airway epithelia. MMP-9 is released from LPS-stimulated neutrophils and is associated with clinical decline in cystic fibrosis patients (Gaggar et al., Eur Respir J., 2011 38(3):721-727).

Composition 1 significantly decreases metalloprotease-9 release from LPS-stimulated neutrophils. The 1:100 dilution decreases MMP-9 expression induced by LPS 100 by about 50%. The 1:10 dilution decreases the same stimulation by about 75%.

These results show that Composition 1 decreased neutrophil release of MMP-9 in vitro and acts as an anti-inflammatory agent.

Example 12

Composition 1 Reduces Neutrophil and Macrophage-associated Cytokines MIP 1α and MIP1β

Peripheral neutrophils were isolated from blood collected from a healthy donor. The neutrophils were treated with one of two dilutions of Composition 1 (1:10 or 1:100) or media only for 1 hour. They were then stimulated with 10 or 100 μg LPS for 1 hr. Supernatants from the cultures were collected and assessed via multiplex analysis at 15 minutes and 1 hour after stimulation.

Neutrophil and macrophage-associated cytokines: macrophage inflammatory protein 1α (MIP1α) (FIG. 10A) and macrophage inflammatory protein 1β (MIP1β) (FIG. 10B) release levels from LPS-activated neutrophils after administration of Composition 1 at dilutions of 1:100 and 1:10 were reduced 1 hour after stimulation compared to media (M) and LPS only controls.

Example 13

Combination of Composition 1 and VX-770/809

The effect of the combination of Composition 1 and VX-770/809 on MCT rate, ASL, and CBF was tested. VX-770/809 is a CFTR-specific modulator/potentiator/corrector that allows for cystic fibrosis transmembrane receptor (CFTR) expression and gating on the surface of dF508 HBEs. VX-770, also known as ivacaftor, is a CFTR potentiator. VX-809, also known as lumacaftor, is a CFTR corrector. However, use of VX-770/809 alone does not alleviate all respiratory symptoms.

MCT rate was assessed in a mucociliary clearance assay according to the methods in Example 3 above. Images from a video showing the effect of Composition 1 in combination with VX-770/809 compared to VX-770/809 alone and PBS control on the functional microanatomy of the primary human bronchial epithelial cells isolated from cystic fibrosis patients (dF508−/− cells) is shown FIG. 11. The results for the VX-770-809 treated cells showed that despite having slightly increased MCT, a mucus bilayer formed, preventing adequate MCT movement (FIG. 11, center panel). Combining Composition 1 with VX-770/809 resulted in not only a significant increase in MCT, but also breakdown of the mucus bilayer, allowing for better movement MCT compared to VX-770/809 alone.

These results showed that the combination of Composition 1 and VX-770/809 enhanced MCT rate compared to PBS control and decreased mucus bilayer associated with use VX-770/809 in a mucociliary clearance assay.

Quantification of ASL, CBF and MCT changes with Composition 1 alone, VX-770/809 and the combination of the two on dF508 CF HBE cells is shown in FIG. 12A. The combination of Composition 1 and VX-770/809 resulted in the greatest increase in MCT, CBF, and ASL. These data demonstrate the improved effect of Composition 1 when used in combination with the the CFTR VX-770/809.

As shown in FIG. 12B, incubation with Composition 1, or Composition 1 plus VX-770 and VX-809 increased the mucociliary transport of dF508−/− primary human bronchial epithelial cells compared to incubation with a PBS control or compared to VX-770 plus VX-809 alone. These data demonstrate that Composition 1 enhances the mucociliary transport of primary human bronchial epithelial cells in a dose-dependent manner. The results represent combined data taken from 20 samples of HBE monolayers across 3 CF donors homozygous for F508del.

Example 14

Clinical Study for Administration of Composition 1 to Bilateral Lung Transplant Patients The effects of Composition 1 (as prepared in Example 1) in post-bilateral lung transplant patients on pulmonary function (assessed by FEV1 change), changes in fractional exhaled nitric oxide (FeNO), and changes in quality of life were assessed. In short, Composition 1 (4 ml) was nebulized twice daily to four (4) patients post-lung transplant using a PART eFlow nebulizer.

Each patient's change in pulmonary function was assessed using the linear slope of FEV1 change at enrollment (baseline) and 1 month. Lung transplant patients had increased clinic and home spirometric measurements after using Composition 1 for one month. This change correlated with a positive change in quality of life, as measured by St. George's Respiratory Questionnaire. These pulmonary function results after 1 month are shown in FIG. 13.

Each patient's changes in FENO was assessed using change in mean baseline FENO measurements to the mean measurements post-Composition 1 use after 1 month. Patients had decreased FENO measurements after using Composition 1 for one month. Decreased FENO from baseline indicates resolution of inflammation/infection in patients post lung transplants (see, e.g., Fisher, A., Thorax 1998; 53:454-458). This change correlated with a positive change in quality of life, as measured by St. George's Respiratory Questionnaire. These FENO results after 1 month are shown in FIG. 14.

Example 15

Storage Stability of Composition 1

The effects of storage on ascorbic acid compositions including varying amounts of buffer with a consistent glutathione concentration were tested. For preparation of Formulations 1-9 (Formulation 9 corresponds to Composition 1 (as shown in Example 1)), solutions were mixed using sterile water for injection and stored in airtight, containers that were protected from light. At testing, Formulations 1-9 were evaluated to determine ascorbic acid and reduced and oxidized glutathione concentrations. A standard RP-HPLC method for these analytes was used. The method was validated including specificity, accuracy, repeatability, LOQ, mini linearity, in-vial NPLC sample stability and stability-indicating check with informal forced degradation samples. The pH of each formulation was determined using a pH probe place in a sample of each solution. Results are shown in FIG. 15. ascorbic (ACS) alone was unstable under the conditions tested (−20° C., 5° C., ambient) (data not shown).

Formulation stability is critical to clinical application to ensure consistent product and efficacy over time. Acidic conditions are present in chronic inflammatory airways diseases and contribute to disease (Morice, Breathe 2013 9: 256-266; Tang et al., J Clin Invest. 2016; 126(3):879-891; Tate et al., Thorax 2002; 57:926-929). Further, innate immune functions, such as adequate mucus clearance, optimal mucus viscosity, and innate bactericidal activity are optimal at a slightly acidic pH between 6-7 (Fisher et al., J Membr Biol. 2006; 211(3): 139-150). Thus, acidic conditions can impair immune functions and result in airway epithelia death and dysfunction.

After storage for about 72 hours at about 2-8° C., only Composition 1 (Formulation 9) achieved good solubility, no detectable precipitate formation, and maintained a pH of about 6-7. Furthermore, the impurities after storage for about 72 hours at about 2-8° C. were less than 4%, i.e., 3.8%, for Composition 1.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of treating a subject having a pulmonary or airway viral infection, comprising administering to the subject a therapeutically effective amount of a composition comprising:
   (a) glutathione, a glutathione derivative, a glutathione conjugate, or a pharmaceutically-acceptable salt thereof;
   (b) an ascorbic acid; and
   (c) a bicarbonate,
wherein the molar ratio of (a):(b):(c) is about 0.1-0.5:0.5-1:1.

2. The method of claim 1, wherein the bicarbonate is sodium bicarbonate.

3. The method of claim 1, wherein the bicarbonate is about 1-30% by weight.

4. The method of claim 1, wherein the molar ratio of (a):(b):(c) is about 0.4-0.5:0.5-1:1.

5. The method of claim 1, wherein the molar ratio of (a):(b):(c) is about 0.4-0.5:0.5:1 or 0.4-0.5:1:1.

6. The method of claim 1, wherein the composition comprises about 0.49 M glutathione, about 0.50 M ascorbic acid, and about 1 M sodium bicarbonate.

7. The method of claim 1, wherein the pH of the composition is about 5.5 to about 10, about 5.5 to about 8, about 6 to about 10, or about 6 to about 8.

8. The method of claim 1, wherein the composition is an aqueous solution.

9. The composition of claim 8, wherein the aqueous solution is constituted from a dry powder.

10. The method of claim 1, wherein the composition is suitable for administration by inhalation.

11. The method of claim 1, wherein the administration reduces airway inflammation in the subject suffering from the pulmonary or airway viral infection.

12. A method of upregulating mucociliary clearance in a subject suffering from a pulmonary or airway viral infection comprising administering to the subject a composition comprising:
   (a) glutathione, a glutathione derivative, a glutathione conjugate, or a pharmaceutically-acceptable salt thereof;

(b) an ascorbic acid; and
(c) a bicarbonate,
wherein the molar ratio of (a):(b):(c) is about 0.1-0.5:0.5-1:1.

13. The method of claim 12, wherein the bicarbonate is sodium bicarbonate.

14. The method of claim 12, wherein the bicarbonate is about 1-30% by weight.

15. The method of claim 12, wherein the molar ratio of (a):(b):(c) is about 0.4-0.5:0.5-1:1.

16. The method of claim 12, wherein the molar ratio of (a):(b):(c) is about 0.4-0.5:0.5:1 or 0.4-0.5:1:1.

17. The method of claim 12, wherein the composition comprises about 0.49 M glutathione, about 0.50 M ascorbic acid, and about 1 M sodium bicarbonate.

18. The method of claim 12, wherein the pH of the composition is about 5.5 to about 10, about 5.5 to about 8, about 6 to about 10, or about 6 to about 8.

19. The method of claim 12, wherein the composition is an aqueous solution.

20. The method of claim 19, wherein the aqueous solution is constituted from a dry powder.

21. The method of claim 12, wherein the composition is suitable for administration by inhalation.

22. The method of claim 12, wherein administering said composition decreases mucus viscosity of the subject.

23. The method of claim 12, wherein administering said composition increases ciliary beat frequency of the subject's airway epithelial cells.

* * * * *